(12) United States Patent
Bolli et al.

(10) Patent No.: US 8,598,208 B2
(45) Date of Patent: Dec. 3, 2013

(54) PYRIDINE DERIVATIVES AS S1P1/EDG1 RECEPTOR MODULATORS

(75) Inventors: Martin Bolli, Allschwil (CH); Cyrille Lescop, Kembs (FR); Boris Mathys, Egerkingen (CH); Claus Mueller, Weil am Rhein (DE); Oliver Nayler, Arlesheim (CH); Beat Steiner, Dornach (CH); Jorg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 320 days.

(21) Appl. No.: 12/673,918

(22) PCT Filed: Aug. 14, 2008

(86) PCT No.: PCT/IB2008/053269
§ 371 (c)(1),
(2), (4) Date: Feb. 17, 2010

(87) PCT Pub. No.: WO2009/024905
PCT Pub. Date: Feb. 26, 2009

(65) Prior Publication Data
US 2011/0212998 A1    Sep. 1, 2011

(30) Foreign Application Priority Data
Aug. 17, 2007  (WO) .................. PCT/IB2007/053293

(51) Int. Cl.
*A61K 31/443* (2006.01)
*C07D 401/14* (2006.01)

(52) U.S. Cl.
USPC .......................................... 514/333; 546/256

(58) Field of Classification Search
USPC .......................................... 546/256; 514/333
See application file for complete search history.

(56) References Cited

U.S. PATENT DOCUMENTS

| | | | |
|---|---|---|---|
| 3,647,809 | A | 3/1972 | Reiter et al. |
| 8,178,562 | B2 | 5/2012 | Bolli et al. |
| 8,288,554 | B2 | 10/2012 | Bolli et al. |
| 8,299,086 | B2 | 10/2012 | Bolli et al. |
| 2010/0063108 | A1 | 3/2010 | Bolli et al. |
| 2010/0087417 | A1 | 4/2010 | Bolli et al. |
| 2010/0087495 | A1 | 4/2010 | Bolli et al. |
| 2010/0168005 | A1 | 7/2010 | Bolli et al. |
| 2010/0331372 | A1 | 12/2010 | Bolli et al. |
| 2011/0028448 | A1 | 2/2011 | Bolli et al. |
| 2011/0028449 | A1 | 2/2011 | Bolli et al. |
| 2011/0046170 | A1 | 2/2011 | Bolli et al. |
| 2012/0108638 | A1 | 5/2012 | Bolli et al. |

FOREIGN PATENT DOCUMENTS

| | | |
|---|---|---|
| WO | WO 91/15583 | 10/1991 |
| WO | WO 99/46277 | 9/1999 |
| WO | WO 01/12627 | 2/2001 |
| WO | WO 02/068417 | 9/2002 |
| WO | WO 03/062248 | 7/2003 |
| WO | WO 03/062252 | 7/2003 |
| WO | WO 2004/035538 | 4/2004 |
| WO | WO 2004/103279 | 12/2004 |
| WO | WO 2005/032465 | 4/2005 |
| WO | WO 2005/058848 | 6/2005 |
| WO | WO 2005/115382 | 12/2005 |
| WO | WO 2006/097817 | 9/2006 |
| WO | WO 2006/114400 | 11/2006 |
| WO | WO 2006/131336 | 12/2006 |
| WO | WO 2007/001973 | 1/2007 |
| WO | WO 2007/085451 | 8/2007 |
| WO | WO 2008/076356 | 6/2008 |
| WO | WO 2009/151529 | 12/2009 |

OTHER PUBLICATIONS

Hu et al., "Sphingosine-1-phosphate, etc.," Mol. Biol. Rep. (2011) 38:4225-4230.*
Van der Giet et al., "Relevance and potential, etc.," Biol. Chem., 389, pp. 1381-1390 (2008).*
Jo et al., "Spingosine-1-phosphate, etc.," Kidney International (2008) 73, 1220-1230.*
Bode et al., "Immune Regulation, etc.," Arch. Immunol. Ther. Exp. (2012) 60: 3-12.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Robinson, Medical Therapy of Inflammatory Bowel Disease for the 21st century, Eur. J. Surg. 164, Suppl. 582, pp. 90-98, (1998).*
Spiegel et al., Nature Reviews Immunology, vol. 11, No. 6, pp. 403-415, Jun. 2011.*
Biyouki, M. A. A., et al., "Hydroxymethylation and Carbamoylation of Di- and Tetramethylpyridines Using Radical Substitution (Minisci) Reactions", Synthetic Communications, vol. 28, pp. 3817-3825, (1989).

(Continued)

*Primary Examiner* — Patricia L Morris
(74) *Attorney, Agent, or Firm* — Hoxie & Associates LLC

(57) ABSTRACT

The invention relates to novel pyridine derivatives of formula (I), their preparation and their use as pharmaceutically active compounds. Said compounds particularly act as immuno-modulating agents. Formula (I) wherein A represents and the other substituents are as defined in the claims.

Pyridine$^1$-A-Pyridine$^2$    (I)

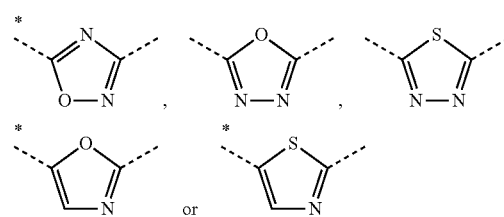

(A)

8 Claims, No Drawings

(56) References Cited

OTHER PUBLICATIONS

Brain, C.T., et al., "Novel procedure for the synthesis of 1,3,4-oxadiazoles from 1,2-diacylhydrazines using polymer-supported Burgess reagent under microwave conditions", Tetrahedron Lett., vol. 40, pp. 3275-3278, (1999).
Cui, J., et al., "Design and Synthesis of Highly Constrained Factor Xa Inhibitors: Amidine-Substituted Bis(benzoyl)[1,3]-diazepan-2-ones and Bis(benzylidene)-bis(gem-dimethyl)cycloketones", Biorg. Med. Chem., vol. 11, pp. 3379-3392 (2003).
Fallahpour, R.-A., "An Efficient and Easy Route to Trimethyl Derivatives of 2,2':6',2"-Terpyridine", Synthesis, No. 12, pp. 1665-1667, (2000).
Finch, N., et al., "Synthesis and Antihypertensive Activity of 5-Amino-2-pyridinecarbozylic Acid Derivatives", J. Med. Chem., vol. 23, pp. 1405-1410, (1980).
Furstner, A., et al., "Iron-Catalyzed Cross-Coupling Reactions", J. Am. Chem. Soc., vol. 124, pp. 13856-13863, (2002).
Furstner, A., et al., "Iron-Catalyzed Cross-Coupling Reactions of Alkyl-Grignard Reagents with Aryl Chlorides, Tosylates, and Triflates", Angew. Chem. Int. Ed., vol. 114, pp. 632-635, (2002).
Gangloff, A.R., et al., "Synthesis of 3,5-disubstituted-1,2,4-oxadiazoles using tetrabutylammonium fluoride as a mild and efficient catalyst", Tetrahedron Lett., vol. 42, pp. 1441-1443, (2001).
Garcia, M.A., et al., "Synthesis, Biological Evaluation, and Three-Dimensional Quantitative Structure-Activity Relationship Study of Small-Molecule Positive Modulators of Adrenomedullin", J. Med. Chem., vol. 48, pp. 4068-4075, (2005).
Gierczyk, B., et al., "Synthesis of Substituted 1,3,4-Thiadiazoles Using Lawesson's Reagent", Organic Preparations and Procedures Int., vol. 37, pp. 213-222, (2005).
Gould, P.L., "Salt Selection for Basic Drugs", International Journal of Pharmaceutics, vol. 33, pp. 201-217, (1986).
Habermehl, N. C., et al., "Asymmetric Transformation of a Double-Stranded, Dicopper(I) Helicate Containing Achiral Bis(bidentate) Schiff Bases", Inorganic Chemistry, vol. 45, pp. 1445-1462, (2006).
Hamze, A., et al., "Synthesis of Various 3-Substituted 1,2,4-Oxadiazole-Containing Chiral â3- and r-Amino Acids from Fmoc-Protected Aspartic Acid", J. Org. Chem., vol. 68, pp. 7316-7321, (2003).
Harris, M. C., "Sequential N-Arylation of Primary Amines as a Route to Alkyldiarylamines", J. Org. Chem., vol. 64, pp. 6019-6022 (1999).
Hla, T., et al., "An Abundant Transcript Induced in Differentiating Human Endothelial Cells Encodes a Polypeptide with Structural Similarities to G-protein-coupled Receptors", Biol. Chem., vol. 265, pp. 9308-9313, (1990).
John, E.O., et al., "Reactions of (Difluoroamino)difluoroacetonitrile and (Difluoroamino) difluoroacetamidoxime", Inorganic Chemistry, vol. 27, pp. 3100-3104, (1988).
Kaboudin, B., et al., "One-Pot Synthesis of 1,2,4-Oxadiazoles Mediated by Microwave Irradiation Under Solvent-Free Condition", Heterocycles, vol. 60, No. 10, pp. 2287-2292, (2003).
Kaminski, T., et al., "Side-Chain Retention During Lithiation of 4-Picoline and 3,4-Lutidine: Easy Access to Molecular Diversity in Pyridine Series", J. Org. Chem., vol. 19, pp. 3855-3860, (2003).
Katz, R. B., et al., "An Improved Method for the Mono-Hydroxymethylation of Pyridines. A Modification of the Minisci Procedure", Synthetic Communications, vol. 19, pp. 317-325, (1989).
Kerins, F., et al., "Generation of Substituted Styrenes via Suzuki Cross-Coupling of Aryl Halides with 2,4,6-Trivinylcyclotriboroxane", J. Org. Chem., vol. 67 pp. 4968-4971, (2002).
Kiryanov, A. A., et al., "Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis", J. Org. Chem., vol. 66, pp. 7925-7929, (2001).

Lamattina, J. L., "The Synthesis of 2-Amino-4-(4-Imidazolyl) pyridines", J. Heterocyclic Chem., vol. 20, pp. 533-538, (1983).
Matsushita, H., et al., "Palladium-Catalyzed Reactions of Allylic Electrophiles with Organometallic Reagents. A Regioselective 1,4-Elimination and a Regio- and Stereoselective Reduction of Allylic Derivatives", J. Org. Chem., vol. 47, pp. 4161-4165, (1982).
Natarajan, S. R., et al., "p38 MAP Kinase Inhibitors. Part 1: Design and Development of a New Class of Potent and Highly Selective Inhibitors Based on 3,4-Dihydropyrido[3,2-d]pyrimidone Scaffold", Bioorganic & Medicinal Chemistry Letters, vol. 13, pp. 273-276, (2003).
Paine III, J. B., "A Convenient Synthesis of Nicotinate Esters from 3-Cyanopyridones", J. Heterocyclic Chem., vol. 24, pp. 351-355, (1987).
Pesson, M., et al., Antibacteriens de Synthese—Derives de l'acide pipemidique, Eur. J. Med. Chem., vol. 15, pp. 263-268, (1980).
Pierrat, P., et al., "Unusual t-BuLi Induced Ortholithiation versus Halogen-Lithium Exchange in Bromopyridines: Two Alternative Strategies for Functionalization", Synlett, No. 13, pp. 2319-2322, (2004).
Poulain, R.F., et al. "Parallel synthesis of 1,2,4-oxadiazoles from carboxylic acids using an improved, uronium-based, activation", Tetrahedron Lett., vol. 42, pp. 1495-1498, (2001).
Sato, N., et al., "Synthesis and evaluation of substituted 4-alkoxy-2-aminopyridines as novel neuropeptide Y1 receptor antagonists", Bioorganic & Medicinal Chemistry Letters, vol. 14, pp. 1761-1764, (2004).
Srivastava, R.M., et al., Synthesis of 3-Aryl-5-[Thien-3-YI Methyl]-1,2,4-Oxadiazoles, Synthetic Commun., vol. 29, pp. 1437-1450, (1999).
Stauffer, S., et al., "High Turnover Number and Rapid, Room-Temperature Amination of Chloroarenes Using Saturated Carbene Ligands", Organic Letters, vol. 2, No. 10, pp. 1423-1426, (2000).
Suzuki, T., et al., "Synthesis of the Selective 5- Hydroxytryptamine4 (5-HT$_4$) Receptor Agonist (+)-(S)-2-Chloro-5-methoxy-4-[5-(2-piperidylmethyl)-1,2,4-oxadiazol-3-yl]aniline", Chem. Pharm. Bull., vol. 47, No. 1, pp. 120-122, (1999).
Wagaw, S., et al., "The Synthesis of Aminopyridines: A Method Employing Palladium-Catalyzed Carbon-Nitrogen Bond Formation", J. Org. Chem., vol. 61, pp. 7240-7241, (1996).
Wild, N., et al., "Asymmetric Synthesis of (S)-(--)-Acromelobic Acid", European. J. Org. Chem., pp. 4445-4449, (2003).
Wolfe, J. P., et al., "Simple, Efficient Catalyst System for the Palladium-Catalyzed Amination of Aryl Chlorides, Bromides, and Triflates", J. Org. Chem., vol. 65, pp. 1158-1174, (2000).
Yan, L., et al., "Discovery of 3-arylpropionic acids as potent agonists of sphingosine-1-phosphate receptor-1 (S1P1) with high selectivity against all other known S1P receptor subtypes", Bioorganic & Med. Chem. Lett., vol. 16, pp. 3679-3683, (2006).
Ziener, U., et al., "Recognition-Directed Supramolecular Assemblies of Metal Complexes of Terpyridine Derived Ligands with Self-Complementary Hydrogen Bonding Sites", Chemistry-A European Journal, vol. 6, pp. 4132-4139, (2000).
Notice of Allowance dated Nov. 28, 2012 for U.S. Appl. No. 12/920,574.
Buzard et al; "Expert Opinion on Therapuetic Patents"; vol. 18, No. 10; pp. 1141-1159 (2008).
Notice of Allowanced dated Jun. 19, 2013 for U.S. Appl. No. 12/310,801.
Office Action—Final dated Nov. 8, 2012 for U.S. Appl. No. 12/310,801.
Office Action—Non-Final dated Oct. 9, 2012 for U.S. Appl. No. 12/920,572.
Office Action dated Dec. 6, 2011 for U.S. Appl. No. 12/310,801.
Office Action dated Jun. 27, 2012 for U.S. Appl. No. 12/310,801.
Patani et al; "Bioisosterism: A Rational Approach in Drug Design"; Chem. Rev. 1996, vol. 96, No. 8, pp. 3147-3176.
Schurer et al; ACS Chemical Biolog, vol. 3; No. 8; pp. 486-498; 2008.
Silverman; "The Organic Chemistry of Drug Design and Drug Action"; 2004; Elsevier, pp. 29-32.

(56) References Cited

OTHER PUBLICATIONS

Trapani et al; "Propofol Analgoues. Synthesis, Relationships between Structure and Affinity at GABAA Receptor in Rat Brain, and Differential Electrophysiological Profile at Recombinant Human GABAA Receptors"; Journal of Medicinal Chemistry, 1998, pp. 1846-1854, vol. 41.

U.S. Appl. No. 13/980,761, Bolli et al.
Notice of Allowance of U.S. Appl. No. 12/531,374 dated Jul. 17, 2013, Bolli et al.
Notice of Allowance of U.S. Appl. No. 12/920,656 dated Jun. 24, 2013, Bolli et al.

* cited by examiner

PYRIDINE DERIVATIVES AS S1P1/EDG1 RECEPTOR MODULATORS

CROSS REFERENCE TO RELATED APPLICATIONS

This application is a United States Application under 35 U.S.C. 371 claiming benefit of International Application No. PCT/IB2008/053269, filed on Aug. 14, 2008, which claims the benefit of International Application No. PCT/IB2007/053293, filed on Aug. 17, 2007, the contents of each of which are incorporated herein by reference.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

The general terms used hereinbefore and hereinafter preferably have, within this disclosure, the following meanings, unless otherwise indicated:

The term "$C_{x-y}$-alkyl" (x and y each being an integer), refers to a saturated straight or branched chain alkyl group containing x to y carbon atoms. For example a $C_{1-5}$-alkyl group contains from one to five carbon atoms. Representative examples of $C_{1-5}$-alkyl groups include methyl, ethyl, n-propyl, iso-propyl, n-butyl, iso-butyl, sec-butyl, tert-butyl, n-pentyl, iso-pentyl, 3-pentyl, and 2,2,2-trimethylethyl. Preferred examples of $C_{1-5}$-alkyl groups are methyl, ethyl, n-propyl, iso-propyl, n-butyl, iso-butyl, and 3-pentyl. Preferred examples of $C_{1-4}$-alkyl groups are methyl, ethyl, n-propyl, iso-propyl, n-butyl, and iso-butyl. Preferred examples of $C_{2-5}$-alkyl groups are ethyl, n-propyl, iso-propyl, iso-butyl, and 3-pentyl. Preferred examples of $C_{2-4}$-alkyl groups are ethyl, n-propyl, iso-propyl, and iso-butyl. Preferred examples of $C_{1-3}$-alkyl groups are methyl and ethyl.

The term "$C_{x-y}$-alkoxy" (x and y each being an integer), used alone or in combination, refers to an alkyl-O— group wherein the alkyl group refers to a straight or branched chain alkyl group containing x to y carbon atoms. For example a $C_{1-4}$-alkoxy group contains from one to four carbon atoms. Representative examples of $C_{1-4}$-alkoxy groups include methoxy, ethoxy, n-propoxy, iso-propoxy, n-butoxy, iso-butoxy, sec-butoxy and tert-butoxy. Preferred examples of $C_{2-4}$-alkoxy groups are ethoxy, n-propoxy, and iso-propoxy. A preferred example of a $C_{1-3}$-alkoxy group is methoxy.

The term "$C_{x-y}$-cycloalkyl" (x and y each being an integer), used alone or in combination, refers to a cycloalkyl group containing x to y carbon atoms. For example a $C_{3-6}$-cycloalkyl group contains from three to six carbon atoms. Representative examples of $C_{3-6}$-cycloalkyl groups include cyclopropyl, cyclobutyl, cyclopentyl, and cyclohexyl. Preferred are cyclopropyl, cyclobutyl and cyclopentyl. Most preferred is cyclopentyl.

The compounds of Formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

Any reference hereinbefore or hereinafter to a compound of Formula (I) is to be understood as referring also to salts, especially pharmaceutically acceptable salts, of a compound of Formula (I), as appropriate and expedient.

Where the plural form is used for compounds, salts, pharmaceutical compositions, diseases and the like, this is intended to mean also a single compound, salt, or the like.

Salts are preferably the pharmaceutically acceptable salts of the compounds of Formula (I).

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

i) The invention relates to novel pyridine compounds of Formula (I),

Pyridine$^1$-A-Pyridine$^2$   Formula (I)

wherein
Pyridine$^1$ represents

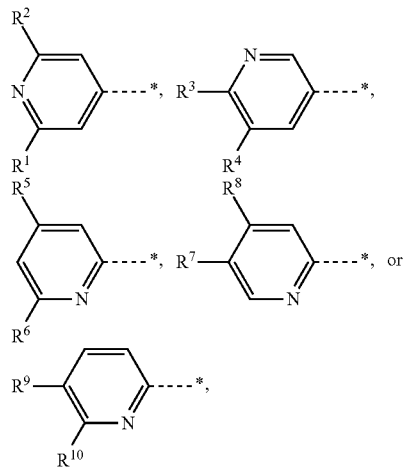

wherein the asterisks mark the bond with which the Pyridine$^1$ ring is bound to A;
$R^1$ represents $C_{1-5}$-alkyl, $C_{1-4}$-alkoxy, $C_{3-6}$-cycloalkyl, hydroxymethyl, or $NR^{1a}R^{1b}$;
$R^{1a}$ represents $C_{1-4}$-alkyl;
$R^{1b}$ represents hydrogen, or $C_{1-3}$-alkyl; or $R^{1a}$ and $R^{1b}$, together with the nitrogen that is attached to the pyridine, form a pyrrolidine ring;
$R^2$ represents hydrogen, or $C_{1-4}$-alkyl, or in case $R^1$ represents $C_{1-5}$-alkyl or $C_{3-6}$-cycloalkyl, $R^2$ may in addition represent methoxy;
$R^3$ represents $C_{1-5}$-alkyl, $C_{1-4}$-alkoxy, $C_{3-6}$-cycloalkyl, or $NR^{3a}R^{3b}$;
$R^{3a}$ represents $C_{1-4}$-alkyl;
$R^{3b}$ represents hydrogen, or $C_{1-3}$-alkyl;
$R^4$ represents $C_{1-4}$-alkyl, or hydrogen;
$R^5$ represents $C_{1-5}$-alkyl, methoxy, or $NR^{5a}R^{5b}$; and $R^6$ represents $C_{1-2}$-alkyl;
$R^{5a}$ represents $C_{1-4}$-alkyl;
$R^{5b}$ represents hydrogen, or $C_{1-3}$-alkyl; or
$R^5$ represents $C_{1-2}$-alkyl, or methoxy; and $R^6$ represents $C_{1-5}$-alkyl, or $NR^{6a}R^{6b}$;
$R^{6a}$ represents $C_{1-4}$-alkyl;
$R^{6b}$ represents hydrogen, or $C_{1-3}$-alkyl;
$R^7$ represents $C_{1-5}$-alkyl;
$R^8$ represents $C_{1-2}$-alkyl, or methoxy;
$R^9$ represents $C_{1-5}$-alkyl;
$R^{10}$ represents $C_{1-2}$-alkyl;
A represents

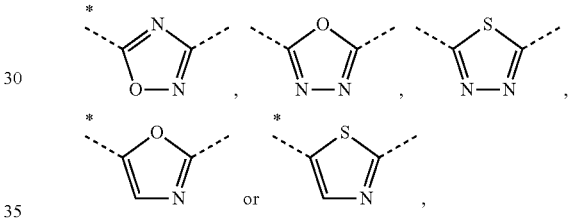

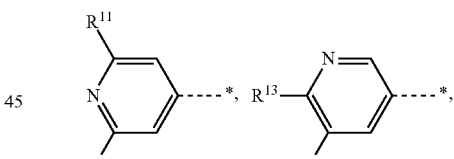

wherein the asterisks indicate the bond that is linked to the Pyridine$^1$ ring;
Pyridine$^2$ represents

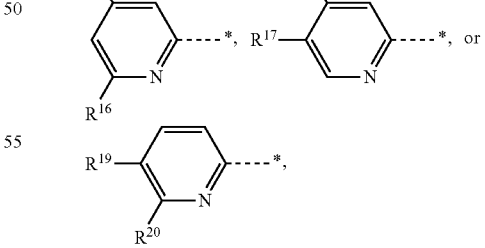

wherein the asterisks mark the bond with which the Pyridine$^2$ ring is bound to A;
$R^{11}$ represents $C_{1-4}$-alkyl, $C_{1-3}$-alkoxy, hydroxymethyl, or $NR^{11a}R^{11b}$;
$R^{11a}$ represents $C_{1-3}$-alkyl;
$R^{11b}$ represents hydrogen, or $C_{1-2}$-alkyl;
$R^{12}$ represents hydrogen, or $C_{1-2}$-alkyl;

$R^{13}$ represents $C_{1-4}$-alkyl, or $NR^{13a}R^{13b}$;
$R^{13a}$ represents $C_{1-3}$-alkyl;
$R^{13b}$ represents hydrogen, or $C_{1-2}$-alkyl;
$R^{14}$ represents $C_{1-2}$-alkyl;
$R^{15}$ represents $C_{1-4}$-alkyl, or $NR^{15a}R^{15b}$; and $R^{16}$ represents $C_{1-2}$-alkyl;
$R^{15a}$ represents $C_{1-3}$-alkyl;
$R^{15b}$ represents hydrogen, or $C_{1-3}$-alkyl; or
$R^{15}$ represents $C_{1-2}$-alkyl; and $R^{16}$ represents $C_{1-4}$-alkyl, or $NR^{16a}R^{16b}$;
$R^{16a}$ represents $C_{1-3}$-alkyl;
$R^{16b}$ represents hydrogen, or $C_{1-2}$-alkyl;
$R^{17}$ represents $C_{1-4}$-alkyl;
$R^{18}$ represents $C_{1-2}$-alkyl, or methoxy;
$R^{19}$ represents $C_{1-4}$-alkyl; and
$R^{20}$ represents $C_{1-2}$-alkyl;
with the exception of 3-(2-ethyl-4-pyridyl)-5-(2-ethyl-4-pyridyl)-1,2,4-oxadiazole (U.S. Pat. No. 3,647,809).

ii) Another embodiment of the invention relates to pyridine compounds according to embodiment i), wherein $R^2$ represents hydrogen, or $C_{1-4}$-alkyl.

iii) Another embodiment of the invention relates to pyridine compounds according to embodiment i) or ii), wherein if $R^2$ or $R^4$ represents hydrogen, $R^{12}$ represents $C_{1-2}$-alkyl.

iv) Another embodiment of the invention relates to pyridine compounds according to any one of embodiments i) to iii), wherein Pyridine[1] represents

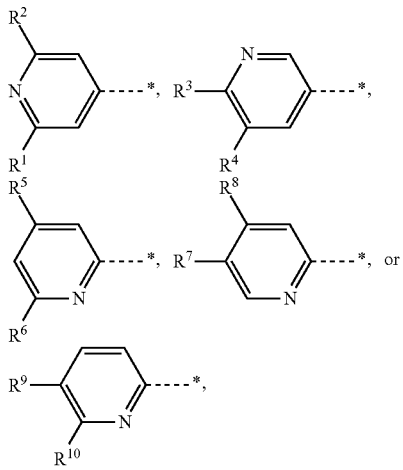

wherein the asterisks mark the bond with which the Pyridine[1] ring is bound to A;
$R^1$ represents $C_{1-5}$-alkyl, $C_{1-4}$-alkoxy, $C_{3-6}$-cycloalkyl, or $NR^{1a}R^{1b}$;
$R^{1a}$ represents $C_{1-4}$-alkyl;
$R^{1b}$ represents hydrogen, or $C_{1-3}$-alkyl; or $R^{1a}$ and $R^{1b}$, together with the nitrogen that is attached to the pyridine, form a pyrrolidine ring;
$R^2$ represents $C_{1-4}$-alkyl;
$R^3$ represents $C_{1-5}$-alkyl;
$R^4$ represents $C_{1-4}$-alkyl;
$R^5$ represents $C_{1-5}$-alkyl; and $R^6$ represents methyl; or
$R^5$ represents methyl, or methoxy; and $R^6$ represents $C_{1-5}$-alkyl;
$R^7$ represents $C_{1-5}$-alkyl;
$R^8$ represents $C_{1-2}$-alkyl;
$R^9$ represents $C_{1-5}$-alkyl;
$R^{10}$ represents $C_{1-2}$-alkyl;

A represents

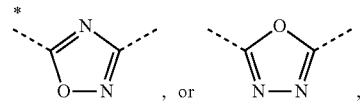

wherein the asterisk indicates the bond that is linked to the Pyridine[1] ring;
Pyridine[2] represents

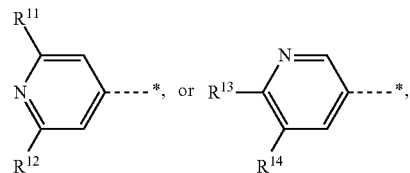

wherein the asterisks mark the bond with which the Pyridine[2] ring is bound to A;
$R^{11}$ represents $C_{1-4}$-alkyl, hydroxymethyl, or $NR^{11a}R^{11b}$;
$R^{11a}$ represents $C_{1-3}$-alkyl;
$R^{11b}$ represents hydrogen, or $C_{1-2}$-alkyl;
$R^{12}$ represents $C_{1-2}$-alkyl;
$R^{13}$ represents $C_{1-4}$-alkyl, or $NR^{13a}R^{13b}$;
$R^{13a}$ represents $C_{1-3}$-alkyl;
$R^{13b}$ represents hydrogen, or $C_{1-2}$-alkyl; and
$R^{14}$ represents $C_{1-2}$-alkyl.

v) Another embodiment of the invention relates to pyridine compounds according to any one of embodiments i) to iii), wherein Pyridine[1] represents

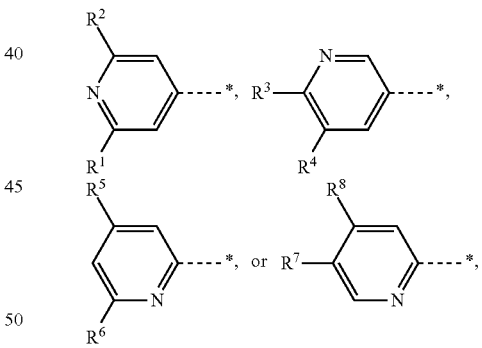

wherein the asterisks mark the bond with which the Pyridine[1] ring is bound to A;
$R^1$ represents $C_{1-5}$-alkyl, $C_{1-4}$-alkoxy, $C_{3-6}$-cycloalkyl, or $NR^{1a}R^{1b}$;
$R^{1a}$ represents $C_{1-4}$-alkyl;
$R^{1b}$ represents hydrogen, or $C_{1-3}$-alkyl;
$R^2$ represents $C_{1-4}$-alkyl;
$R^3$ represents $C_{1-5}$-alkyl, $C_{1-4}$-alkoxy, or $NR^{3a}R^{3b}$;
$R^{3a}$ represents $C_{1-4}$-alkyl;
$R^{3b}$ represents hydrogen, or $C_{1-3}$-alkyl;
$R^4$ represents $C_{1-4}$-alkyl;
$R^5$ represents $C_{1-2}$-alkyl;
$R^6$ represents $C_{1-5}$-alkyl, or $NR^{6a}R^{6b}$,
$R^{6a}$ represents $C_{1-4}$-alkyl;
$R^{6b}$ represents hydrogen, or $C_{1-3}$-alkyl;

$R^7$ represents $C_{1-5}$-alkyl; and
$R^8$ represents methyl.

vi) Another embodiment of the invention relates to pyridine compounds according to any one of embodiments i) to iv), wherein
Pyridine$^1$ represents

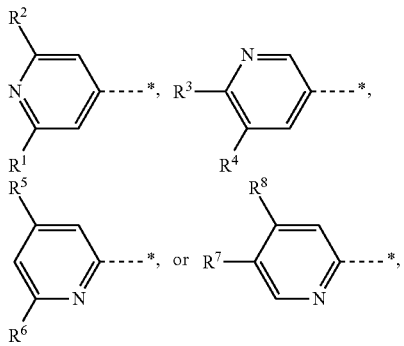

wherein the asterisks mark the bond with which the Pyridine$^1$ ring is bound to A;
$R^1$ represents $C_{2-5}$-alkyl, $C_{2-3}$-alkoxy, cyclopentyl, or $NR^{1a}R^{1b}$;
$R^{1a}$ represents $C_{1-3}$-alkyl;
$R^{1b}$ represents $C_{1-2}$-alkyl, or hydrogen;
$R^2$ represents $C_{1-2}$-alkyl;
$R^3$ represents $C_{2-4}$-alkyl;
$R^4$ represents $C_{1-2}$-alkyl;
$R^5$ represents methyl;
$R^6$ represents $C_{2-4}$-alkyl;
$R^7$ represents $C_{2-4}$-alkyl; and
$R^8$ represents methyl.

vii) Another embodiment of the invention relates to pyridine compounds according to any one of embodiments i) to vi), wherein Pyridine$^1$ represents

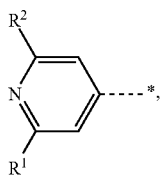

wherein the asterisk marks the bond with which the Pyridine$^1$ ring is bound to A.

viii) Another embodiment of the invention relates to pyridine compounds according to any one of embodiments i) to vii), wherein $R^1$ represents $C_{2-5}$-alkyl, $C_{2-3}$-alkoxy, cyclopentyl, or $NR^{1a}R^{1b}$, wherein $R^{1a}$ represents $C_{1-3}$-alkyl and $R^{1b}$ represents hydrogen, or $C_{1-2}$-alkyl (especially $R^1$ represents $C_{2-5}$-alkyl, or $NR^{1a}R^{1b}$, wherein $R^{1a}$ represents $C_{1-3}$-alkyl and $R^{1b}$ represents hydrogen); and $R^2$ represents $C_{1-2}$-alkyl.

ix) Another embodiment of the invention relates to pyridine compounds according to any one of embodiments i) to vii), wherein $R^1$ represents $C_{2-5}$-alkyl, and $R^2$ represents $C_{1-2}$-alkyl.

x) Another embodiment of the invention relates to pyridine compounds according to any one of embodiments i) to vii), wherein $R^1$ represents $NR^{1a}R^{1b}$, wherein $R^{1a}$ represents $C_{1-3}$-alkyl and $R^{1b}$ represents hydrogen; and $R^2$ represents $C_{1-2}$-alkyl.

xi) Another embodiment of the invention relates to pyridine compounds according to any one of embodiments i) to x), wherein A represents

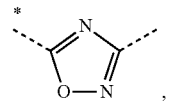

wherein the asterisk marks the bond that is linked to the Pyridine$^1$ ring.

xii) Another embodiment of the invention relates to pyridine compounds according to any one of embodiments i) to iii) and v) to xi), wherein
Pyridine$^2$ represents

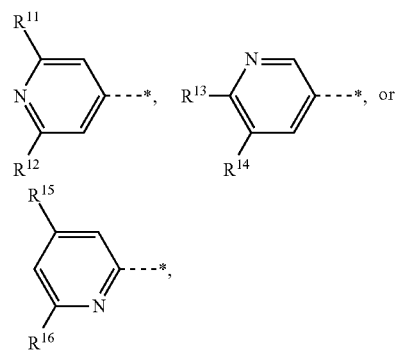

wherein the asterisks mark the bond with which the Pyridine$^2$ ring is bound to A;
$R^{11}$ represents $C_{1-4}$-alkyl, hydroxymethyl, or $NR^{11a}R^{11b}$;
$R^{11a}$ represents $C_{1-3}$-alkyl;
$R^{11b}$ represents hydrogen, or $C_{1-2}$-alkyl;
$R^{12}$ represents $C_{1-2}$-alkyl;
$R^{13}$ represents $C_{1-4}$-alkyl, or $NR^{13a}R^{13b}$;
$R^{13a}$ represents $C_{1-3}$-alkyl;
$R^{13b}$ represents hydrogen, or $C_{1-2}$-alkyl;
$R^{14}$ represents $C_{1-2}$-alkyl;
$R^{15}$ represents $C_{1-4}$-alkyl, and $R^{16}$ represents $C_{1-2}$-alkyl; or
$R^{15}$ represents $C_{1-2}$-alkyl; and $R^{16}$ represents $C_{1-4}$-alkyl, or $NR^{16a}R^{16b}$;
$R^{16a}$ represents $C_{1-3}$-alkyl; and
$R^{16b}$ represents hydrogen, or $C_{1-2}$-alkyl.

xiii) Another embodiment of the invention relates to pyridine compounds according to any one of embodiments i) to iii) and v) to xi), wherein Pyridine$^2$ represents

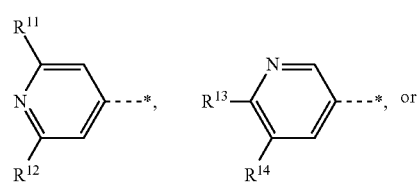

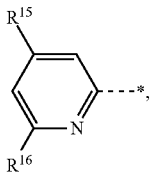

wherein the asterisks mark the bond with which the Pyridine² ring is bound to A;
$R^{11}$ represents $C_{1-2}$-alkyl, hydroxymethyl, or $NR^{11a}R^{11b}$;
$R^{11a}$ represents methyl;
$R^{11b}$ represents hydrogen, or methyl;
$R^{12}$ represents methyl;
$R^{13}$ represents $C_{1-3}$-alkyl, or $NR^{13a}R^{13b}$;
$R^{13a}$ represents $C_{1-3}$-alkyl;
$R^{13b}$ represents hydrogen;
$R^{14}$ represents methyl;
$R^{15}$ represents methyl;
$R^{16}$ represents $C_{1-2}$-alkyl, or $NR^{16a}R^{16b}$;
$R^{16a}$ represents methyl; and
$R^{16b}$ represents hydrogen.

xiv) Another embodiment of the invention relates to pyridine compounds according to any one of embodiments i) to xiii), wherein Pyridine² represents

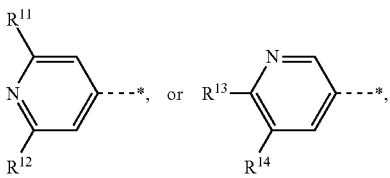

wherein the asterisks mark the bond with which the Pyridine² ring is bound to A.

xv) Another embodiment of the invention relates to pyridine compounds according to any one of embodiments i) to xiii), wherein Pyridine² represents

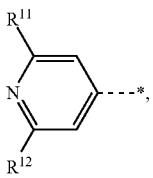

wherein the asterisk marks the bond with which the Pyridine² ring is bound to A.

xvi) Another embodiment of the invention relates to pyridine compounds according to any one of embodiments i) to xv), wherein $R^{11}$ represents methyl, ethyl, hydroxymethyl, methylamino, or dimethylamino (especially $R^{11}$ represents methyl, ethyl, or methylamino); and $R^{12}$ represents methyl.

xvii) Another embodiment of the invention relates to pyridine compounds according to any one of embodiments i) to xv), wherein $R^{11}$ represents methyl, or ethyl; and $R^{12}$ represents methyl.

xviii) Another embodiment of the invention relates to pyridine compounds according to any one of embodiments i) to xiv), wherein $R^{13}$ represents $C_{1-3}$-alkyl, or $NR^{13a}R^{13b}$, wherein $R^{13a}$ represents $C_{1-3}$-alkyl and $R^{13b}$ represents hydrogen; and $R^{14}$ represents methyl.

xix) Preferred pyridine compounds according to Formula (I) are selected from the group consisting of:
2-ethyl-4-[3-(2,6-dimethyl-4-pyridinyl)-[1,2,4]oxadiazol-5-yl]-6-methyl-pyridine;
2-ethyl-4-[3-(2-ethyl-6-methyl-4-pyridinyl)-[1,2,4]oxadiazol-5-yl]-6-methyl-pyridine;
2-ethyl-4-[3-(2-isobutyl-6-methyl-4-pyridinyl)-[1,2,4]oxadiazol-5-yl]-6-methyl-pyridine;
2-propyl-4-[3-(2,6-dimethyl-4-pyridinyl)-[1,2,4]oxadiazol-5-yl]-6-methyl-pyridine;
2-propyl-4-[3-(2-ethyl-6-methyl-4-pyridinyl)-[1,2,4]oxadiazol-5-yl]-6-methyl-pyridine;
2-isobutyl-4-[3-(2,6-dimethyl-4-pyridinyl)-[1,2,4]oxadiazol-5-yl]-6-methyl-pyridine;
2-isobutyl-4-[3-(2-ethyl-6-methyl-4-pyridinyl)-[1,2,4]oxadiazol-5-yl]-6-methyl-pyridine;
2-methylamino-4-[3-(2-ethyl-6-methyl-4-pyridinyl)-[1,2,4]oxadiazol-5-yl]-6-methyl-pyridine;
2-ethylamino-4-[3-(2-ethyl-6-methyl-4-pyridinyl)-[1,2,4]oxadiazol-5-yl]-6-methyl-pyridine;
2-isopropylamino-4-[3-(2-ethyl-6-methyl-4-pyridinyl)-[1,2,4]oxadiazol-5-yl]-6-methyl-pyridine;
2-diethylamino-4-[3-(2-ethyl-6-methyl-4-pyridinyl)-[1,2,4]oxadiazol-5-yl]-6-methyl-pyridine;
2-isobutyl-4-[3-(2-methylamino-6-methyl-4-pyridinyl)-[1,2,4]oxadiazol-5-yl]-6-methyl-pyridine;
2-isobutyl-4-[3-(2-isopropylamino-3-methyl-5-pyridinyl)-[1,2,4]oxadiazol-5-yl]-6-methyl-pyridine; and
2-(1-ethyl-propyl)-4-[3-(2-ethyl-6-methyl-4-pyridinyl)-[1,2,4]oxadiazol-5-yl]-6-methyl-pyridine.

xx) Additional preferred pyridine compounds according to Formula (I) are selected from the group consisting of:
2-isopropoxy-4-[3-(2-ethyl-6-methyl-4-pyridinyl)-[1,2,4]oxadiazol-5-yl]-6-methyl-pyridine;
2-isobutyl-4-[3-(2-ethyl-6-methyl-4-pyridinyl)-[1,2,4]oxadiazol-5-yl]-6-methoxy-pyridine;
2,6-diethyl-4-[3-(2,6-dimethyl-4-pyridinyl)-[1,2,4]oxadiazol-5-yl]-pyridine;
2,6-diethyl-4-[3-(2-ethyl-6-methyl-4-pyridinyl)-[1,2,4]oxadiazol-5-yl]-pyridine;
2-isobutyl-4-[3-(2,6-dimethyl-4-pyridinyl)-[1,2,4]oxadiazol-5-yl]-6-ethyl-pyridine;
2-isobutyl-4-[3-(2-ethyl-6-methyl-4-pyridinyl)-[1,2,4]oxadiazol-5-yl]-6-ethyl-pyridine;
2-(3-pentyl)-4-[3-(2,6-dimethyl-4-pyridinyl)-[1,2,4]oxadiazol-5-yl]-6-methyl-pyridine;
2-cyclopentyl-4-[3-(2,6-dimethyl-4-pyridinyl)-[1,2,4]oxadiazol-5-yl]-6-methyl-pyridine;
6-methoxy-2-(3-pentyl)-4-[3-(2-ethyl-6-methyl-4-pyridinyl)-[1,2,4]oxadiazol-5-yl]-pyridine;
2-cyclopentyl-4-[3-(2-ethyl-6-methyl-4-pyridinyl)-[1,2,4]oxadiazol-5-yl]-6-methoxy-pyridine;
6-methyl-2-(3-pentyl)-4-[2-(2,6-dimethyl-4-pyridinyl)-[1,3,4]thiadiazol-5-yl]-pyridine; and
6-methyl-2-(3-pentyl)-4-[2-(2-ethyl-6-methyl-4-pyridinyl)-[1,3,4]thiadiazol-5-yl]-pyridine.

The compounds of Formula (I) and their pharmaceutically acceptable salts can be used as medicaments, e.g. in the form of pharmaceutical compositions for enteral or parenteral administration and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Diseases or disorders associated with an activated immune system which can be treated and/or prevented with the compounds of Formula (I) include rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of Formula (I) are selected from multiple sclerosis and psoriasis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

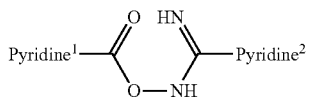

Structure 1

Compounds of Formula (I) which represent a [1,2,4]oxadiazole derivative, are prepared by reacting a compound of Structure 1 in a solvent such as dioxane, THF, dimethoxyethane, xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, Na$_2$CO$_3$, K$_2$CO$_3$, triethylamine, etc.), tetraalkylammonium salts, or water removing agents (e.g. oxalyl chloride, a carboxylic acid anhydride, POCl$_3$, PCl$_5$, P$_4$O$_{10}$, molecular sieves, methoxycarbonylsulfamoyl triethylammonium hydroxide (Burgess reagent), etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292; C. T. Brain, J. M. Paul, Y. Loong, P. J. Oakley, *Tetrahedron Lett.* 40 (1999) 3275-3278).

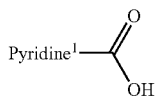

Structure 2

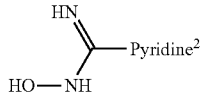

Structure 3

Compounds of Structure 1 may be prepared by reacting a compound of Structure 2 with a compound of Structure 3 in a solvent such as DMF, THF, DCM, etc. in the presence or absence of one or more coupling agents such as TBTU, DCC, EDC, HBTU, HOBt, CDI, PyBOP, etc. and in the presence or absence of a base such as triethylamine, DIPEA, NaH, K$_2$CO$_3$, etc. (Lit.: e.g. A. Hamze, J.-F. Hernandez, P. Fulcrand, J. Martinez, *J. Org. Chem.* 68 (2003) 7316-7321; and the literature cited above).

NC-Pyridine$^2$   Structure 4

Compounds of Structure 3 may be prepared by reacting a compound of Structure 4 with hydroxylamine or one of its salts in a solvent such as methanol, ethanol, pyridine, etc. in the presence or absence of a base such as Na$_2$CO$_3$, K$_2$CO$_3$, triethylamine, KOtBu, etc. (Lit.: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292).

HOOC-Pyridine$^2$   Structure 5

A compound of Structure 4 may be prepared from a compound of Structure 5. Methods that effect the transformation of a compound of Structure 4 into a compound of Structure 5, or the opposite, are known to a person skilled in the art.

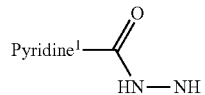

Structure 6

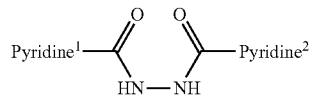

Structure 7

Compounds of Formula (I) which represent a [1,3,4]oxadiazole or [1,3,4]thiadiazole derivative are prepared similarly by reacting a compound of Structure 2 with hydrazine (by using a coupling reagent such as TBTU, DCC, EDC, HBTU, PyBOP, HOBt, CDI, etc.) to form a compound of Structure 6 which is then coupled with a compound of Structure 5 to give a compound of Structure 7. A compound of Structure 7 can also be prepared by following the reverse reaction order i.e. by first coupling a compound of Structure 5 with hydrazine followed by reacting the corresponding hydrazide intermediate with a compound of Structure 2. Dehydration of a compound of Structure 7 to form the desired [1,3,4]oxadiazole derivative is affected by treating a compound of Structure 7 with a reagent such as POCl$_3$, CCl$_4$ or CBr$_4$ in combination with triphenylphosphine, P$_2$O$_5$, Burgess reagent, etc. in a solvent such as toluene, acetonitrile, dioxane, THF, CHCl$_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075; C. T. Brain, J. M. Paul, Y. Loong, P. J. Oakley, *Tetrahedron Lett.* 40 (1999) 3275-3278). Likewise, [1,3,4]thiadiazole derivatives are obtained by cyclising a compound of Structure 7 with Lawesson's reagent optionally in combination with P$_2$S$_5$ in the presence or absence of a solvent such as pyridine, toluene, THF, acetonitrile, etc. at elevated temperatures with or without microwave irradiation (Lit.: e.g. A. A. Kiryanov, P. Sampson, A. J. Seed, *J. Org. Chem.* 66 (2001) 7925-7929; *Org. Prep. Proc. Int.* 37 (2005) 213-222).

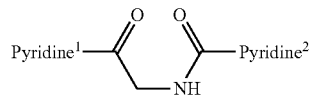

Structure 8

Compounds of Formula (I) which represent an oxazole or a thiazole derivative are prepared by treating a compound of Structure 8 either with POCl$_3$, PCl$_5$, I$_2$ in combination with triphenylphosphine and triethylamine, trifluoracetic anhydride, Burgess reagent, etc. in a solvent such as toluene, benzene, dioxane, THF, etc. at temperatures between 20 and 120° C., or with Lawesson's reagent, optionally in combination with P$_2$S$_5$, in the presence or absence of a solvent such as pyridine, toluene, THF, acetonitrile, etc. at elevated temperatures with or without microwave irradiation as mentioned above (Lit.: e.g. N. Sato, T. Shibata, M. Jitsuoka, T. Ohno, T. Takahashi, T. Hirohashi, T. Kanno, H. Iwaasa, A. Kanatani, T. Fukami, *Bioorg. & Med. Chem. Lett.* 14 (2004) 1761-1764).

The compounds of Structure 8 are prepared by reacting a compound of Structure 9 with a compound of Structure 5. The aminoketon of Structure 9 can be prepared from a compound of Structure 2 by procedures given in the literature (e.g. J. L. LaMattina, *J. Heterocyclic Chem.* 20 (1983) 533-538; M. Pesson, M. Antoine, P. Girard, J. L. Benichon, S. Chabassier, P. De Lajudie, S. Patte, F. Roquet, G. Montay, *Eur. J. Med. Chem.* 15 (1980) 263-268).

Structure 9

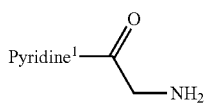

Alternatively, the bonds between the pyridine or the phenylring and the central 5-membered heteroaromatic ring can also be formed by applying palladium catalysed cross coupling reactions.

Depending on the nature of the functionalities present in the residues $R^1$, $R^3$, $R^5$, $R^6$, $R^{11}$, $R^{13}$, $R^{15}$, and $R^{16}$, these functionalities may require temporary protection.

Appropriate protecting groups are known to a person skilled in the art and include e.g. a benzyl, a THP or a trialkyl-silyl group to protect an alcohol, or a BOO group to protect an amine, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994).

Compounds of Structure 2, wherein Pyridine$^1$ represents

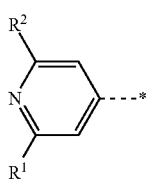

may be prepared by reacting a 2,6-dichloro-isonicotinic acid ester (Structure 10, below) with an alkyl Grignard reagent in the presence of Fe(acac)$_3$ in a solvent such as THF, dioxane, DMF, NMP, etc., or combinations thereof, at temperatures ranging from –78 to 25° C. (Fürstner conditions, Lit.: e.g. A. Fürstner, A. Leitner, M. Mendez, H. Krause *J. Am. Chem. Soc.* 124 (2002) 13856-13863; A. Fürstner, A. Leitner, *Angew. Chem.* 114 (2002) 632-635). The reaction conditions can be chosen such that either the 2-chloro-6-alkyl-isonicotinic acid ester or the 2,6-dialkyl-isonicotinic acid ester is obtained as the main product. The two chlorine atoms in a 2,6-dichloro-isonicotinic acid ester may also be substituted either sequentially or in one step by two alk-1-enyl groups, which may be the same or different, by treating 2,6-dichloro-isonicotinic acid ester with the appropriate alkenyl boron derivative under Suzuki coupling conditions known to a person skilled in the art. The obtained 2,6-di-alkenyl-isonicotinic acid ester is hydrogenated to the corresponding 2,6-dialkyl-isonicotinic acid ester. In addition, a procedure in which the Fürstner and the Suzuki conditions are employed sequentially can be envisaged. The 2,6-dichloro-isonicotinic acid esters or the 2-chloro-6-alkyl-isonicotinic acid esters may also be treated with an alcohol or an alcoholate at elevated temperatures to furnish the corresponding 2-chloro-6-alkoxy-isonicotinic acid esters or 2-alkoxy-6-alkyl-isonicotinic acid esters (Lit.: e.g. N. Wild, U. Groth, *Eur. J. Org. Chem.* 2003, 4445-4449). Finally, cleavage of the ester functionality delivers the compounds of Structure 2.

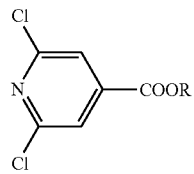

Structure 10

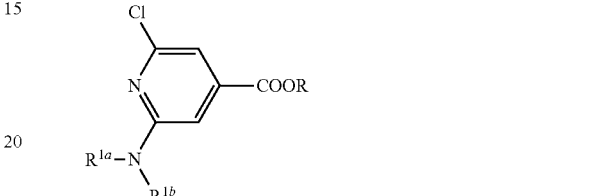

Structure 11

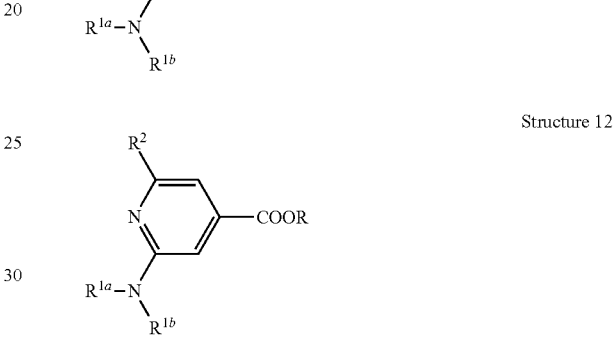

Structure 12

Compounds of the above Structure 2 wherein $R^1$ represents $NR^{1a}R^{1b}$ may be prepared by reacting a 2,6-dichloro-isonicotinic acid ester (Structure 10, wherein R represents a $C_{1-4}$-alkyl, preferably an isopropyl or a tert.-butyl group) with the appropriate amine $NHR^{1a}R^{2b}$ in the presence or absence of an additional solvent such as THF, dioxane, ethanol, etc., preferably at temperatures above 50° C. to give a compound of Structure 11. The compounds of Structure 11 can then be reacted with the appropriate alkyl-Zn reagent (e.g. Me$_2$Zn, MeZnCl, Et$_2$Zn, etc.) under Negishi reaction conditions (Lit.: e.g. H. Matsushita, E. Negishi, *J. Org. Chem.* 47 (1982) 4161-4165) to give a compound of Structure 12, which can be hydrolysed to a compound of Structure 2. In addition, compounds of the Structure 12 may be prepared by reacting a compound of Structure 11 with an alkyl Grignard reagent in the presence of Fe(acac)$_3$ in a solvent such as THF, dioxane, DMF, NMP, etc., or combinations thereof, at temperatures ranging from –78 to 25° C. (Fürstner conditions, see above). In case $R^2$ represents a $C_{2-4}$-alkyl group, the corresponding compounds of Structure 12 can also be prepared by reacting a compound of Structure 11 with an alkenyl boron derivative (e.g. 2,4,6-trivinyl-cyclotriboroxane) under Suzuki conditions (Lit.: e.g. F. Kerins, D. F. O'Shea, *J. Org. Chem.* 67 (2002) 4968-4971). The obtained 2-amino-6-alkenyl-isonicotinic acid derivative is hydrogenated to the corresponding compound of Structure 12.

Compounds of Structure 2, wherein $R^2$ represents a methoxy group can be prepared in analogy to the pathway outlined above from commercially available 2-chloro-6-methoxy-pyridine-4-carboxylic acid by introducing the desired $C_{1-5}$-alkyl or $C_{3-6}$-cycloalkyl residue for $R^1$ under either Negishi, Fürstner or Suzuki conditions.

Structure 13

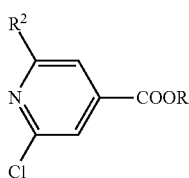

Alternatively, the compounds of Structure 12 may also be prepared by reacting a compound of Structure 13 with the appropriate amine $NHR^{1a}R^{1b}$ under Buchwald-Hartwig conditions (Lit.: e.g. J. P. Wolfe, H. Tomori, J. P. Sadighi, J. Yin, S. L. Buchwald, *J. Org. Chem.* 65 (2000) 1158-1174; S. Wagaw, S. L. Buchwald, *J. Org. Chem.* 61 (1996) 7240-7241; M. C. Harris, O. Geis, S. L. Buchwald, *J. Org. Chem.* 64 (1999) 6019-6022; S. R. Stauffer, S. Lee, J. P. Stambuli, S. I. Hauck, J. F. Hartwig, *Org. Letters* 2 (2000) 1423-1426). Compounds of Structure 13 or their corresponding acids are either commercially available or may be prepared by reacting a 2,6-dichloro-isonicotinic acid ester (Structure 10) with an alkyl Grignard reagent under Fürstner conditions (see above) or with an alkyl-Zn reagent under Negishi conditions. Reacting a compound of Structure 10 with an alkenyl boron derivative under Suzuki conditions, treating the corresponding alkenyl-chloro-isonicotinic acid ester with an amine $NHR^{1a}R^{1b}$ under Buchwald-Hartwig conditions and subsequent hydrogenation may also give access to compounds of Structure 12. The residues $R^{1a}$ and $R^{1b}$ may also be introduced by sequential alkylation and/or reductive amination of a compound of Structure 14 (Lit.: e.g. N. Finch, T. R. Campbell, C. W. Gemenden, H. J. Povalski, *J. Med. Chem.* 23 (1980) 1405-1410) which may be prepared by reacting a compound of Structure 13 with ammonia in a solvent such as water, methanol, ethanol, THF, etc. at elevated temperatures.

Structure 14

Structure 15

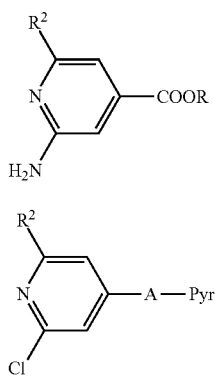

In case $R^{1b}$ represents hydrogen, the corresponding pyridine derivatives that may occur in the course of the synthesis of compounds of Formula (I), may require temporary protection at the secondary amine function.

Compounds of Structure 2 and Structure 5 that represent an isonicotinic acid wherein $R^1$ and $R^{11}$ represent hydroxymethyl, respectively, may be prepared from a corresponding 2-alkyl-isonicotinic acid ester (e.g. methyl ester) using the Minisci reaction (Lit.: e.g. R. B. Katz, J. Mistry, M. B. Mitchell, *Synth. Commun.* 19 (1989) 317-325; M. A. A. Biyouki, R. A. J. Smith, J. J. Bedford, J. P. Leader, *Synth. Commun.* 28 (1998) 3817-3825). Compounds of Structure 2 and 5 wherein $R^2$ and $R^{12}$ represent a methyl group and $R^1$ and $R^{11}$ represent hydroxymethyl, respectively, may also be prepared by making use of the Boeckelheide reaction (Lit.: e.g. N. C. Habermehl, P. M. Angus, M. L. Kilah, L. Noren, A. D. Rae, A. C. Willis, S. B. Wild, *Inorg. Chem.* 45 (2006) 1445-1462).

The above described reaction sequences that allow the introduction of the two residues $R^1$ and $R^2$ may also be applied to a compound in which the scaffold has already been further elaborated. For instance, the Buchwald reaction may also be applied to a compound of Structure 15.

Compounds of the Structure 2 wherein $Pyridine^1$ represents

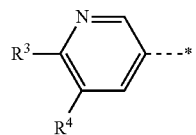

may be prepared by reacting a 5,6-dichloronicotinic acid ester with an alkyl Grignard reagent in the presence of $Fe(acac)_3$ in a solvent such as THF, dioxane, DMF, NMP, etc., or combinations thereof, at temperatures ranging from −78 to 25° C. (Fürstner conditions, Lit.: e.g. A. Fürstner, A. Leitner, M. Mendez, H. Krause, *J. Am. Chem. Soc.* 124 (2002) 13856-13863; A. Fürstner, A. Leitner, *Angew. Chem.* 114 (2002) 632-635). The reaction conditions can be chosen such that either the 5-chloro-6-alkyl-nicotinic acid ester or the 5,6-dialkyl-nicotinic acid ester is obtained as the main product. The two chlorine atoms in a 5,6-dichloronicotinic acid ester may also be substituted either sequentially or in one step by two alk-1-enyl groups, which may be the same or different, by treating 5,6-dichloronicotinic acid ester with the appropriate alkenyl boron derivative under Suzuki coupling conditions known to a person skilled in the art. The obtained 5,6-dialkenyl-nicotinic acid ester is hydrogenated to the corresponding 5,6-dialkyl-nicotinic acid ester. In addition, a procedure in which the Fürstner and the Suzuki conditions are employed sequentially can be envisaged. Furthermore, chloronicotinic acids may also be transformed to the corresponding alkylnicotinic acid using the Negishi reaction (see above). The 5,6-dichloronicotinic acid ester may also be treated with an alcohol or an alcoholate at elevated temperatures to furnish the corresponding 5-chloro-6-alkoxy-nicotinic acid esters. Finally, cleavage of the ester functionality delivers the compounds of Structure 2.

Alternatively, compounds of Structure 2, wherein $R^4$ represents a methyl group, can be prepared from a compound of Structure 16 via formation of the corresponding 6-chloro-5-methyl-nicotinic acid esters using methods well known in the art, followed by derivatisation using Fürstner or Suzuki conditions as described above and subsequent cleavage of the ester function. The compound of Structure 16 can be prepared from known 6-chloro-3-formyl-5-methyl-pyridine (Lit.: e.g. EP-0702003 or as described herein) by oxidation of the formyl group to the carboxylic acid using oxidation reagents well known in the art such as aq. $H_2O_2$ in formic acid, $KMnO_4$, etc. in the presence or absence of a solvent such as toluene, THF, acetonitrile, acetone, etc. at temperatures between 0 and 120° C. The corresponding nitrile of Structure 4, wherein $R^{12}$ represents a methyl group, can be prepared according to literature methods (Lit.: e.g. J. B. Paine III, *J. Heterocyclic Chem.* 1987, 351-355).

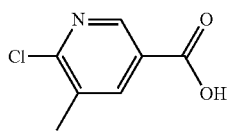

Structure 16

Compounds of Structure 5 are prepared in an analogous fashion.

Compounds of Structure 2 wherein Pyridine[1] represents

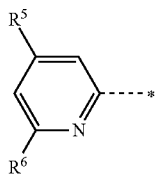

(Structure 17) may be prepared following the reaction sequence outlined below:

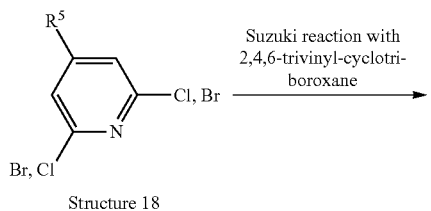

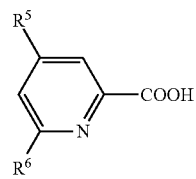

Structure 17

The picolinic acid of Structure 17 may be prepared by treating a compound of Structure 18 (either commercially available or prepared in analogy to literature procedures e.g. T. Kaminski, P. Gros, Y. Fort, *Eur. J. Org. Chem.* 19 (2003) 3855-3860; U. Ziener, E. Breuning, J.-M. Lehn, E. Wegelius, K. Rissanen, G. Baum, D. Fenske, G. Vaughan, *Chemistry-A European Journal* 6 (2000) 4132-4139; R.-A. Fallahpour, *Synthesis* 2000 1665-1667) with 2,4,6-trivinyl-cyclotriboroxane under Suzuki conditions to form a compound of Structure 19 which is oxidised and esterified to the picolinic acid of Structure 20. Oxidation of a commercially available compound of Structure 21 may also give access to a compound of Structure 20. The compound of Structure 20 is then either subjected to Suzuki cross coupling conditions using the appropriate 2,4,6-trialkenyl-cyclotriboroxane (prepared according to F. Kerins, D. F. O'Shea, *J. Org. Chem.* 67 (2002) 4968-4971), hydrogenated and saponified, or treated with the appropriate alkyl-Zn-reagent under Negishi conditions prior to saponification to furnish the desired compound of Structure 17.

Compounds of the Structure 2 wherein Pyridine[1] represents

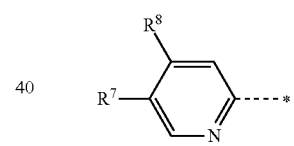

(Structure 22 or Structure 27) may be prepared following the reaction sequence outlined below:

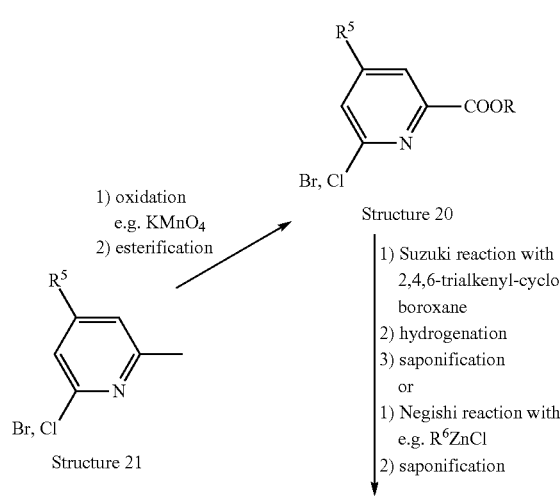

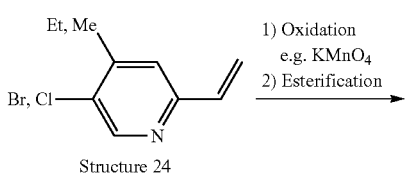

-continued

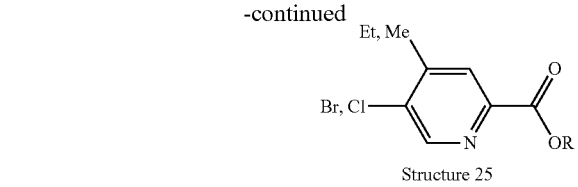
Structure 25

1) Suzuki reaction with 2,4,6-trialkenyl-cyclotriboroxane
2) hydrogenation
or
1) Negishi reaction with e.g. R⁷ZnCl

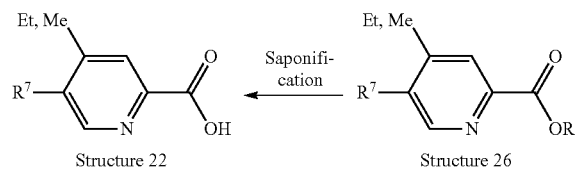
Structure 22 ← Saponification ← Structure 26

Thus, a compound of Structure 23 (commercially available or may be prepared in analogy to literature procedures, e.g. P. Pierrat, P. Gros, Y. Fort, *Synlett* 2004, 2319-2322) is reacted with 2,4,6-trivinyl-cyclotriboroxane under Suzuki conditions to form a compound of Structure 24, which is oxidised and esterified to a compound of Structure 25. Suzuki reaction with the appropriate 2,4,6-trialkenyl-cyclotriboroxane, hydrogenation and saponification or Negishi reaction with the appropriate alkyl-Zn-reagent followed by saponification of a compound of Structure 26 furnish the compounds of Structure 22.

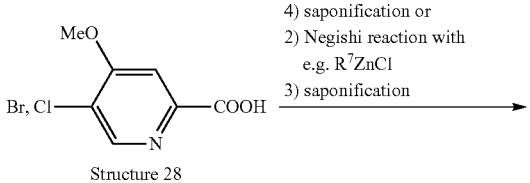
Structure 28

1) esterification
2) Suzuki reaction with 2,4,6-trialkenyl-cyclotriboroxane
3) hydrogenation
4) saponification or
2) Negishi reaction with e.g. R⁷ZnCl
3) saponification

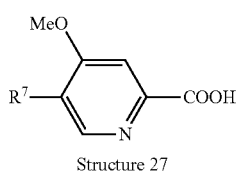
Structure 27

Analogously, by applying the reaction sequence of either esterification, Suzuki reaction, hydrogenation, saponification or esterification, Negishi reaction and saponification, a commercially available compound of Structure 28 may be transformed into a compound of Structure 27.

Compounds of Structure 2 wherein Pyridine¹ represents

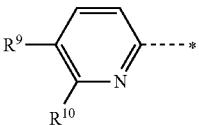

(Structure 33) may be prepared following the reaction sequence outlined below:

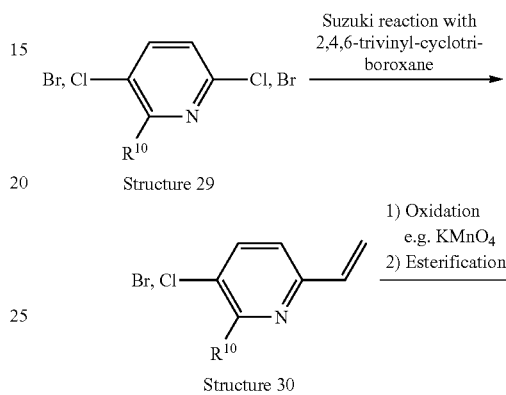
Structure 29

Suzuki reaction with 2,4,6-trivinyl-cyclotriboroxane →

Structure 30

1) Oxidation e.g. KMnO₄
2) Esterification →

Structure 31

1) Suzuki reaction with 2,4,6-trialkenyl-cyclotriboroxane
2) hydrogenation
or
1) Negishi reaction with e.g. R⁹ZnCl

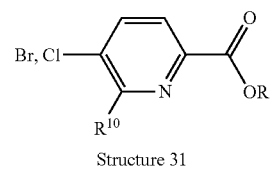
Structure 33 ← Saponification ← Structure 32

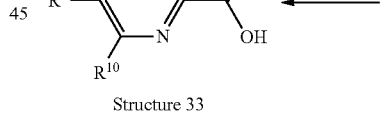

Thus, a compound of Structure 29 is treated with 2,4,6-trivinyl-cyclotriboroxane under Suzuki conditions to give a compound of Structure 30. Oxidation followed by saponification gives the corresponding compound of Structure 31. Suzuki reaction with the appropriate 2,4,6-trialkenyl-cyclotriboroxane, hydrogenation and saponification or Negishi reaction with the appropriate alkyl-Zn-reagent followed by saponification furnishes the desired compounds of Structure 33. Compounds of Structure 29, wherein R¹⁰ represents a methyl group are commercially available. Compounds of Structure 29, wherein R¹⁰ represents an ethyl group can be prepared following literature procedures (e.g. T. Hanazawa, M. Hirano, T. Inoue, K. Nakao, Y. Shishido, H. Tanaka; WO 2006/097817 (Pfizer Japan Inc.), p 84; S. R. Natarajan et al. *Bioorg. Med. Chem. Lett.* 13 (2003) 273-276), for instance from commercially available 3-amino-2,6-dichloropyridine as outlined below:

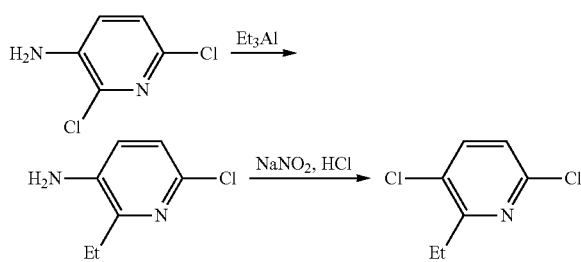

In general, the desired residues $R^1$ to $R^{20}$ may also be introduced in later steps that follow establishing of the Pyridine$^1$-A-Pyridine$^2$ scaffold.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

EXAMPLES

The following examples illustrate the invention but do not at all limit the scope thereof.

All temperatures are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 µm, 120 Å, gradient: 5-95% acetonitrile in water, 1 min, with 0.04% trifluoroacetic acid, flow: 4.5 mL/min), $t_R$ is given in min, LC-MS* denotes basic LC-conditions, i.e. eluting with a gradient of 5-95% acetonitrile in water containing 0.5% of sat. aq. NH$_4$OH solution, otherwise identical conditions; by TLC (TLC-plates from Merck, Silica gel 60 F$_{254}$); or by melting point. Compounds are purified by preparative HPLC (column: X-terra RP18, 50×19 mm, 5 µm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol). Racemates can be separated into their enantiomers by preparative HPLC (column: ChiralPaK AD 20×250 mm, 5 µm, 15% ethanol in hexane).

ABBREVIATIONS (AS USED HEREIN)

aq. aqueous
atm atmosphere
BOC tert-butoxycarbonyl
BSA bovine serum albumin
Bu butyl
CC column chromatography
CDI carbonyl diimidazole
dba dibenzylidene acetone
DCC dicyclohexyl carbodiimide
DCM dichloromethane
DEAD diethyl azodicarboxylate
DIPEA diisopropyl-ethylamine, Hünig's base, ethyl-diisopropylamine
DME 1,2-dimethoxyethane
DMF dimethylformamide
DMSO dimethylsulfoxide
dppf 1,1'-bis(diphenylphosphino-κP)ferrocene
EA ethyl acetate
EDC N-(3-dimethylaminopropyl)-N'-ethyl-carbodiimide
eq. equivalent(s)
Et ethyl
EtOH ethanol
Ex. example(s)
FC flash chromatography
Fe(acac)$_3$ iron(III) acetylacetone-complex
h hour(s)
HBTU O-(benzotriazol-1-yl)-N,N,N',N'-tetramethyluronium hexafluorophosphate
HOBt 1-hydroxybenzotriazole
HPLC high performance liquid chromatography
HV high vacuum conditions
KOtBu potassium tert-butoxide
LC-MS liquid chromatography-mass spectrometry
Lit. literature
Me methyl
MeOH methanol
min minute(s)
MPLC medium pressure liquid chromatography
NaOAc sodium acetate
NMP N-methylpyrrolidin-2-one
OAc acetate
org. organic
Ph phenyl
PyBOP benzotriazol-1-yl-oxy-tris-pyrrolidino-phosphonium-hexafluoro-phosphate
prep. preparative
rt room temperature
sat. saturated
S1P sphingosine 1-phosphate
TBTU 2-(1H-benzotriazole-1-yl)-1,2,3,3-tetramethyluronium tetrafluoroborate
TFA trifluoroacetic acid
THF tetrahydrofuran
THP tetrahydropyran
TLC thin layer chromatography
$t_R$ retention time
Xantphos 4,5-bis(diphenylphosphino)-9,9-dimethylxanthene 2-Isobutyl-isonicotinic acid

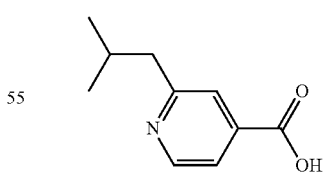

To a solution of 2-chloro-pyridine-4-carboxylic acid (2.55 g, 16.2 mmol) in dioxane (50 mL), Pd(dppf) (132 mg, 0.162 mmol) is added. The mixture is stirred under argon at rt and isobutyl zinbromide (6.55 g, 32.4 mmol, 65 mL of a 0.5 M solution in THF) is added dropwise. The mixture is stirred at rt for 1 h, then at 100° C. for 16 h. The mixture is cooled to rt and diluted with EA (250 mL) and cold water (0° C.). The mixture is acidified by adding aq. 25% HCl. The org. phase is separated and the aq. phase is extracted with EA (4×50 mL) followed by DCM (6×50 mL). The combined org. extracts are concentrated and dried. The crude product is purified by MPLC on silica gel to give the title compound (2.0 g) in form of a pale yellow oil. LC-MS: $t_R$=0.47 min, $[M+1]^+$=180.09. $^1$H NMR (CD$_3$OD): δ 1.03 (d, J=6.8 Hz, 6H), 2.12-2.24 (m, 1H), 3.00 (d, J=7.3 Hz, 2H), 8.29 (dd, J=5.8, 1.5 Hz, 1H), 8.34 (s, 1H), 8.88 (d, J=5.8 Hz, 1H).

2,6-Dimethylisonicotinic acid

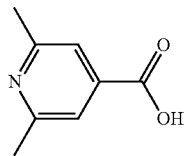

a) To a solution of 2,6-dichloro-isonicotinic acid tert.-butyl ester (3.35 g, 13.5 mmol), Fe(acac)$_3$ (512 mg, 1.45 mmol) and NMP (1.58 g, 16.0 mmol) in THF (400 mL), a solution of methylmagnesium iodide (11.67 g, 70.2 mmol) in THF is slowly added at −77° C. The brown solution turns green-grey. After the addition of about half of the Grignard reagent the dark brown suspension is warmed to rt and stirred for 30 min before it is again cooled to −70° C. The other half of the Grignard reagent is added, the mixture turns dark green-brown and is warmed to rt and stirred for 16 h. The mixture is cooled to −50° C. and another portion of the Grignard reagent (2.24 g, 13.5 mmol) is added. The reaction mixture is warmed to rt, stirred for 16 h and then carefully quenched with 1 N aq. HCl (100 mL) and diluted with diethyl ether. The org. layer is separated and the aq. phase is extracted with diethyl ether. The combined org. extracts are dried over MgSO$_4$, filtered and evaporated. The crude product is purified by MPLC on silica gel to give 2,6-dimethylisonicotinic acid tert.-butyl ester (2.37 g) as a pale yellow oil; LC-MS: $t_R$=0.65 min, $[M+1]^+$=208.29.

b) A solution of 2,6-dimethylisonicotinic acid tert.-butyl ester (2.37 g, 11.44 mmol) in 5 N HCl in isopropanol (40 mL) is stirred at 80° C. for 3 h. The solvent is evaporated and the crude product is purified by MPLC on silica gel (heptane:EA gradient) to give 2,6-dimethylisonicotinic acid hydrochloride as a beige resin; $^1$H NMR (CD$_3$OD): δ 8.16 (s, 2H), 2.84 (s, 6H).

2-Hydroxymethyl-6-methyl-isonicotinic acid

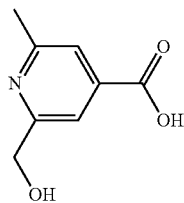

a) To a solution of 2-methyl-isonicotinic acid (5.0 g, 36.40 mmol) in methanol (100 mL), H$_2$SO$_4$ (2 mL) is added. The mixture is refluxed for 72 h before a solution of ammonium peroxydisulfate (16.64 g, 72.9 mmol) in water (15 mL) is added. The mixture boils vigorously. Stirring is continued at 65° C. for 24 h before another portion of ammonium peroxydisulfate is added. Stirring is continued at 65° C. for 24 h. About ⅔ of the solvent is evaporated, the remaining solution is neutralised with 1 N aq. NaOH and extracted five times with DCM. The combined org. extracts are dried over MgSO$_4$, filtered and concentrated to give 2-hydroxymethyl-6-methyl-isonicotinic acid methyl ester (3.71 g) as a yellow solid; LC-MS: $t_R$=0.44 min, $[M+1]^+$=182.05.

b) A solution of 2-hydroxymethyl-6-methyl-isonicotinic acid methyl ester (500 mg, 2.76 mmol) in 32% aq. HCl (10 mL) is stirred at 60° C. for 5 h. The solvent is removed and the residue is dried to give 2-hydroxymethyl-6-methyl-isonicotinic acid hydrochloride (480 mg) as a yellow solid; LC-MS: $t_R$=0.15 min, $[M+1]^+$=168.04.

2-Ethyl-6-methylisonicotinic acid

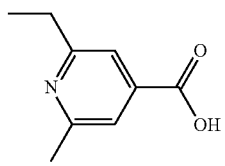

a) A suspension of 2-chloro-6-methyl-isonicotinic acid (7.0 g, 40.9 mmol) in toluene (100 mL) is heated to 80° C. and then slowly treated with N,N-dimethylformamide di-tert. butylacetal (21.2 g, 104.3 mmol). The mixture becomes clear. Heating and stirring is continued for 20 h before another portion N,N-dimethylformamide di-tert. butylacetal (8.32 g, 40.9 mmol) is added. Stirring is continued at 80° C. for 72 h. The reaction mixture is cooled to rt, diluted with diethyl ether and washed with sat. aq. Na$_2$CO$_3$-solution. The org. extract is dried over MgSO$_4$, filtered and the solvent is carefully evaporated. The crystalline material that forms is collected, carefully washed with cold heptane and dried to give 2-chloro-6-methyl-isonicotinic acid tert.-butyl ester (6.29 g) as colourless fine needles; LC-MS: $t_R$=1.01 min; $[M+1]^+$=228.11; $^1$H NMR (CDCl$_3$): δ 7.61 (s, 1H), 7.56 (s, 1H), 2.59 (s, 3H), 1.29 (s, 9H).

b) To a red solution of 2-chloro-6-methyl-isonicotinic acid tert.-butyl ester (2.95 g, 13.0 mmol), Fe(acac)$_3$ (512 mg, 1.45 mmol) and NMP (1.58 g, 16.0 mmol) in THF (400 mL), a solution of ethylmagnesium bromide (1.81 g, 13.6 mmol) in THF is slowly added at −77° C. The brown solution turns green-grey. The suspension is warmed to rt, stirred for 30 min before the yellow solution is again cooled to −70° C. and another portion of the Grignard reagent (1.38 g, 10.4 mmol) is added. The reaction mixture is warmed to rt, stirred for 16 h and then carefully quenched with 1 N aq. HCl (100 mL) and diluted with diethyl ether. The org. layer is separated and the aq. phase is extracted with diethyl ether. The combined org. extracts are dried over MgSO$_4$, filtered and evaporated. The crude product is purified by MPLC on silica gel to give 2-ethyl-6-methyl-isonicotinic acid tert.-butyl ester as a yellow oil which is dissolved in 4 N HCl in dioxane (50 mL). The solution is stirred at 50° C. for 16 h before the solvent is evaporated to give 2-ethyl-6-methylisonicotinic acid hydrochloride as a beige powder; LC-MS: $t_R$=0.28 min; [M+1]+=

166.25; $^1$H NMR (CDCl$_3$): δ 8.19 (s, 2H), 3.12 (q; J=7.6 Hz, 2H), 2.84 (s, 3H), 1.43 (t, J=7.6 Hz, 3H).

2-Propyl-6-methylisonicotinic acid

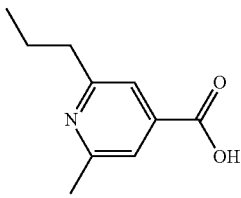

a) A solution of 2-chloro-6-methylisonicotinic acid (15.5 g, 90.3 mmol, 1 eq.) in ethanol (200 mL) and a few drops of concentrated sulfuric acid is stirred at 75° C. for 24 h. The solvent is evaporated and the residue is dissolved in ethyl acetate (200 mL) and washed with a solution of sat. aq. NaHCO$_3$ (70 mL) and water (2×70 mL). The org. extract is dried over MgSO$_4$, filtered and evaporated to give 2-chloro-6-methylisonicotinic acid ethyl ester (16.3 g) as a pink powder; LC-MS: t$_R$=0.92 min, [M+1]$^+$=200.17.

b) To a solution of 2-chloro-6-methylisonicotinic acid ethyl ester (2.0 g, 10.0 mmol), and trans-propenyl boronic acid (1.30 g, 15.13 mmol) in DME (20 mL), a solution of 2 M aq. K$_2$CO$_3$ (3 mL) followed by Pd(PPh$_3$)$_4$ (150 mg, 0.205 mmol) and triphenylphosphine (265 mg, 0.99 mmol) is added. The mixture is stirred at 100° C. for 15 h before it is cooled to rt, diluted with diethyl ether and washed with sat. aq. Na$_2$CO$_3$ (2×30 mL). The org. extract is dried over Na$_2$SO$_4$, filtered and evaporated. The crude product is purified by CC on silica gel eluting with heptane:EA 4:1 to give 2-propenyl-6-methylisonicotinic acid ethyl ester (2.25 g) as a colourless oil; LC-MS: t$_R$=0.65 min, [M+1]$^+$=206.33.

c) 2-propenyl-6-methylisonicotinic acid ethyl ester (2.25 g, 10.9 mmol) is dissolved in THF (100 mL), Pd/C (300 mg, 10% Pd) is added and the mixture is stirred under 1 atm H$_2$ at rt for 15 h. The catalyst is filtered off and the filtrate is evaporated to give 2-propyl-6-methylisonicotinic acid ethyl ester (2.30 g) as a colourless oil; LC-MS: t$_R$=0.65 min, [M+1]$^+$=208.12.

d) A solution of 2-propyl-6-methylisonicotinic acid ethyl ester (2.30 g, 11.0 mmol) in 6 N aq. HCl (40 mL) is stirred at 65° C. for 24 h before it is cooled to rt and extracted with diethyl ether (2×50 mL). The aq. phase is evaporated and the residue is dried under HV to give 2-propyl-6-methylisonicotinic acid hydrochloride (2.0 g) as a colourless solid, LC-MS: t$_R$=0.44 min; [M+1]$^+$=180.09; $^1$H NMR (D$_6$-DMSO): δ 8.02 (s, 1H), 7.99 (s, 1H), 3.04 (t, J=7.5 Hz, 2H), 2.78 (s, 3H), 1.82-1.72 (m, 2H), 0.93 (t, J=7.3 Hz, 3H).

2-Isopropyl-6-methyl-isonicotinic acid

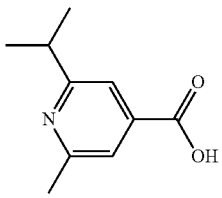

The title compound is prepared in analogy to 2-methyl-6-(2-methyl-propyl)-isonicotinic acid using 2,4,6-triisopropenyl-cyclotriboroxane; LC-MS: t$_R$=0.23 min; [M+1]$^+$=180.44.

2-Methyl-6-(2-methyl-propyl)-isonicotinic acid

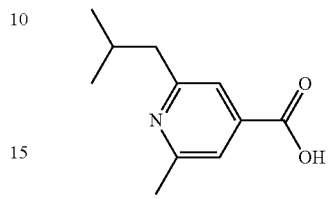

a) To a solution of 2-chloro-6-methylisonicotinic acid ethyl ester (9.92 g, 49.7 mmol), 2,4,6-tris-(2-methyl-propenyl)-cycloboroxane pyridine complex (13.0 g, 49.7 mmol, prepared in analogy to a procedure given by F. Kerins, D. F. O'Shea *J. Org. Chem.* 67 (2002) 4968-4971), and triphenylphosphine (1.39 g, 8.60 mmol) in DME (120 mL), a solution of 2 M aq. K$_2$CO$_3$ (40 mL) is added. The mixture is degassed and flushed with N$_2$ before Pd(PPh$_3$)$_4$ (580 mg, 0.793 mmol) is added. The mixture is stirred at 100° C. for 20 h before it is cooled to rt, diluted with EA and washed with sat. aq. NaHCO$_3$ (2×200 mL). The org. extract is dried over MgSO$_4$, filtered and evaporated. The crude product is purified by CC on silica gel eluting with heptane:EA 15:1 to give 2-methyl-6-(2-methyl-propenyl)-isonicotinic acid ethyl ester (9.90 g) as a yellow oil; LC-MS: t$_R$=0.44 min; $^1$H NMR (CDCl$_3$): δ 1.43 (m, 3H), 1.98 (s, 3H), 2.09 (s, 3H), 2.63 (s, 3H), 4.34-4.46 (m, 2H), 6.39 (s, 1H), 7.50 (s, 1H), 7.56 (s, 1H).

b) 2-Methyl-6-(2-methyl-propenyl)-isonicotinic acid ethyl ester (9.90 g, 45.2 mmol) is dissolved in THF (100 mL) and methanol (100 mL), Pd/C (800 mg, 10% Pd) is added and the mixture is stirred under 1 atm H$_2$ at rt for 5 h. The catalyst is filtered off and the filtrate is evaporated. The crude product is purified by CC on silica gel eluting with hexane:EA 1:1 to give 2-methyl-6-(2-methyl-propyl)-isonicotinic acid ethyl ester (9.78 g) as a colourless oil; LC-MS: t$_R$=0.71 min.

c) A solution of 2-methyl-6-(2-methyl-propyl)-isonicotinic acid ethyl ester (9.78 g, 45.1 mmol) in 6 N aq. HCl (20 mL) is stirred at 95° C. for 20 h before the solvent is evaporated. The residue is dried under HV to give 2-methyl-6-(2-methyl-propyl)-isonicotinic acid hydrochloride (9.56 g) as a colourless solid, LC-MS: t$_R$=0.52 min.

2-Hydroxymethyl-6-isobutyl-isonicotinic acid

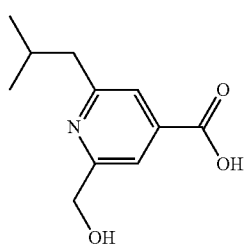

a) To a solution of 2-chloro-isonicotinic acid ethyl ester (10.0 g, 63.3 mmol) in THF (150 mL), NMP (8.78 g, 88.6 mmol) and Fe(acac)₃ (2.46 g, 6.96 mmol) is added under argon. The mixture is cooled to −74° C. before isobutylmagnesium bromide (47 mL of a 2 M solution in THF, 94.9 mmol) is added. The temperature rises to −65° C. The mixture is stirred at −75° C. for 1 h, then warmed to rt and carefully quenched with water. The mixture is extracted with EA, the org. extract is dried over MgSO₄, filtered and concentrated. The crude product is purified by CC on silica gel eluting with heptane:EA 9:1 to give 2-isobutyl-isonicotinic acid ethyl ester (3.00 g) as an oil, LC-MS: $t_R$=0.74 min, $[M+1]^+$= 208.11.

b) A solution of 2-isobutyl-isonicotinic acid ethyl ester (1.00 g, 4.83 mmol) in methanol (50 mL) and H₂SO₄ (0.3 mL) is heated to 80° C. before a solution of ammonium peroxydisulfate (2.20 g, 9.65 mmol) in water (1.5 mL) is added carefully. Stirring is continued for 1 h at 80° C. before another portion of ammonium peroxydisulfate (2.20 g, 9.65 mmol) in water (1.5 mL) is added. The mixture is refluxed over night, cooled to rt, diluted with EA and washed with sat. aq. NaHCO₃ solution. The org. extract is dried over MgSO₄, filtered and concentrated. The crude product is purified by CC on silica gel eluting with DCM containing 10% of methanol to give 2-hydroxymethyl-6-isobutyl-isonicotinic acid ethyl ester (560 mg) as an oil; LC-MS: $t_R$=0.81 min, $[M+1]^+$= 238.40.

c) A solution of 2-hydroxymethyl-6-isobutyl-isonicotinic acid ethyl ester (100 mg, 0.421 mmol) in 25% aq. HCl (5 mL) is stirred at 75° C. for 16 h. The solvent is removed in vacuo and the remaining residue is dried under HV to give 2-hydroxymethyl-6-isobutyl-isonicotinic acid hydrochloride (100 mg) as an oil; LC-MS: $t_R$=0.52 min, $[M+1]^+$=210.47.

2-(1-Ethyl-propyl)-6-methyl-isonicotinic acid)

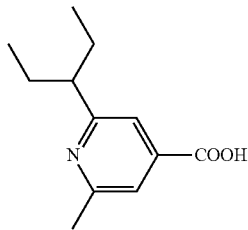

a) To a suspension of 2-chloro-6-methyl-isonicotinic acid (20.0 g, 117 mmol) in isopropanol (80 mL), H₂SO₄ (5 mL) is added dropwise. The mixture becomes warm (40° C.). The mixture is stirred for 24 h at rt, then at 90° C. for 28 h before the solvent is removed in vacuo. The residue is dissolved in diethyl ether (200 mL), washed with sat. aq. NaHCO₃-solution (3×50 mL) followed by brine (3×50 mL), dried over Na₂SO₄, filtered and concentrated to give 2-chloro-6-methyl-isonicotinic acid isopropyl ester (21.0 g) as a colourless oil which slowly crystallises; LC-MS: $t_R$=0.97 min, $[M+1]^+$= 214.05.

b) A a solution of 2-chloro-6-methyl-isonicotinic acid isopropyl ester (2.0 g, 9.36 mmol) in dioxane (75 mL) is degassed and put under argon before Pd(dppf) (229 mg, 0.281 mmol) is added. At rt, a 0.5 M solution of 1-ethyl-propylzinc bromide in THF (46.8 mL, 23.4 mmol) is added dropwise to the mixture. The mixture is stirred at 80° C. for 16 h before the reaction is quenched by adding ice-cold water (200 mL). A precipitate forms and the mixture is diluted with EA (200 mL) and filtered through celite. The filtrate is transferred into a separatory funnel. The org. phase is collected and the aq. phase is extracted with EA (120 mL). The combined org. extracts are dried over MgSO₄, filtered and concentrated. The crude product is purified by CC on silica gel eluting with heptane:EA 9:1 to 4:1 to give 2-(1-ethyl-propyl)-6-methyl-isonicotinic acid isopropyl ester (1.6 g) as a yellow oil; LC-MS: $t_R$=0.79 min, $[M+1]^+$=250.14; ¹H NMR (D₆-DMSO): δ 0.70 (t, J=7.3 Hz, 6H), 1.33 (d, J=6.3 Hz, 6H), 1.58-1.70 (m, 4H), 2.51 (s, 3H), 2.55-2.63 (m, 1H), 5.15 (hept, J=5.8 Hz), 7.39 (s, 1H), 7.49 (s, 1H).

c) A solution of 2-(1-ethyl-propyl)-6-methyl-isonicotinic acid isopropyl ester (1.54 g, 6.18 mmol) in 25% aq. HCl (60 mL) is stirred at 65° C. for 16 h. The solvent is removed in vacuo and the residue is dissolved in dioxane and concentrated again to give 2-(1-ethyl-propyl)-6-methyl-isonicotinic acid hydrochloride (1.70 g) as a brownish solid; LC-MS: $t_R$=0.62 min, $[M+1]^+$=208.52.

2-Cyclopentyl-6-methyl-isonicotinic acid

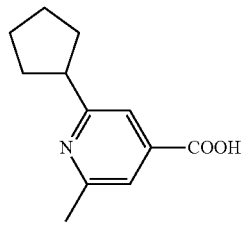

a) Under argon, Pd(dppf) (200 mg, 0.245 mmol) is added to a solution of 2-chloro-isonicotinic acid ethyl ester (4.80 g, 24.0 mmol) in dioxane (60 mL). A solution of cyclopentyl zink chloride (50 mL, 24.0 mmol, ~2 M solution in THF) is added dropwise. The mixture is stirred at 75° C. for 2 h before it is cooled to rt, carefully diluted with water and extracted twice with EA. The combined org. extracts are dried over MgSO₄, filtered and concentrated. The crude product is purified by CC on silica gel eluting with heptane:EA 9:1 to give 2-cyclopentyl-6-methyl-isonicotinic acid ethyl ester (3.96 g) as an oil; LC-MS: $t_R$=0.72 min, $[M+1]^+$=234.11.

b) A solution of 2-cyclopentyl-6-methyl-isonicotinic acid ethyl ester (3.96 g, 17.0 mmol) in 25% aq. HCl (50 mL) is stirred at 75° C. for 16 h. The solvent is removed in vacuo and the remaining residue is dried under HV to give 2-cyclopentyl-6-methyl-isonicotinic acid hydrochloride (4.12 mg) as a white solid; LC-MS: $t_R$=0.54 min, $[M+1]^+$=206.08.

2,6-Diethyl-isonicotinic acid

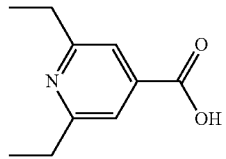

a) To a solution of 2,6-dichloro-isonicotinic acid tert.-butyl ester (780 mg, 3.14 mmol), and 2,4,6-trivinylcyclotriboroxane pyridine complex (640 mg, 2.66 mmol, prepared according to F. Kerins, D. F. O'Shea J. Org. Chem. 67 (2002) 4968-4971) in DME (12 mL), a solution of 2 M aq. K₂CO₃ (3 mL) followed by Pd(PPh₃)₄ (30 mg, 0.041 mmol) and triphenylphosphine (50 mg, 0.187 mmol) is added. The mixture is stirred at 100° C. for 15 h before it is cooled to rt, diluted with diethyl ether and washed with 1 N aq. NaOH solution (3×30 mL). The aq. phase is extracted once more with diethyl ether and the combined org. extracts are dried over Na$_2$SO$_4$, filtered and evaporated. The crude product is purified by CC on silica gel eluting with heptane:EA 5:1 to give 2,6-divinyl-isonicotinic acid tert-butyl ester (703 mg) as a colourless oil; LC-MS: t$_R$=1.03 min, [M+1]$^+$=232.01.

b) To a solution of 2,6-divinyl-isonicotinic acid tert-butyl ester (703 mg, 3.04 mmol) in methanol (15 mL), Pd/C (50 mg, 10% Pd) is added and the mixture is stirred under 1 atm of H$_2$ at rt for 15 h. The catalyst is filtered off and the filtrate is evaporated. The remaining residue is purified by CC on silica gel eluting with heptane:EA 5:1 to give 2,6-diethyl-isonicotinic acid tert-butyl ester (635 mg) as a colourless oil; LC-MS: t$_R$=1.05 min, [M+1]$^+$=236.13.

c) A solution of 2,6-diethyl-isonicotinic acid tert-butyl ester (635 mg, 2.70 mmol) in 6 N aq. HCl (10 mL) is stirred at 95° C. for 15 h before the solvent is evaporated. The residue is dried under HV to give 2,6-diethyl-isonicotinic acid hydrochloride (523 mg) as a colourless solid, LC-MS: t$_R$=0.42 min; [M+1]$^+$=180.31; $^1$H NMR (D$_6$-DMSO): δ 7.95 (s, 2H), 3.05 (q, J=7.5 Hz, 4H), 1.31 (t, J=7.5 Hz, 6H).

2,6-Diisobutyl-isonicotinic acid

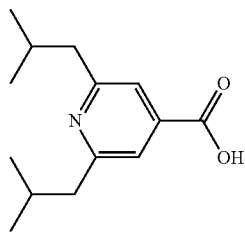 [SMILES: CC(C)Cc1cc(C(=O)O)cc(CC(C)C)n1]

2,6-Diisobutyl-isonicotinic acid hydrochloride is prepared starting from 2,6-dichloro-isonicotinic acid tert.-butyl ester and 2,4,6-tri-(2-methyl-propenyl)-cycloboroxane pyridine complex in analogy to 2,6-diethyl-isonicotinic acid; LC-MS: t$_R$=0.68 min; [M+1]$^+$=236.40; $^1$H NMR (D$_6$-DMSO): δ 7.90 (s, 2H), 2.92 (d, J=6.3 Hz, 4H), 2.10 (hept, J=6.8 Hz, 2H), 0.90 (t, J=6.5 Hz, 6H).

2-Ethyl-6-isobutyl-isonicotinic acid

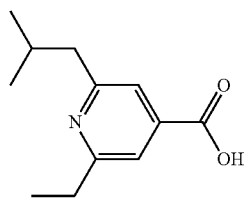

a) To a solution of 2,6-dichloro-isonicotinic acid tert.-butyl ester (500 mg, 2.02 mmol), and 2,4,6-trivinylcyclotriboroxane pyridine complex (170 mg, 0.706 mmol) in DME (12 mL), a solution of 2 M aq. K$_2$CO$_3$ (3 mL) followed by Pd(PPh$_3$)$_4$ (30 mg, 0.041 mmol) and triphenylphosphine (50 mg, 0.187 mmol) is added. The mixture is stirred at 45° C. for 15 h. 2,4,6-Tri-(2-methyl-propenyl)-cycloboroxane pyridine complex (594 mg, 1.83 mmol) is then added to the mixture and stirring is continued at 100° C. for 15 h. The mixture is cooled to rt, diluted with 1 N aq. NaOH solution and extracted twice with diethyl ether. The org. extracts are washed with 1 N aq. NaOH solution (2×30 mL), and brine, dried over Na$_2$SO$_4$, filtered and evaporated. The remaining residue is purified by CC on silica gel eluting with heptane:EA 5:1 to give 2-(2-methyl-propenyl)-6-vinyl-isonicotinic acid tert-butyl ester (780 mg) as a colourless oil containing 2,6-di-(2-methyl-propenyl)-isonicotinic acid tert.-butyl ester as impurity; LC-MS: t$_R$=1.01 min, [M+1]$^+$=260.14.

b) To a solution of the above 2-(2-methyl-propenyl)-6-vinyl-isonicotinic acid tert-butyl ester (444 mg, 1.71 mmol) in methanol (15 mL), Pd/C (50 mg, 10% Pd) is added and the mixture is stirred under 1 atm of H$_2$ at rt for 15 h. The catalyst is filtered off and the filtrate is evaporated. The remaining residue is purified by CC on silica gel eluting with heptane: EA 5:1 to give 2-ethyl-6-isobutyl-isonicotinic acid tert-butyl ester (391 mg) as a colourless oil; LC-MS: t$_R$=1.15 min, [M+1]$^+$=264.11.

c) A solution of 2-ethyl-6-isobutyl-isonicotinic acid tert-butyl ester (391 mg, 1.49 mmol) in 6 N aq. HCl (15 mL) is stirred at 65° C. for 2 days before the solvent is evaporated. The residue is dried under HV to give 2-ethyl-6-isobutyl-isonicotinic acid hydrochloride (334 mg) as a colourless solid, LC-MS: t$_R$=0.58 min, [M+1]$^+$=208.04.

2-Hydroxymethyl-6-methyl-isonicotinic acid

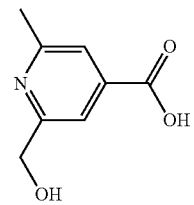

a) A suspension of 2-methyl-isoniconic acid (400 mg, 2.92 mmol) in methanol (50 mL) and H$_2$SO$_4$ (0.5 mL) is refluxed for 24 h. To the clear solution a solution of ammonium peroxidilsulfate ((NH$_4$)$_2$S$_2$O$_8$; 1.33 g, 5.83 mmol) in water (3 mL) is added and refluxing is continued for 1 h. Another portion of ammonium peroxidilsulfate ((NH$_4$)$_2$S$_2$O$_8$; 1.33 g, 5.83 mmol) in water (3 mL) is added and refluxing is continued for 3 h before a third portion of ammonium peroxidilsulfate ((NH$_4$)$_2$S$_2$O$_8$; 0.65 g, 2.91 mmol) in water (1.5 mL) is added. Refluxing is continued for 2 h, the mixture is cooled to rt and the methanol is removed under reduced pressure. The remaining mixture is diluted with sat. aq. NaHCO$_3$-solution (100 mL), extracted with EA (3×150 mL) and washed with sat. aq. NaHCO$_3$-solution (100 mL). The combined org. extracts are dried over MgSO$_4$, filtered, concentrated and briefly dried under HV to give 2-hydroxymethyl-6-methyl-isonicotinic acid methyl ester (400 mg) as a pale yellow solid; LC-MS: t$_R$=0.44 min, [M+1]$^+$=182.01; $^1$H NMR (CDCl$_3$): δ 2.65 (s, 3H), 3.69 (t, J=4.5 Hz, 1H), 3.97 (s, 3H), 4.81 (d, J=4.5 Hz, 2H), 7.63 (s, 1H), 7.64 (s, 1H).

b) A solution of 2-hydroxymethyl-6-methyl-isonicotinic acid methyl ester (500 mg, 2.76 mmol) in 32% aq. HCl (10 mL) is stirred at 60° C. for 5 h before it is evaporated and dried 2-Ethoxy-6-methyl-isonicotinic acid

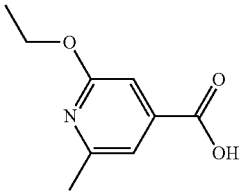

To a solution of K-tert.-butylate (1.99 g, 17.7 mmol) in ethanol (25 mL), 2-chloro-6-methyl-isonicotinic acid is added. The reaction mixture is stirred at 90° C. for 7 days. The mixture is cooled to rt, diluted with water and extracted with diethyl ether (3×50 mL). The aq. phase is acidified by adding 1 N aq. HCl and is then extracted three more times with diethyl ether (3×30 mL). The org. extracts are combined, dried over $Na_2SO_4$, filtered and concentrated. The crude product is purified by CC on silica gel eluting with heptane: EA 1:1 to give 2-ethoxy-6-methyl-isonicotinic acid (237 mg) as a white powder, LC-MS: $t_R$=0.60 min; $[M+1]^+$=182.24; $^1$H NMR ($CD_3OD$): δ 7.27 (s, 1H), 7.04 (s, 1H), 4.33 (q, J=7.0 Hz, 2H), 2.46 (s, 3H), 1.37 (t, J=7.0 Hz, 3H).

2-Isopropoxy-6-methyl-isonicotinic acid

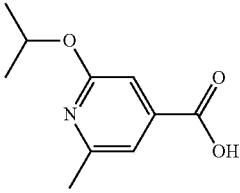

2-Isopropoxy-6-methyl-isonicotinic acid is prepared starting from 2-chloro-6-methyl-isonicotinic acid in analogy to 2-ethoxy-6-methyl-isonicotinic acid using isopropanol as solvent; LC-MS: $t_R$=0.70 min, $[M+1]^+$=196.04.

2-Isobutyl-6-methoxy-isonicotinic acid

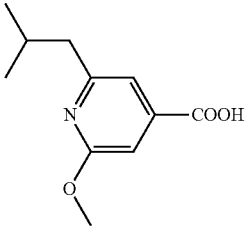

a) To a suspension of 2-chloro-6-methoxy-isonicotinic acid (2.00 g, 10.7 mmol) in methanol (100 mL), $H_2SO_4$ (2 mL) is added. The mixture is stirred at 65° C. for 20 h. The solution is cooled to rt. A precipitate forms. The solid material is collected, washed with methanol and dried to give 2-chloro-6-methoxy-isonicotinic acid methyl ester (1.66 g) as a white solid; LC-MS: $t_R$=1.29 min; $[M+1]^+$=202.00.

b) To a solution of 2-chloro-6-methoxy-isonicotinic acid methyl ester (1.66 g, 8.23 mmol) in dry THF (50 mL), Fe(acac)$_3$ (320 mg, 0.901 mmol) followed by NMP (1.1 mL, 11.5 mmol) is added. The mixture is cooled to −74° C. before a 2 M solution of isobutylmagnesium chloride (7 mL, 14.0 mmol) in THF is added. Stirring is continued at −75° C. for 1 h, before the mixture is warmed to 0° C. The reaction is quenched by carefully adding water. The mixture is diluted with EA, washed with water followed by brine, dried over $MgSO_4$, filtered and concentrated to give crude 2-isobutyl-6-methoxy-isonicotinic acid methyl ester (1.20 g) as an oil; LC-MS: $t_R$=1.37 min; $[M+1]^+$=224.12.

c) A solution of 2-isobutyl-6-methoxy-isonicotinic acid methyl ester (1.20 g, 5.38 mmol) in 25% aq. HCl (60 mL) is stirred at 65° C. for 16 h. The solvent is removed in vacuo and the residue is dried under HV to give 2-isobutyl-6-methoxy-isonicotinic acid hydrochloride (1.20 g) as a solid; LC-MS*: $t_R$=0.48 min, $[M+1]^+$=210.1.

2-(1-Ethyl-propyl)-6-methoxy-isonicotinic acid

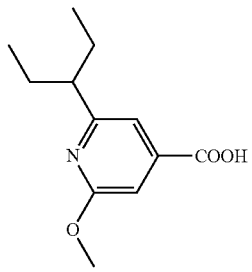 [SMILES: CCC(CC)c1cc(C(=O)O)cc(OC)n1]

a) Under argon, Pd(dppf) (83 mg, 101 μmol) is added to a solution of 2-chloro-6-methoxy-isonicotinic acid methyl ester (2.00 g, 9.92 mmol, see preparation of 2-isobutyl-6-methoxy-isonicotinic acid) in dioxane (30 mL). To this mixture, a solution of 1-ethyl-propyl zinkbromide (1.17 g, 9.92 mmol, 20 mL of a 0.5 M solution in THF) is added. The mixture is stirred at 85° C. for 16 h before the reaction is carefully quenched with water and extracted twice with EA. The combined org. extracts are dried over $MgSO_4$, filtered and concentrated. The crude product is purified by CC on silica gel eluting with heptane:EA 9:1 to give 2-(1-ethyl-propyl)-6-methoxy-isonicotinic acid methyl ester (1.17 g) as a pale yellow oil; LC-MS: $t_R$=1.08 min; $[M+1]^+$=238.03.

b) A solution of 2-(1-ethyl-propyl)-6-methoxy-isonicotinic acid methyl ester (1.17 g, 4.97 mmol) in 25% aq. HCl (25 mL) is stirred at 70° C. for 16 h. The solvent is evaporated and the residue is dried under HV to give the title compound (2.00 g) as a yellow solid; LC-MS: $t_R$=0.94 min; $[M+1]^+$=224.01.

2-Cyclopentyl-6-methoxy-isonicotinic acid

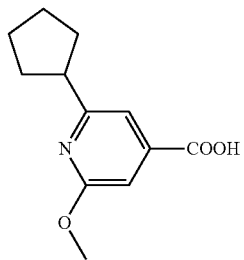 [SMILES: COc1cc(C(=O)O)cc(C2CCCC2)n1]

The title compound is obtained as a white solid in analogy to the procedures given for 2-(1-ethyl-propyl)-6-methoxy-isonicotinic acid above; LC-MS: $t_R$=0.93 min; $[M+1]^+$=221.99.

2-Isopropylamino-6-methyl-isonicotinic acid

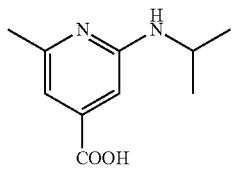

a) A solution of 2-chloro-6-methyl-isonicotinic acid (15.5 g, 90.3 mmol) in ethanol (200 mL) and $H_2SO_4$ (0.5 mL) is stirred at 75° C. for 24 h. The solvent is evaporated and the residue is dissolved in EA (200 mL). The solution is washed with sat. aq. $NaHCO_3$-solution (70 mL) and water (70 mL), dried over $MgSO_4$, filtered, concentrated and dried under HV to give 2-chloro-6-methyl-isonicotinic acid ethyl ester (16.3 g) as a pink powder; LC-MS: $t_R$=0.92 min; $[M+1]^+$=200.17.

b) To a solution of 2-chloro-6-methyl-isonicotinic acid ethyl ester (5.20 g, 26.0 mmol) in dioxane (200 mL), $Cs_2CO_3$ (25.5 g, 78.1 mmol) and isopropylamine (9.24 g, 156.3 mmol) is added. The mixture is degassed and put under $N_2$ before Xantphos (5.43 g, 9.38 mmol) and Pd(II) acetate (1.17 g, 5.26 mmol) are added. The mixture is stirred in a sealed vessel at 85° C. for 18 h. The mixture is cooled to rt, filtered and concentrated. The crude product is purified by CC on silica gel eluting with heptane:EA 7:3 to give 2-isopropylamino-6-methyl-isonicotinic acid ethyl ester (3.91 g) as an orange solid; LC-MS: $t_R$=0.67 min; $[M+1]^+$=223.10.

c) A solution of 2-isopropylamino-6-methyl-isonicotinic acid ethyl ester (3.90 g, 17.5 mmol) in 32% aq. HCl (100 mL) is stirred at 70° C. for 5 h before it is cooled to rt and concentrated. The residue is dried under HV to give 2-isopropylamino-6-methyl-isonicotinic acid hydrochloride (4.20 g) as an orange resin; LC-MS: $t_R$=0.52 min; $[M+1]^+$=195.09.

2-Dimethylamino-6-methyl-isonicotinic acid

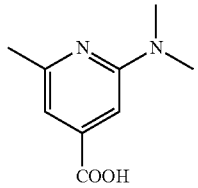

a) 2-Chloro-6-methyl-isonicotinic acid (7.55 g, 44.0 mmol) is suspended in toluene (150 mL) at 80° C. and then treated with N,N-dimethylformamide di-tert.-butyl acetal (50 mL, 209 mmol). The mixture is stirred at 80° C. for 3 h, then at rt for 72 h. The clear solution is diluted with diethyl ether (250 mL), washed with sat. aq. $NaHCO_3$ solution (4×50 mL), dried over $MgSO_4$, filtered and concentrated. The crude product is purified by MPLC on silica gel eluting with heptane: ethyl acetate to give 2-chloro-6-methyl-isonicotinic acid tert.-butyl ester (8.57 g) as a brownish oil which slowly solidifies; LC-MS: $t_R$=0.99 min; $[M+H]^+$=213.24 (−15); $^1H$ NMR ($D_6$-DMSO): δ 1.56 (s, 9H), 2.54 (s, 3H), 7.59 (s, 1H), 7.66 (s, 1H).

b) Under argon, a solution of 2-chloro-6-methyl-isonicotinic acid tert.-butyl ester (625 mg 2.75 mmol), Na tert.-butylate (396 mg, 4.10 mmol), Xantphos (173 mg, 0.30 mmol) and Pd(OAc)$_2$ (83 mg, 0.37 mmol) in 2 M dimethylamine in THF (35 mL) is stirred at 110° C. for 18 h. The dark reaction mixture is cooled to rt, diluted with 6 N aq. HCl and extracted with diethyl ether (4×60 mL). The org. extracts are concentrated, the residue is dissolved in 6 N aq. HCl and heated to 100° C. for 18 h. The orange suspension is concentrated, dissolved in 1 N aq. NaOH (40 mL) and concentrated again. The residue is dissolved in 1 N aq. NaOH (3 mL) and methanol and separated by MPLC on RP-C$_{18}$ silica gel to give 2-dimethylamino-6-methyl-isonicotinic acid (1.1 g) as a beige oil; LC-MS: $t_R$=0.44 min, $[M+H]^+$=181.07.

2-(Ethyl-methyl-amino)-6-methyl-isonicotinic acid

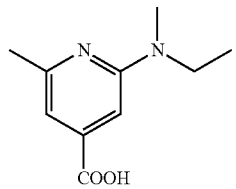

The title compound is obtained as yellow crystals (420 mg) in analogy to 2-dimethylamino-6-methyl-isonicotinic acid starting from 2-chloro-6-methyl-isonicotinic acid tert.-butyl ester (730 mg, 3.21 mmol) and ethyl-methylamine; LC-MS: $t_R$=0.50 min; $[M+H]^+$=195.05; $^1H$ NMR ($D_6$-DMSO): δ 1.08 (t, J=6.8 Hz, 3H), 2.38 (s, 3H), 3.03 (s, 3H), 3.60 (q, J=6.8 Hz, 2H), 6.85 (s, 2H).

2-Diethylamino-6-methyl-isonicotinic acid

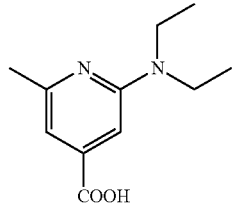

a) A solution of 2,6-dichloroisonicotinic acid (20.0 g, 104 mmol) in ethanol (250 mL) and $H_2SO_4$ (5 mL) is stirred at 80° C. for 28 h. The solvent is removed in vacuo and the residue is dissolved in EA, washed with sat. aq. $NaHCO_3$ solution and water, dried over $MgSO_4$, filtered and evaporated to give 2,6-dichloroisonicotinic acid ethyl ester (17.7 g) as a brownish solid; LC-MS: $t_R$=1.31 min.

b) A solution of 2,6-dichloroisonicotinic acid ethyl ester (14.0 g, 63.6 mmol) in diethylamine (25 mL) is stirred at 100° C. for 7 h. The volatile compounds are evaporated and the residue is purified by CC on silica gel eluting with heptane: EA 9:1 to give 2-chloro-6-diethylamino-isonicotinic acid ethyl ester (10.1 g, contains 2-chloro-6-diethylamino-isonicotinic acid methyl ester which forms during the transfer of the reaction mixture into a round bottom flask using methanol); LC-MS: $t_R$=1.09 min.

c) To a solution of 2-chloro-6-diethylamino-isonicotinic acid ethyl ester (10.1 g, 31.6 mmol) in dioxane (120 mL), Pd(dppf) (262 mg, 0.322 mmol) is added. MeZnCl (8.40 g, 72.4 mmol) is added dropwise to the mixture before it is stirred at 75° C. for 18 h. The mixture is carefully diluted with water, then extracted with EA. The combined org. extracts are dried over $MgSO_4$, filtered and concentrated. The crude product is purified by CC on silica gel eluting with heptane:EA 9:1 to give 2-diethylamino-6-methyl-isonicotinic acid ethyl ester (6.39 g, containing some methyl ester) as a pale yellow oil; LC-MS: $t_R$=0.70 min, $[M+H]^+$=237.11.

d) A solution of 2-diethylamino-6-methyl-isonicotinic acid ethyl ester (6.39 g, 27.0 mmol) in 6 N aq. HCl (100 mL) is stirred at 80° C. for 72 h before the solvent is removed in vacuo. The remaining solid is dried under HV to give 2-diethylamino-6-methyl-isonicotinic acid hydrochloride (6.96 g) as a yellow solid; LC-MS: $t_R$=0.53 min; [M+H]$^+$=209.09; $^1$H NMR (D$_6$-DMSO): δ 1.17 (t, J=6.8 Hz, 6H), 2.51 (s, 3H), 3.68 (q, J=6.3 Hz, 4H), 6.96 (s, 1H), 7.15 (s br, 1H).

2-(Isopropyl-methyl-amino)-6-methyl-isonicotinic acid

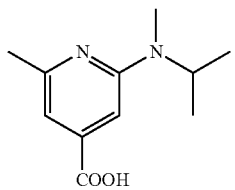

The title compound is prepared in analogy to 2-diethylamino-6-methyl-isonicotinic acid hydrochloride using isopropylmethylamine; LC-MS: $t_R$=0.54 min; [M+H]$^+$=209.09; $^1$H NMR δ 1.37 (d, J=6.3 Hz, 6H), 2.64 (s, 3H), 3.17 (s, 3H), 4.50-4.60 (m, 1H), 7.16 (s, 1H), 7.62 (s, 1H).

2-Methyl-6-pyrrolidin-1-yl-isonicotinic acid

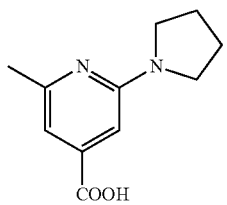

solution of 2-chloro-6-methyl-isonicotinic acid (1.03 g, 5.98 mmol) in pyrrolidine (5 mL) is stirred at 85° C. for 6 days. The mixture is diluted with 1 N aq. NaOH (40 mL) and the solvent is removed in vacuo. The crude product is again dissolved in 1 N aq. NaOH (3 mL) and methanol (1 mL) and purified by MPLC on RP-C$_{18}$-silica gel to give 2-methyl-6-pyrrolidin-1-yl-isonicotinic acid (1.18 g) as a beige solid; LC-MS: $t_R$=0.52 min; [M+H]$^+$=207.06; $^1$H NMR (D$_6$-DMSO): δ 1.89-1.94 (m, 4H), 2.27 (s, 3H), 3.33-3.38 (m, 4H), 6.61 (s, 1H), 6.77 (s, 1H).

2-(Isobutyl-methyl-amino)-6-methyl-isonicotinic acid

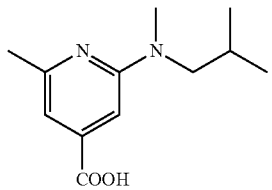 [SMILES: Cc1cc(C(=O)O)cc(N(C)CC(C)C)n1]

The title compound is prepared in analogy to 2-dimethylamino-6-methyl-isonicotinic acid starting from 2-chloro-6-methyl-isonicotinic acid and using isobutyl-methyl-amine; LC-MS: $t_R$=0.61 min, [M+H]$^+$=223.10.

2-Dimethylamino-6-ethyl-isonicotinic acid

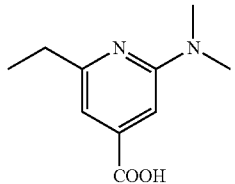

a) 2,6-Dichloro-isonicotinic acid (11.2 g, 57.1 mmol) is suspended in toluene (150 mL) at 80° C. and then treated with N,N-dimethylformamide di-tert.-butyl acetal (50 mL, 209 mmol). The dark mixture is stirred at 80° C. for 12 h, then at rt for 16 h. The dark solution is diluted with diethyl ether (400 mL), washed with sat. aq. NaHCO$_3$ solution (3×100 mL), dried over Na$_2$SO$_4$, filtered and concentrated. The crude product is purified by MPLC on silica gel eluting with a gradient of EA in heptane to give 2,6-dichloro-isonicotinic acid tert.-butyl ester (14.2 g) as a brownish oil which slowly solidifies; LC-MS: $t_R$=1.05 min; $^1$H NMR (D$_6$-DMSO): δ 1.56 (s, 9H), 7.85 (s, 2H).

b) A red to brown solution of 2,6-dichloro-isonicotinic acid tert.-butyl ester (1.49 g, 6.0 mmol) in 2 M dimethylamine in THF (20 mL) is stirred at 65° C. for 2 h, then at 80° C. for 2 h and finally at 110° C. for 12 h in an autoclave. The mixture is concentrated to give crude 2-chloro-6-dimethylamino-isonicotinic acid tert-butyl ester (2.0 g) as a brown residue; LC-MS: $t_R$=1.08 min; [M+H]$^+$=257.32; $^1$H NMR (D$_6$-DMSO): δ 1.54 (s, 9H), 3.06 (s, 6H), 6.85 (s, 1H), 6.92 (s, 1H).

c) To a solution of 2-chloro-6-dimethylamino-isonicotinic acid tert-butyl ester (770 mg, 3.00 mmol) in dioxane (45 mL), Cs$_2$CO$_3$ (1270 mg, 3.90 mmol) followed by P(tert.-Bu)$_3$ (30 mg, 0.15 mmol) and 2,4,6-trivinylcyclotriboroxane pyridine complex (722 mg, 3.00 mmol, prepared according to F. Kerins, D. F. O'Shea J. Org. Chem. 67 (2002) 4968-4971) is added. The mixture is degassed and put under argon before Pd$_2$(dba)$_3$ (82 mg, 0.09 mmol) is added. The mixture is stirred at 100° C. for 15 h before it is cooled to rt and filtered over a short silica gel pad eluting with DCM. The filtrate is concentrated and purified on prep. TLC plates with DCM to give 2-dimethylamino-6-vinyl-isonicotinic acid tert-butyl ester (885 mg) as a red to brownish resin; LC-MS: $t_R$=0.82 min, [M+1]$^+$=249.37.

d) To a solution of 2-dimethylamino-6-vinyl-isonicotinic acid tert-butyl ester (877 mg, 3.53 mmol) in methanol (15 mL), Pd/C (150 mg, 10% Pd) is added and the mixture is stirred under 2 atm of H$_2$ at rt for 3 h. The catalyst is filtered off and the filtrate is evaporated to give crude 2-dimethylamino-6-ethyl-isonicotinic acid tert-butyl ester; LC-MS: $t_R$=0.76 min, [M+1]$^+$=251.10. This material is dissolved in 6 N aq. HCl (60 mL) and the mixture is stirred at 80° C. for 72 h before the solvent is evaporated. The crude product is purified by MPLC on RP-C$_{18}$-silica gel to give 2-dimethylamino-6-ethyl-isonicotinic acid (332 mg) as an orange oil, LC-MS: $t_R$=0.51 min, [M+1]$^+$=195.10.

2-Ethyl-6-(ethyl-methyl-amino)-isonicotinic acid

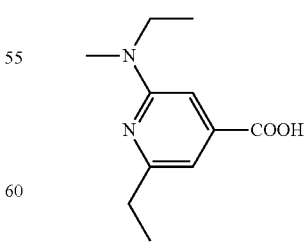

2-Ethyl-6-(ethyl-methyl-amino)-isonicotinic acid is prepared in analogy to 2-dimethylamino-6-ethyl-isonicotinic acid using ethyl-methyl-amine; LC-MS: $t_R$=0.56 min; [M+1]$^+$=209.20; $^1$H NMR (D$_6$-DMSO: δ 1.16 (t, J=7.0 Hz, 3H), 1.24 (t, J=7.3 Hz, 3H), 2.95 (q, J=7.0 Hz, 2H), 3.57 (s, 3H), 3.76 (q, J=6.3 Hz), 6.98 (s, 1H), 7.23 (s, 1H).

2-Diethylamino-6-ethyl-isonicotinic acid

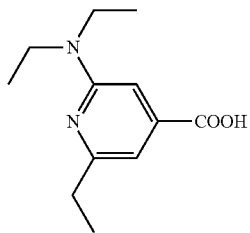 [SMILES: CCc1cc(C(=O)O)cc(N(CC)CC)n1]

The title compound is prepared in analogy to 2-dimethylamino-6-ethyl-isonicotinic acid using diethylamine; LC-MS: $t_R$=0.55 min, $[M+1]^+$=223.37.

2-Ethyl-6-(isopropyl-methyl-amino)-isonicotinic acid

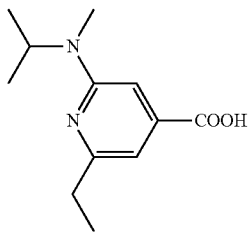 [SMILES: CCc1cc(C(=O)O)cc(N(C)C(C)C)n1]

The title compound is prepared in analogy to 2-dimethylamino-6-ethyl-isonicotinic acid using isopropylmethylamine; LC-MS: $t_R$=0.54 min, $[M+1]^+$=223.37.

2-Dimethylamino-6-isobutyl-isonicotinic acid

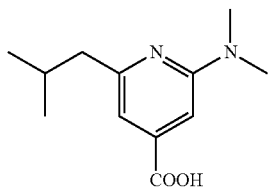 [SMILES: CC(C)Cc1cc(C(=O)O)cc(N(C)C)n1]

The title compound is prepared in analogy to 2-dimethylamino-6-ethyl-isonicotinic acid using 2,4,6-tris-(2-methylpropenyl)-cyclotriboroxane pyridine complex in the Suzuki coupling reaction; LC-MS: $t_R$=0.54 min, $[M+1]^+$=223.37.

6-Isopropoxy-5-methyl-nicotinic acid

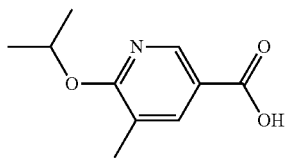

a) A solution of 5,6-dichloronicotinic acid (5.0 g, 26.0 mmol) in dry ethanol (300 mL) and chlorotrimethylsilane (33 mL, 10 eq.) is stirred at rt for 16 h. The solvent is evaporated, the residue dissolved in diethyl ether (200 mL) and washed with a solution of sat. aq. $Na_2CO_3$ (75 mL) and brine (50 mL). The org. phase is dried over $Na_2SO_4$, filtered and evaporated to give 5,6-dichloronicotinic acid ethyl ester (5.8 g) as a solid; LC-MS: $t_R$=0.96 min, $[M+1]^+$=219.93.

b) 5,6-Dichloronicotinic acid ethyl ester (5.33 g, 24.2 mmol) is added to a solution of KOtBu (2.72 g, 24.2 mmol) in isopropanol (50 mL). The mixture is heated at 80° C. for 15 h before another portion of KOtBu (272 mg, 2.42 mmol) is added. Stirring is continued at 80° C. for 24 h. The mixture is diluted with sat. aq. $NaHCO_3$ solution, extracted with diethyl ether, and the combined org. extracts are dried ($Na_2SO_4$), filtered and concentrated. The crude product is purified by CC on silica gel eluting with heptane:EA 9:1 to give 5-chloro-6-isopropoxy-nicotinic acid isopropyl ester; LC-MS: $t_R$=1.10 min, $[M+1]^+$=258.05.

c) To a solution of 5-chloro-6-isopropoxy-nicotinic acid isopropyl ester (235 mg, 0.912 mmol) in dioxane (5 mL), 2,4,6-trimethyl-cyclotriboroxane (114 mg, 0.912 mmol), $Cs_2CO_3$ (386 mg, 1.19 mmol) and tri-tert.-butylphosphine (7.4 mg, 36 µmol) is added. The mixture is degassed and put under argon before $Pd_2(dba)_3$ (17 mg, 18 µmol) is added. The mixture is stirred at 100° C. for 18 h. The mixture is cooled to rt, diluted with water and sat. aq. $NaHCO_3$-solution and extracted with EA. The org. extract is dried over $MgSO_4$, filtered and concentrated. The crude product is purified on prep. TLC plates with heptane:EA 9:1 to give 6-isopropoxy-5-methyl-nicotinic acid isopropyl ester (90 mg) as a colourless oil; LC-MS: $t_R$=1.08 min; $[M+1]^+$=238.08; $^1$H NMR (CDCl$_3$): δ 1.35-1.41 (m, 12H), 2.20 (s, 3H), 5.20-5.30 (m, 1H), 5.37-5.48 (m, 1H), 7.95 (s, 1H), 8.67 (s, 1H). The title compound can be obtained by hydrolising 6-isopropoxy-5-methyl-nicotinic acid isopropyl ester according to the procedure given in step d) of the preparation of 5,6-diisobutyl-nicotinic acid.

alternatively:

a) To a solution of potassium tert. butylate (1.26 g, 11.3 mmol) in isopropanol (30 mL), 2,5-dibromo-3-picoline (2.89 g, 11.3 mmol) is added. The mixture is stirred at 80° C. for 15 h before another portion of potassium tert.-butylate (2.53 g, 27.5 mmol) is added. Stirring is continued at 80° C. for 24 h before the mixture is diluted with sat. aq. $NaHCO_3$-solution. The mixture is extracted with ether, the org. extract is dried over $MgSO_4$, filtered and concentrated. The crude product is purified by CC on silica gel eluting with heptane:EA 9:1 to give 5-bromo-2-isopropoxy-3-methyl-pyridine (1.24 g) as a colourless oil; LC-MS: $t_R$=1.06 min; $[M+1]^+$=230.00; $^1$H NMR (CDCl$_3$): δ 1.35 (d, J=6.3 Hz, 6H), 2.16 (s, 3H), 5.27 (hept, J=6.3 Hz, 1H), 7.48 (d, J=1.5 Hz, 1H), 8.02 (d, J=2.0 Hz, 1H).

b) A solution of 5-bromo-2-isopropoxy-3-methyl-pyridine (1.24 g, 5.39 mmol) and 2,4,6-trivinylcyclotriboroxane pyridine complex (1.27 g, 5.26 mmol) in DME (12 mL) and 2 M aq. $K_2CO_3$ (5 mL) is degassed and put under argon before $Pd(PPh_3)_4$ (112 mg, 0.097 mmol) is added. The mixture is stirred at 80° C. for 15 h before it is cooled to rt, diluted with ether (50 mL), washed with sat. aq. $NaHCO_3$ solution (2×30 mL), dried over $MgSO_4$, filtered and concentrated. The crude product is purified by CC on silica gel eluting with heptane: EA 9:1 to give 2-isopropoxy-3-methyl-5-vinyl-pyridine (703 mg) as pale yellow oil; LC-MS: $t_R$=1.01 min; $[M+1]^+$=178.11.

c) To a solution of 2-isopropoxy-3-methyl-5-vinyl-pyridine (703 mg, 3.97 mmol) in acetone (80 mL), $KMnO_4$ (1.60 g, 10.1 mmol) is added and the mixture is stirred at rt for 18 h. The dark brown suspension is filtered and the clear, colourless filtrate is evaporated to dryness to give 6-isopropoxy-5-methyl-nicotinic acid (1.06 g, as potassium salt) as an off-white solid; LC-MS: $t_R$=0.86 min; $[M+1]^+$=196.09; $^1$H NMR (D$_2$O): δ 1.31 (d, J=6.3 Hz, 6H), 2.14 (s, 3H), 5.15 (hept, J=7.0 Hz, 1H), 7.91 (s, 1H), 8.34 (s, 1H).

6-Isobutyl-nicotinic acid

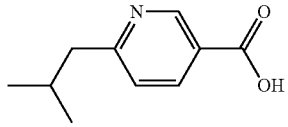

6-Isobutyl-nicotinic acid is prepared in analogy to 5-isobutyl-6-methyl-nicotinic acid from commercially available 6-chloronicotinic acid ethyl ester and isobutylmagnesium chloride; LC-MS: $t_R$=0.52 min, [M+1]$^+$=180.30.

5-Isobutyl-6-methyl-nicotinic acid

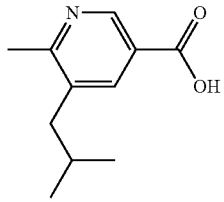

a) A suspension of 5,6-dichloronicotinic acid (5.25 g, 27.3 mmol) in toluene (200 mL) is heated to 80° C. and then slowly treated with N,N-dimethylformamide di-tert. butylacetal (20.0 g, 98.0 mmol). The mixture becomes slightly yellow and clear. Heating and stirring is continued for 3 h before the solution is cooled to rt, diluted with diethyl ether and washed with sat. aq. Na$_2$CO$_3$-solution. The org. phase is dried over MgSO$_4$, filtered and the solvent is evaporated. The residue is purified by MPLC (SiO$_2$) to give 5,6-dichloronicotinic acid tert.-butyl ester (5.13 g). $^1$H NMR (CDCl$_3$): δ 1.62 (s, 9H), 8.30 (d, J=2.0 Hz, 1H), 8.83 (d, J=2.0 Hz, 1H).

b) To a solution of 5,6-dichloronicotinic acid tert.-butyl ester (3.37 g, 13.6 mmol), Fe(acac)$_3$ (719 mg, 2.04 mmol) and NMP (1.95 mL, 20 mmol) in THF (300 mL), a solution of methylmagnesium chloride in THF (3 M, 5.4 mL, 16.3 mmol) is slowly added at −78° C. The brown solution turns turbid and black. Stirring is continued for 1 h at −75° C. before it is warmed to 0° C. The reaction is incomplete and the mixture is cooled again at −70° C. A further batch of methylmagnesium bromide in THF (3 M, 5.4 mL, 16.3 mmol) is slowly added at −70° C. The dark green mixture is slowly warmed to −20° C. and carefully quenched with 0.7 N aq. HCl (150 mL). The mixture is extracted with diethyl ether (5×60 mL). The combined org. extracts are dried over Na$_2$SO$_4$, filtered and evaporated to give crude 5-chloro-6-methyl-nicotinic acid tert.-butyl ester as a yellow oil (4.66 g); LC-MS: $t_R$=1.03 min, [M+1]$^+$=228.22.

c) 5-Chloro-6-methyl-nicotinic acid tert.-butyl ester (3.09 g, 13.5 mmol), Fe(acac)$_3$ (719 mg, 2.04 mmol) and NMP (1.95 mL, 20 mmol) are dissolved in THF (3 M, 500 mL) and cooled at −78° C. A solution of isobutylmagnesium bromide in THF (2 M, 13.6 mmol) is slowly added at −75° C. The brown solution turns turbid and yellow. Stirring is continued for 1 h at −75° C. before it is slowly warmed to rt. The reaction is incomplete, further Fe(acac)$_3$ (719 mg, 2.04 mmol) is added and the mixture is cooled again at −70° C. Further methylmagnesium bromide in THF (2 M, 13.6 mmol) is slowly added at −70° C. The dark green mixture is slowly warmed to rt and stirred for 15 h. The mixture is carefully quenched with 0.7 N aq. HCl (150 mL). The mixture is extracted with EA (6×60 mL). The combined org. extracts are dried over Na$_2$SO$_4$, filtered and evaporated. The residue is purified by reversed phase MPLC to give 6-methyl-5-isobutyl-nicotinic acid tert.-butyl ester as black oil (0.50 g); LC-MS: $t_R$=0.84 min, [M+1]$^+$=250.14.

d) To a solution of 6-methyl-5-isobutyl-nicotinic acid tert.-butyl ester (0.50 g, 2 mmol) in dioxane (20 mL), 4 N HCl in dioxane (30 mL) is added. The mixture is stirred for 3 h. The solvent is evaporated to give 5-isobutyl-6-methyl-nicotinic acid hydrochloride (0.52 g); LC-MS: $t_R$=0.54 min; [M+1]$^+$=194.29; $^1$H NMR (D$_6$-DMSO) δ 0.91 (d, J=6.5 Hz, 6H), 1.91 (hept, J=6.5 Hz), 2.68 (d, J=7.3 Hz, 2H), 2.73 (s, 3H), 8.47 (d, J=1.8 Hz, 1H), 8.90 (d, J=2.0 Hz, 1H).

5,6-Diethyl-nicotinic acid

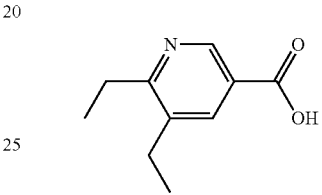

a) To a solution of 5,6-dichloronicotinic acid tert.-butyl ester (5.00 g, 20.0 mmol), and 2,4,6-trivinylcyclotriboroxane pyridine complex (9.700 mg, 40 mmol) in dioxane (30 mL), a solution of 2 M aq. K$_2$CO$_3$ (6 mL) followed by Pd(PPh$_3$)$_4$ (620 mg, 0.38 mmol) and triphenylphosphine (620 mg, 3.8 mmol) is added. The mixture is stirred at 100° C. for 2 h, cooled to rt and diluted with diethyl ether (200 mL). The mixture is extracted with 1M aq. NaOH (2×50 mL) and brine (50 mL). The org. phase is dried (Na$_2$SO$_4$), filtered and evaporated. The residue is purified by FC (SiO$_2$, EA-heptane) to give 5-chloro-6-vinyl-nicotinic acid tert.-butyl ester (4.0 g) as a yellow oil; LC-MS: $t_R$=1.05 min, [M+1+CH$_3$CN]$^+$=281.36.

b) A mixture of 5-chloro-6-vinyl-nicotinic acid tert.-butyl ester (2.0 g), Cs$_2$CO$_3$ (3.4 g), tri(tert.-butyl)phosphine (0.04 eq.), tris(dibenzylidenacetone)dipalladium (0.02 eq.), and 2,4,6-trivinylcyclotriboroxane pyridine complex (2.0 g) in dioxane (30 mL) is degassed and heated at 100° C. for 15 h. The mixture is cooled to rt, and diluted with diethyl ether (200 mL). The mixture is extracted with 1M aq. NaOH (2×50 mL) and brine (50 mL). The org. phase is dried (Na$_2$SO$_4$), filtered and evaporated. The residue is purified by FC (SiO$_2$, EA-heptane) to give 5,6-divinyl-nicotinic acid tert.-butyl ester (0.89 g) as an oil. LC-MS: $t_R$=1.01 min, [M+1]$^+$=232.04.

c) To a solution of 5,6-divinyl-nicotinic acid tert-butyl ester (890 mg, 3.8 mmol) in THF (20 mL) containing some methanol, Pd/C (100 mg, 10% Pd) is added and the mixture is stirred under 1 atm of H$_2$ at rt for 3 h. The catalyst is filtered off and the filtrate is evaporated. The remaining residue is purified by FC (SiO$_2$, EA-heptane) to give 5,6-diethyl-nicotinic acid tert-butyl ester (860 mg) as an oil; LC-MS: $t_R$=0.79 min, [M+1]$^+$=236.14.

d) A solution of 5,6-diethyl-nicotinic acid tert-butyl ester (860 mg, 3.65 mmol) in 6 N aq. HCl (15 mL) is stirred at 65° C. for 3 h before the solvent is evaporated. The residue is dried under HV to give 5,6-diethyl-nicotinic acid hydrochloride (923 mg) as an oil; LC-MS: $t_R$=0.50 min, [M+1]$^+$=180.05.

6-Ethyl-5-isobutyl-nicotinic acid

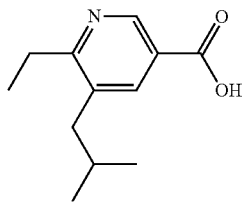

6-Ethyl-5-isobutyl-nicotinic acid is prepared in analogy to 5,6-diethyl-nicotinic acid from 5-chloro-6-vinyl-nicotinic acid tert.-butyl ester and 2,4,6-tri-(2-methyl-propenyl)-cycloboroxane pyridine complex (prepared in analogy to a procedure given by F. Kerins, D. F. O'Shea, *J. Org. Chem.* 67 (2002) 4968-4971); LC-MS: $t_R$=0.64 min, [M+1]$^+$=207.98.

5,6-Diisobutyl-nicotinic acid

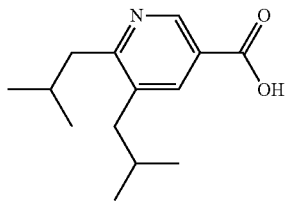 [SMILES: CC(C)Cc1cc(C(=O)O)cnc1CC(C)C]

a) A solution of 5,6-dichloronicotinic acid (5.0 g, 26 mmol) in dry ethanol (300 mL) and chlorotrimethylsilane (33 mL, 10 eq.) is stirred at rt for 16 h. The solvent is evaporated, the residue dissolved in diethyl ether (200 mL) and washed with a solution of sat. aq. Na$_2$CO$_3$ (75 mL) and brine (50 mL). The org. phase is dried over Na$_2$SO$_4$, filtered and evaporated to give 5,6-dichloronicotinic acid ethyl ester (5.8 g) as a solid; LC-MS: $t_R$=0.96 min, [M+1]$^+$=219.93.

b) To a solution of 5,6-dichloronicotinic acid ethyl ester (0.8 g, 3.6 mmol) and 2,4,6-tri-(2-methyl-propenyl)-cycloboroxane pyridine complex (1.78 g, 5.49 mmol) in DME (20 mL), a solution of 2 M aq. K$_2$CO$_3$ (5 mL) followed by Pd(PPh$_3$)$_4$ (50 mg, 0.068 mmol) and triphenylphosphine (110 mg, 0.68 mmol) is added. The mixture is stirred at 100° C. for 2 days before it is cooled to rt and diluted with diethyl ether (100 mL). The phases are separated and the aq. phase re-extracted with diethyl ether (50 mL). The combined org. extracts are washed with 1M aq. NaOH (2×40 mL) and brine (40 mL), dried (Na$_2$SO$_4$), filtered and evaporated. The crude product is purified by FC (SiO$_2$, EA-heptane) to give 5,6-di(2-methyl-propenyl)-nicotinic acid ethyl ester (52 mg) as a colourless oil; LC-MS: $t_R$=1.11 min, [M+1]$^+$=260.24.

c) 5,6-Di(2-methyl-propenyl)-nicotinic acid ethyl ester (52 mg, 0.3 mmol) is dissolved in THF (10 mL), Pd/C (20 mg, 10% Pd) is added and the mixture is stirred under 1 atm H$_2$ at rt for 15 h. The catalyst is filtered off and the filtrate is evaporated to give 5,6-diisobutyl-nicotinic acid ethyl ester (52 mg) as an oil; LC-MS: $t_R$=1.12 min, [M+1]$^+$=264.19.

d) A solution of 5,6-diisobutyl-nicotinic acid ethyl ester (52 mg, 0.2 mmol) in 6 N aq. HCl (2 mL) is stirred at 65° C. for 15 h before it is cooled to rt and extracted with diethyl ether (2×10 mL). The aq. phase is evaporated and the residue is dried under HV to give 5,6-diisobutyl-nicotinic acid hydrochloride (0.12 g) as a colourless solid; LC-MS: $t_R$=0.73 min, [M+1]$^+$=236.40.

6-Chloro-5-methyl-nicotinic acid

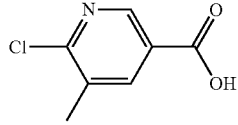

a) Phosphoroxychloride (183 mL, 2 mol) is heated at 90° C. and a mixture of commercially available 2-methyl-2-butenenitrile (73 g, 0.9 mol) and DMF (154 mL, 2 mol) is added slowly while keeping the temperature at 100 to 110° C. The mixture is stirred at 110° C. for 15 h, cooled to rt and diluted with DCM (500 mL). The mixture is cooled at 0° C. and carefully quenched with water (500 mL). The phases are separated and the aq. phase extracted with DCM (total of 800 mL). The combined org. extracts are dried (Na$_2$SO$_4$), filtered and evaporated. The residue is crystallised from cyclohexane to provide 6-chloro-3-formyl-5-methyl-pyridine (28.3 g) as slightly yellow crystals; LC-MS: $t_R$=0.76 min, [M+1]$^+$=156.14.

b) A solution of 6-chloro-3-formyl-5-methyl-pyridine (10 g, 64 mmol) in formic acid (200 mL) is cooled at 0° C. and an aq. 50% weight solution of H$_2$O$_2$ in water (9.6 mL, 360 mmol) is added at this temperature. The mixture is stirred at 0° C. for 15 h, carefully diluted with water (200 mL) and extracted with DCM (8×100 mL). The combined org. extracts are washed with 1M aq. HCl (100 mL) (check for remaining peroxide), dried (MgSO$_4$), filtered and evaporated. The residue is dried to give the title compound (9.56 g); LC-MS: $t_R$=0.72 min, [M+1]$^+$=172.0.

6-Isobutyl-5-methyl-nicotinic acid

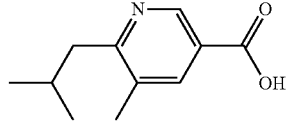

a) A solution of 6-chloro-5-methyl-nicotinic acid (13.85 g, 80.75 mmol) in dry ethanol (200 mL) containing some drops of concentrated H$_2$SO$_4$ is stirred at reflux for 2 days. The solution is cooled to rt, the solvent evaporated, the residue dissolved in EA (200 mL) and washed with a solution of sat. aq. Na$_2$CO$_3$ (2×80 mL), 1M aq. KHSO$_4$ (2×80 mL) and brine (50 mL). The org. phase is dried over MgSO$_4$, filtered and evaporated to give 6-chloro-5-methyl-nicotinic acid ethyl ester (12.65 g) as a solid; LC-MS: $t_R$=0.92 min; [M+1]$^+$=200.10; $^1$H NMR (CDCl$_3$) δ 1.43 (t, J=7.0 Hz, 3H), 2.46 (s, 3H), 4.43 (q, J=7.3 Hz, 2H), 8.16 (m, 1H), 8.84 (d, J=2.0 Hz, 1H).

b) To a solution of 6-chloro-5-methyl-nicotinic acid ethyl ester (4.98 g, 24.9 mmol), 2,4,6-tri-(2-methyl-propenyl)-cycloboroxane pyridine complex (5.74 g, 17.7 mmol, prepared in analogy to a procedure given by F. Kerins, D. F. O'Shea *J. Org. Chem.* 67 (2002) 4968-4971), and triphenylphosphine (1.15 g, 4.4 mmol) in DME (60 mL), a solution of 2 M aq. K$_2$CO$_3$ (20 mL) is added. The mixture is degassed and flushed with N$_2$ before Pd(PPh$_3$)$_4$ (460 mg, 0.4 mmol) is added. The mixture is stirred at 90° C. for 20 h before it is cooled to rt, diluted with EA (150 mL) and washed with sat. aq. NaHCO$_3$ (2×50 mL). The org. extract is dried over MgSO$_4$, filtered and evaporated. The crude product is purified by FC (SiO₂, heptane-EA) to give 5-methyl-6-(2-methyl-propenyl)-nicotinic acid ethyl ester (3.98 g) as an orange oil; LC-MS: $t_R$=0.72 min; [M+1]⁺=220.15.

c) 5-Methyl-6-(2-methyl-propenyl)-nicotinic acid ethyl ester (3.98 g, 18.2 mmol) is dissolved in THF (100 mL) and methanol (100 mL), Pd/C (500 mg, 10% Pd) is added and the mixture is stirred under 1 atm H₂ at rt for 15 h. The catalyst is filtered off and the filtrate is evaporated to give 6-isobutyl-5-methyl-nicotinic acid ethyl ester (3.76 g) as a colourless oil; LC-MS: $t_R$=0.75 min; [M+1]⁺=222.15; ¹H NMR (CDCl₃) δ 0.97 (d, J=6.8 Hz, 6H), 1.42 (t, J=7.3 Hz, 3H), 2.20 (hept, J=6.8 Hz, 1H), 2.38 (s, 3H), 2.75 (d, J=7.0 Hz, 2H), 4.41 (q, J=7.3 Hz, 2H), 8.03 (d, J=1.8 Hz, 1H), 9.00 (d, J=2.0 Hz, 1H).

d) A solution of 6-isobutyl-5-methyl-nicotinic acid ethyl ester (3.75 g, 16.95 mmol) in 12.5% aq. HCl (50 mL) is stirred at 65° C. for 24 h before the solvent is evaporated. The residue is dried under HV to give 6-isobutyl-5-methyl-nicotinic acid hydrochloride (3.55 g) as a white powder; LC-MS: $t_R$=0.57 min; [M+1]⁺=194.25.

5-Methyl-6-propyl-nicotinic acid

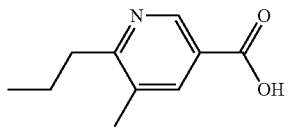

5-Methyl-6-propyl-nicotinic acid (1.85 g as hydrochloride) is prepared in analogy to 6-isobutyl-5-methyl-nicotinic acid from 6-chloro-5-methyl-nicotinic acid ethyl ester (2.0 g) and commercially available trans-1-propen-1-yl boronic acid (1.3 g); ¹H NMR (D₆-DMSO) δ 0.96 (t, J=7.3 Hz, 3H), 1.72 (m, 2H), 3.05 (t, J=7.5 Hz, 2H), 8.66 (m, 1H), 8.86 (d, J=1.5 Hz, 1H).

6-Cyclopentyl-5-methyl-nicotinic acid

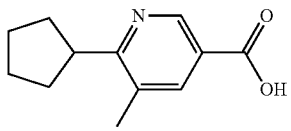

a) 6-Chloro-5-methyl-nicotinic acid isopropyl ester is prepared in analogy to 6-chloro-5-methyl-nicotinic acid ethyl ester; LC-MS: $t_R$=0.97 min; [M+1]⁺=214.03. ¹H NMR (D₆-DMSO): δ 1.34 (d, J=6.3 Hz, 6H), 2.41 (s, 3H), 5.14-5.23 (m, 1H), 8.27 (s, 1H), 8.73 (s, 1H).

b) Under argon, Pd(dppf) (11 mg, 14 μmol) is added to a solution of 6-chloro-5-methyl-nicotinic acid isopropyl ester (300 mg, 1.40 mmol) in dioxane (60 mL). To this mixture, a 0.5 M solution of cyclopentyl zink chloride in THF (452 mg, 2.11 mmol, 4.2 mL) is added dropwise. The mixture is stirred at 75° C. for 18 h before it is cooled to rt and quenched with water. The mixture is further diluted with water and extracted twice with EA (100 mL). The combined org. extracts are dried over MgSO₄, filtered and concentrated. The crude product is purified on prep. TLC plates with heptane:EA 1:1 to give 6-cyclopentyl-5-methyl-nicotinic acid isopropyl ester (138 mg) as a pale yellow oil; LC-MS: $t_R$=0.91 min; [M+1]⁺=248.53.

c) A solution of 6-cyclopentyl-5-methyl-nicotinic acid isopropyl ester (138 mmol, 558 μmol) in 25% aq. HCl (5 mL) is stirred at 65° C. for 24 h. The solvent is evaporated and the residue is dried under HV to give the title compound as a hydrochloride salt (163 mg) in form of a beige solid; LC-MS: $t_R$=0.64 min; [M+1]⁺=206.50.

5-Isobutyl-6-methoxy-nicotinic acid

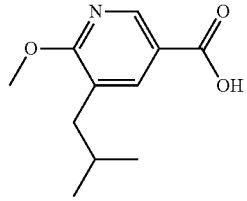

a) 5,6-Dichloro-nicotinic acid (1.00 g, 5.21 mmol) is added to a solution of Na (252 mg, 10.9 mmol) in methanol (50 mL). The mixture is refluxed overnight before another portion of Na (252 mg, 10.9 mmol) is added. Refluxing is continued for 2 h. The mixture is cooled to rt, diluted with water and concentrated. The remaining solid is dissolved in water and the solution is neutralised by adding 2 N aq. HCl. The resulting suspension is extracted twice with EA. The combined org. extracts are dried over MgSO₄, filtered, concentrated and dried to give 5-chloro-6-methoxy-nicotinic acid (976 mg) as a white solid; LC-MS: $t_R$=0.77 min; [M+1]⁺=189.90; ¹H NMR (D₆-DMSO): δ 4.03 (s, 3H), 8.22 (d, J=1.8 Hz, 1H), 8.67 (d, J=2.0 Hz, 1H).

b) A solution of 5-chloro-6-methoxy-nicotinic acid (976 mg, 5.20 mmol) in methynol (50 mL) and H₂SO₄ (0.5 mL) is stirred at 60° C. for 20 h. The mixture is concentrated and the residue is dissolved in EA (150 mL) and washed twice with sat. aq. NaHCO₃ solution. The org. extract is dried over MgSO₄, filtered, concentrated and dried to give 5-chloro-6-methoxy-nicotinic acid methyl ester (880 mg) as a white solid; LC-MS: $t_R$=0.87 min; [M+1]⁺=201.88.

c) To a solution of 5-chloro-6-methoxy-nicotinic acid methyl ester (880 mg, 4.37 mmol) and 2,4,6-tri-(2-methyl-propenyl)-cycloboroxane pyridine complex (1.42 g, 4.37 mmol, prepared in analogy to a procedure given by F. Kerins, D. F. O'Shea *J. Org. Chem.* 67 (2002) 4968-4971) in dioxane (10 mL) and 2 M aq. K₂CO₃ solution (5 mL), Pd(PPh₃)₄ (101 mg, 87 μmol) is added after the mixture has been degassed and put under N₂. The mixture is stirred at 80° C. for 18 h before it is cooled to rt, diluted with EA and washed with water. The org. extract is dried over MgSO₄, filtered and concentrated. The crude product is purified by CC on silica gel eluting with heptane:EA 4:1 to give 6-methoxy-5-(2-methyl-propenyl)-nicotinic acid methyl ester (300 mg) as a colourless oil; LC-MS: $t_R$=1.01 min; [M+1]⁺=222.00; ¹H NMR (CDCl₃): δ 1.85 (d, J=1.3 Hz, 3H), 1.97 (d, J=1.0 Hz, 3H), 3.93 (s, 3H), 4.04 (s, 3H), 6.20 (s, 1H), 8.04 (d, J=2.0 Hz, 1H), 8.71 (d, J=2.3 Hz, 1H).

d) A solution of 6-methoxy-5-(2-methyl-propenyl)-nicotinic acid methyl ester (300 mg, 1.36 mmol) in ethanol (5 mL) is added to a suspension of Pt(IV) oxide (40 mg) in ethanol (5 mL). The mixture is stirred under 1 atm of H₂ at rt for 18 h. The catalyst is filtered off and the filtrate is concentrated. The crude product is purified on prep. TLC plates with heptane: EA 7:3 to give 5-isobutyl-6-methoxy-nicotinic acid methyl ester (260 mg) as a colourless oil; LC-MS: $t_R$=1.08 min; [M+1]⁺=224.49.

e) A solution of 5-isobutyl-6-methoxy-nicotinic acid methyl ester (260 mg, 1.17 mmol) in 25% aq. HCl (10 mL) is stirred at 60° C. for 6 h. The solvent is evaporated and the residue is dried under HV to give the title compound (230 mg) as a white solid; LC-MS: $t_R$=0.95 min; [M+1]⁺=210.51; ¹H NMR (D$_6$-DMSO): δ 0.86 (d, J=6.5 Hz), 1.84-1.95 (m, 1H), 2.46 (d, J=7.0 Hz, 2H), 3.95 (s, 3H), 7.93 (d, J=2.3 Hz, 1H), 8.59 (d, J=2.3 Hz, 1H).

6-Isopropylamino-5-methyl-nicotinic acid

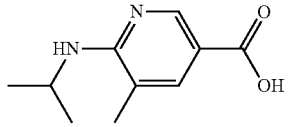

a) To a solution of 6-chloro-5-methyl-nicotinic acid (21.64 g, 126 mmol) in isopropanol (450 mL), trimethylsilyl chloride (160 mL) is added dropwise. Upon completion of the addition, the mixture is heated to 70° C. and stirring is continued for 18 h. The mixture is diluted with diethyl ether (500 mL) and washed with sat. aq. NaHCO$_3$ solution (5×50 mL). The washings are extracted back with diethyl ether (100 mL). The combined org. extracts are dried over MgSO$_4$, filtered and concentrated. The crude product is purified by CC on silica gel eluting with heptane:EA 6:1 to give 6-chloro-5-methyl-nicotinic acid isopropyl ester (6.09 g) as a colourless oil; LC-MS: t$_R$=0.97 min, [M+1]$^+$=214.03. $^1$H NMR (D$_6$-DMSO): δ 1.34 (d, J=6.3 Hz, 6H), 2.41 (s, 3H), 5.11-5.22 (m, 1H), 8.27 (s, 1H), 8.73 (s, 1H).

b) A solution of 6-chloro-5-methyl-nicotinic acid isopropyl ester (200 mg, 0.936 mmol) in dioxane (5 mL) and isopropylamine (3 mL) is stirred in a sealed vial at 100° C. for 1 week. The solvent is evaporated and the residue dissolved in DCM (50 mL) and washed with sat. aq. NaHCO$_3$ solution (20 mL). The org. extract is dried over MgSO$_4$, filtered and concentrated. The crude product is purified on prep. TLC plates with heptane:EA 1:1 to give 6-isopropylamino-5-methyl-nicotinic acid isopropyl ester (137 mg) as a yellow oil; LC-MS: t$_R$=0.68 min, [M+1]$^+$=237.02.

c) A solution of 6-isopropylamino-5-methyl-nicotinic acid isopropyl ester (137 mg, 0.58 mmol) in 25% aq. HCl (5 mL) is stirred at 65° C. for 24 h before it is concentrated and dried to give the title compound (133 mg) as a yellow solid; LC-MS: t$_R$=0.57 min, [M+1]$^+$=195.54.

6-(Ethyl-methyl-amino)-5-methyl-nicotinic acid

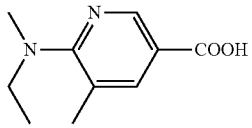

a) To a solution of 5,6-dichloro nicotinic acid (12.2 g, 63.5 mmol) in isopropanol (70 mL), H$_2$SO$_4$ (4 mL) is added dropwise. The mixture is stirred at 80° C. for 16 h before it is cooled to rt and concentrated in vacuo. The residue is dissolved in dioxane (100 mL) and concentrated again. The crude product is purified by CC (heptane:EA 1:3) to give 5,6-dichloro nicotinic acid isopropyl ester (9.29 g) as a pale beige oil; LC-MS: t$_R$=1.33 min, [M+1]$^+$=233.94.

b) A mixture of 5,6-dichloro nicotinic acid isopropyl ester (4.76 g, 22.3 mmol) and ethylmethylamine (6.88 g, 116.4 mmol) is stirred in a sealed vessel at 105° C. for 72 h. The mixture is cooled to rt, diluted with EA (300 mL) and washed with sat. aq. NaHCO$_3$-solution (3×10 mL) followed by brine (10 mL). The org. extract is dried over MgSO$_4$, filtered, concentrated and dried to give 5-chloro-6-(ethyl-methyl-amino)-nicotinic acid isopropyl ester (5.18 g) as a yellow oil; LC-MS: t$_R$=1.38 min, [M+1]$^+$=257.02; $^1$H NMR (D$_6$-DMSO): δ 1.19 (t, J=6.8 Hz, 3H), 1.30 (d, J=6.0 Hz, 6H), 3.08 (s, 3H), 3.55 (q, J=7.0 Hz, 2H), 5.10 (hept, J=6.3 Hz, 1H), 7.98 (s, 1H), 8.58 (s, 1H).

c) A solution of 5-chloro-6-(ethyl-methyl-amino)-nicotinic acid isopropyl ester (5.18 g, 20.1 mmol), NMP (3.0 g, 30.2 mmol) and Fe(acac)$_3$ (498 mg, 1.41 mmol) in THF (150 mL) is put under argon before a methylmagnesium bromide (3.0 g, 25.2 mmol, solution in diethyl ether) is added dropwise. The dark red-brown solution turns yellow, then dark brown again. The mixture is stirred at rt for 2 h before another portion of methylmagnesium bromide (1.44 g, 12.1 mmol) is added. The dark mixture is stirred at rt for 16 h. Another portion of NMP (3.0 g, 30.2 mmol), Fe(acac)$_3$ (498 mg, 1.41 mmol) and methylmagnesium bromide (1.44 g, 12.1 mmol) is added and stirring is continued at rt for one more hour. The reaction mixture is diluted with EA (200 mL) and carefully quenched with ice-water (100 mL). The suspension is basified by adding 1 N aq. NaOH solution (10 mL) and filtered over a small pad of Hyflo and silica gel. The org. phase of the filtrate is separated and collected and the aq. phase is extracted with DCM (3×100 mL). The org. extracts are combined, dried over MgSO$_4$, filtered and concentrated. The crude product is purified by prep. MPLC on silica gel eluting with a gradient of EA in heptane to give 6-(ethyl-methyl-amino)-5-methyl-nicotinic acid isopropyl ester (2.19 g) as a beige oil; LC-MS: t$_R$=0.76 min, [M+1]$^+$=237.20.

d) A solution of 6-(ethyl-methyl-amino)-5-methyl-nicotinic acid isopropyl ester (2.19 g, 9.28 mmol) in THF (40 mL) and 25% aq. HCl (5 mL) is stirred at 65° C. for 3 days before it is cooled to rt and concentrated. The residue is dissolved in dioxane (50 mL) and concentrated again. This procedure is repeated one more time before the residue is dried under HV to give the hydrochloride hydrate of the title compound (2.4 g) as a white powder; LC-MS: t$_R$=0.68 min, [M+1]$^+$=195.07; $^1$H NMR (D$_6$-DMSO): δ 1.13 (t, J=6.8 Hz, 3H), 2.28 (s, 3H), 2.93 (s, 3H), 3.32 (q, J=7.0 Hz, 2H), 7.82 (s, 1H), 8.52 (s, 1H).

6-(Isopropyl-methyl-amino)-5-methyl-nicotinic acid

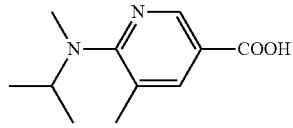

The title compound is prepared in analogy to 6-(ethyl-methyl-amino)-5-methyl-nicotinic acid using N-isopropyl-methyl-amine; LC-MS: t$_R$=0.58 min, [M+1]$^+$=209.10; $^1$H NMR (D$_6$-DMSO): δ 1.23 (d, J=6.5 Hz, 6H), 2.40 (s, 3H), 2.97 (s, 3H), 4.22 (hept, J=6.8 Hz, 1H), 8.07 (s, 1H), 8.43 (d, J=2.0 Hz, 1H).

6-Diethylamino-5-ethyl-nicotinic acid

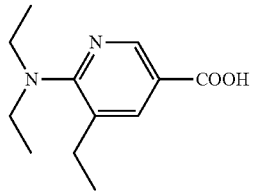 [SMILES: CCc1cc(C(=O)O)cnc1N(CC)CC]

a) To a solution of 5,6-dichloronicotinic acid (10.0 g, 50.0 mmol) in THF (600 mL), triphenylphosphine (19.67 g, 75.0 mmol) and ethanol (5.55 g, 75.0 mmol) is added. The mixture is cooled to 0° C. before DEAD (32.65 g, 75.0 mmol) is added. The mixture is stirred and warmed to rt. Stirring is continued for 16 h before sat. aq. NaHCO$_3$ solution is added. The mixture is repeatedly extracted with EA. The combined org. extracts are dried over MgSO$_4$, filtered and concentrated. The crude product is purified by CC (heptane:EA 7:3) to give 5,6-dichloronicotinic acid ethyl ester (11.4 g) as a white solid; LC-MS: t$_R$=0.96 min, [M+1]$^+$=220.02.

b) A mixture of 5,6-dichloronicotinic acid ethyl ester (2.91 g, 15.2 mmol) and diethyl-amine (11.1 g, 152 mmol) is stirred in a sealed vessel at 80° C. for 72 h. The mixture is cooled to rt and concentrated. The residue is dissolved in DCM (15 mL) and washed with 1 N aq. KHSO$_4$ solution (2×50 mL). The washings are extracted back with DCM (50 mL). The combined org. extracts are dried over Na$_2$SO$_4$, filtered, concentrated and dried to give 5-chloro-6-diethylamino-nicotinic acid ethyl ester (3.36 g) as a yellow oil; LC-MS: t$_R$=1.08 min, [M+1]$^+$=257.12; $^1$H NMR (CDCl$_3$): δ 1.26 (t, J=7.0 Hz, 6H), 1.39 (t, J=7.3 Hz, 3H), 3.62 (q, J=7.0 Hz, 4H), 4.36 (q, J=7.3 Hz, 2H), 8.07 (s, 1H), 8.70 (s, 1H).

c) To a solution of 5-chloro-6-diethylamino-nicotinic acid ethyl ester (2.96 g, 11.5 mmol) in dioxane (50 mL), Pd(dppf) (470 mg, 0.576 mmol) is added under argon. To this mixture, diethyl zinc (8.53 g, 69.1 mmol, as a 1.1 M solution in toluene) is added dropwise. The mixture is stirred at 75° C. for 16 h before another portion of Pd(dppf) 94 mg, 0.115 mmol) and diethyl zinc (1.42 g, 11.5 mmol, as a 1.1 M solution in toluene) is added. Stirring is continued at 75° C. for 24 h. The reaction mixture is cooled to rt and carefully quenched with water. The mixture is filtered over celite and the filtrate is extracted twice with EA. The combined org. extracts are dried over MgSO$_4$, filtered and concentrated. The crude product is purified by CC (heptane:EA 9:1) to give 6-diethylamino-5-ethyl-nicotinic acid ethyl ester (2.40 g) as a colourless oil; LC-MS: t$_R$=0.78 min, [M+1]$^+$=251.19; $^1$H NMR (CDCl$_3$): δ 1.15 (t, J=7.0 Hz, 6H), 1.27 (t, J=7.3 Hz, 3H), 1.40 (t, J=7.3 Hz, 3H), 2.65 (q, J=7.5 Hz, 2H), 3.36 (q, J=7.0 Hz, 4H), 4.37 (q, J=7.0 Hz, 2H), 7.99 (d, J=2.3 Hz, 1H), 8.76 (d, J=2.3 Hz, 1H).

d) A solution of 6-diethylamino-5-ethyl-nicotinic acid ethyl ester (1.78 g, 5.34 mmol) in 25% aq. HCl (50 mL) is stirred at 65° C. for 18 h. The solvent is evaporated and the product is dried under HV to give the hydrochloride hydrate of the title compound (2.30 g) as a white solid; LC-MS: t$_R$=0.62 min, [M+1]$^+$=223.15.

5-Ethyl-6-(isopropyl-methyl-amino)-nicotinic acid

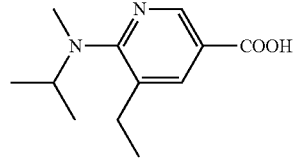 [SMILES: CCc1cc(C(=O)O)cnc1N(C)C(C)C]

The title compound is prepared in analogy to 6-diethylamino-5-ethyl-nicotinic acid using isopropyl-methylamine; LC-MS: t$_R$=0.64 min, [M+1]$^+$=223.14.

4,6-Dimethyl-pyridine-2-carboxylic acid

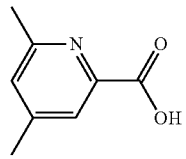

The title compound is commercially available.

5-Isobutyl-4-methyl-pyridine-2-carboxylic acid

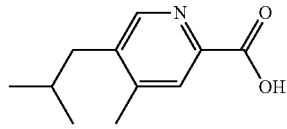

a) To a solution of 2,5-dibromo-4-picoline (9.00 g, 35.9 mmol) in DME (96 mL), 2,4,6-trivinyl-cyclotriboroxane pyridine complex (8.63 g, 35.9 mmol) and 2 N aq. K$_2$CO$_3$-solution (36 mL) is added. The mixture is degassed and put under argon before Pd(PPh$_3$)$_4$ (746 mg, 0.646 mmol) is added. The mixture is stirred at 80° C. for 15 h, before it is cooled to rt, diluted with diethyl ether (50 mL), washed with sat. aq. NaHCO$_3$-solution (2×30 mL), dried over MgSO$_4$, filtered and concentrated. The crude product is purified by CC on silica gel eluting with heptane:EA 9:1 to give 5-bromo-4-methyl-2-vinyl-pyridine (7.04 g) as a yellow oil; LC-MS: t$_R$=0.75 min; [M+1]$^+$=198.22; $^1$H NMR (CDCl$_3$): δ 2.41 (s, 3H), 5.50 (d, J=10.8 Hz, 1H), 6.21 (d, J=17.3 Hz, 1H), 6.74 (dd, J=17.3, 10.8 Hz, 1H), 7.22 (s, 1H), 8.59 (s, 1H).

b) To a solution of 5-bromo-4-methyl-2-vinyl-pyridine (7.04 g, 35.5 mmol) in acetone (280 mL) and water (280 mL), KMnO$_4$ (28.81 g, 71.1 mmol) is added. The dark mixture is stirred at rt for 3 days before it is filtered over a glass-filter pad. The colourless filtrate is evaporated to give crude 5-bromo-4-methyl-pyridine-2-carboxylic acid (10.9 g, as potassium salt) as a white solid; LC-MS: t$_R$=0.64 min, [M+1]$^+$=215.90.

c) To a suspension of crude 5-bromo-4-methyl-pyridine-2-carboxylic acid (10.9 g, as potassium salt, approximately 35.5 mmol) in ethanol (120 mL), H$_2$SO$_4$ (0.5 mL) is added. The mixture is stirred at 70° C. for 18 h. The pH of the clear solution is adjusted to pH 9 by adding sat. aq. NaHCO$_3$-solution and the mixture was extracted with diethyl ether (3×300 mL). The combined org. extracts are dried over MgSO$_4$, filtered and concentrated to give 5-bromo-4-methyl-pyridine-2-carboxylic acid ethyl ester (8.20 g) as a green oil; LC-MS: t$_R$=0.87 min, [M+1]$^+$=243.91.

d) To a solution of 5-bromo-4-methyl-pyridine-2-carboxylic acid ethyl ester (4.03 g, 16.5 mmol) in DME (43 mL), 2,4,6-tri-(2-methyl-propenyl)-cycloboroxane pyridine complex (5.36 g, 16.5 mmol) followed by 2 N aq. K$_2$CO$_3$-solution (16 mL) is added. The mixture is degassed and put under argon before Pd(PPh$_3$)$_4$ (343 mg, 0.297 mmol) is added. The mixture is stirred at 80° C. for 6 h before it is cooled to rt, diluted with diethyl ether (50 mL), washed with sat. aq. NaHCO$_3$-solution (3×30 mL), dried over MgSO$_4$, filtered and concentrated. The crude product is purified by CC on silica gel eluting with heptane:EA 7:3 to give 4-methyl-5-(2-methyl-propenyl)-pyridine-2-carboxylic acid ethyl ester (1.33 g) as a yellow oil; LC-MS: t$_R$=0.87 min, [M+1]$^+$= 220.08.

e) To a solution of 4-methyl-5-(2-methyl-propenyl)-pyridine-2-carboxylic acid ethyl ester (1.33 g, 6.06 mmol) in THF (10 mL) and ethanol (10 mL), Pd/C (300 mg, 10% Pd) is carefully added. The slurry is stirred at rt for 15 h under 2 bar of H$_2$. The catalyst is filtered off and the filtrate is concentrated and dried to give 5-isobutyl-4-methyl-pyridine-2-carboxylic acid ethyl ester (1.27 g) as a colourless oil; LC-MS: t$_R$=0.86 min, [M+1]$^+$=222.10.

f) A solution of 5-isobutyl-4-methyl-pyridine-2-carboxylic acid ethyl ester (1.27 g, 5.76 mmol) in 6 N aq. HCl (110 mL) is stirred at 65° C. for 48 h before the solvent is evaporated in vacuo. The remaining residue is suspended in DCM and filtered. The solid material is washed with additional DCM and dried under HV to give 5-isobutyl-4-methyl-pyridine-2-carboxylic acid hydrochloride (1.05 g) as a white solid; LC-MS: $t_R$=0.59 min; [M+1]$^+$=194.28; $^1$H NMR (D$_6$-DMSO): δ 0.90 (d, J=6.3 Hz, 6H), 1.85-1.96 (m, 1H), 2.69 (d, J=7.0 Hz, 2H), 8.18 (s, 1H), 8.58 (s, 1H), 11.80 (s br, 1H).

6-Isobutyl-4-methyl-pyridine-2-carboxylic acid

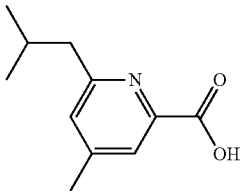

a) A solution of n-BuLi (21.1 mL, 33.8 mmol, 1.6 M) in THF is cooled to −78° C. before a solution of 2,6-dichloro-pyridine (5.0 g, 33.8 mmol) in THF (36 mL) is added dropwise over a period of 20 min. The reaction mixture is stirred at −78° C. for 30 min, and then iodomethane (4.79 g, 33.8 mmol) is added. The mixture is stirred for 30 min before it is quenched with sat. aq. NH$_4$Cl solution at −78° C. The mixture is extracted with diethyl ether, the org. extract is dried over MgSO$_4$, filtered and concentrated. The crude product is purified by CC on silica gel eluting with heptane:EA 19:1 to give 2,6-dichloro-4-methyl-pyridine (2.34 g) as a colourless oil containing the regio isomer 2,6-dichloro-3-methyl-pyridine; LC-MS: $t_R$=0.89 min, [M+1]$^+$=161.97.

b) To a solution of 2,6-dichloro-4-methyl-pyridine (2.34 g, 14.4 mmol) and 2,4,6-trivinyl-cyclotriboroxane pyridine complex (1.75 g, 7.26 mmol) in DME (27 mL), 2 M aq. K$_2$CO$_3$ solution (10 mL) is added. The mixture is degassed and put under argon before Pd(PPh$_3$)$_4$ (300 mg, 0.26 mmol) is added. The mixture is stirred at 80° C. for 3 h before it is cooled to rt, diluted with diethyl ether and washed with sat. aq. NaHCO$_3$ solution. The org. extract is dried over MgSO$_4$, filtered and concentrated. The crude product is purified by CC on silica gel eluting with heptane:EA 9:1. The thus obtained product is dissolved in EA, repeatedly washed with 5% aq. citric acid solution, dried over MgSO$_4$, filtered and evaporated to give 6-chloro-4-methyl-2-vinyl-pyridine (1.24 g) as a colourless oil; LC-MS: $t_R$=0.90 min, [M+1]$^+$=154.03.

c) To a solution of 6-chloro-4-methyl-2-vinyl-pyridine (1.24 g, 8.06 mmol) in water (50 mL) and acetone (50 mL), KMnO$_4$ (6.53 g, 41.3 mmol) is added. The dark mixture becomes warm (40° C.) and is stirred at rt for 3 h before it is filtered over a sintered glass filter. The solvent of the colourless filtrate is evaporated to give crude 6-chloro-4-methyl-pyridine-2-carboxylic acid potassium salt (3.2 g) as a colourless solid; LC-MS: $t_R$=67 min, [M+1]$^+$=171.99. This material is suspended in ethanol (150 mL) and H$_2$SO$_4$ (2 mL) is added until a clear solution forms. The mixture is heated to 70° C. for 18 h. The mixture is carefully diluted with sat. aq. NaHCO$_3$ solution until a pH of 9 is reached. The mixture is extracted three times with EA. The combined org. extracts are dried over MgSO$_4$, filtered and concentrated. The crude product is purified by CC on silica gel eluting with heptane:EA 3:2 to give ethyl 6-chloro-4-methyl-pyridine-2-carboxylate (500 mg) as a pale yellow oil; LC-MS: $t_R$=0.87 min; [M+1]$^+$=200.04; $^1$H NMR (CDCl$_3$): δ 1.45 (t, J=7.3 Hz, 3H), 2.45 (s, 3H), 4.48 (q, J=6.8 Hz, 2H), 7.35 (s, 1H), 7.89 (s, 1H).

d) To a solution of ethyl 6-chloro-4-methyl-pyridine-2-carboxylate (500 mg, 2.51 mmol) and 2,4,6-tris-(2-methyl-propenyl)-cyclotriboroxane pyridine complex (814 mg, 2.51 mmol) in DME (32 mL), 2 M aq. K$_2$CO$_3$ (12 mL) solution is added. The mixture is degassed and put under argon before Pd(PPh$_3$)$_4$ (52 mg, 0.045 mmol) is added. The mixture is stirred at 80° C. for 6 h before it is cooled to rt, diluted with diethyl ether (50 mL) and washed with sat. aq. NaHCO$_3$ (2×30 mL) solution. The org. extract is dried over MgSO$_4$, filtered and concentrated. The crude product is purified by CC on silica gel eluting with heptane:EA 9:1 to give 4-methyl-6-(2-methyl-propenyl)-pyridine-2-carboxylic acid ethyl ester (176 mg) as a yellow oil; $^1$H NMR (CDCl$_3$): δ 1.45 (t, J=7.0 Hz, 3H), 1.97 (s, 3H), 2.12 (s, 3H), 2.42 (s, 3H), 4.46 (q, J=7.0 Hz, 2H), 6.41 (s, 1H), 7.17 (s, 1H), 7.75 (s, 1H).

e) To a solution of 4-methyl-6-(2-methyl-propenyl)-pyridine-2-carboxylic acid ethyl ester (175 mg, 0.80 mmol) in THF (5 mL) and ethanol (5 mL), Pd/C (50 mg, 10% Pd) is added. The mixture is stirred at 50° C. for 15 h under 1 bar of H$_2$. The catalyst is filtered off over celite and the solvent of the filtrate is evaporated to give 6-isobutyl-4-methyl-pyridine-2-carboxylic acid ethyl ester (174 mg) as a colourless oil; LC-MS: $t_R$=0.84 min, [M+1]$^+$=222.48.

f) A solution of 6-isobutyl-4-methyl-pyridine-2-carboxylic acid ethyl ester (174 mg, 0.78 mmol) in 6 N aq. HCl (20 mL) is stirred at 65° C. for 18 h. The solvent is evaporated and the remaining residue is dried under HV to give give 6-isobutyl-4-methyl-pyridine-2-carboxylic acid hydrochloride as green oil; LC-MS: $t_R$=0.58 min, [M+1]$^+$=194.09.

4-Isobutyl-6-methyl-pyridine-2-carboxylic acid

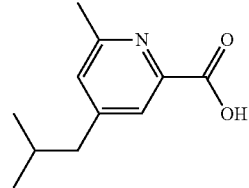

a) To a solution of 4-bromo-2-methyl-pyridine (5.70 g, 32.14 mmol) in methanol (100 mL), H$_2$SO$_4$ (0.3 mL) is added. The mixture is heated to reflux before a solution of ammonium peroxydisulfate (7.33 g, 32.14 mmol) in water (53 mL) is carefully added. The mixture is stirred at reflux für 2 h before two more portions of ammonium peroxydisulfate (2×7.33 g) is added as a sat. aq. solution. Stirring is continued at reflux for 3 h. Methanol is removed under reduced pressure and the remaining solution is diluted with sat. aq. NaHCO$_3$ solution and extracted with EA. The org. extract is dried over MgSO$_4$, filtered and concentrated. The crude product is purified by CC on silica gel eluting with heptane:EA 3:7 to give (4-bromo-6-methyl-pyridin-2-yl)-methanol (1.31 g) as pale yellow solid; LC-MS: $t_R$=0.31 min; [M+1]$^+$=201.96; $^1$H NMR (CDCl$_3$): δ 2.55 (s, 3H), 3.59 (s br, 1H), 4.72 (s br, 2H), 7.28 (s, 2H).

b) To a solution of (4-bromo-6-methyl-pyridin-2-yl)-methanol (1.31 g, 6.48 mmol) in acetone (150 mL), KMnO$_4$ (2.61 g, 16.5 mmol) is added. The mixture is stirred at 40° C. for 2 h before it is filtered over a sintered glass funnel. The filtrate is evaporated to dryness, the remaining solid is washed with water and dried under HV to give 4-bromo-6-methyl-pyridine-2-carboxylic acid potassium salt (1.91 g) as a white solid; LC-MS: $t_R$=0.45 min, [M+1]$^+$=217.89.

c) To a suspension of 4-bromo-6-methyl-pyridine-2-carboxylic acid potassium salt (253 mg, 0.996 mmol) in ethanol (100 mL), H$_2$SO$_4$ (2 mL) is added dropwise. The mixture is heated to 70° C. for 16 h before it is carefully diluted with sat.

aq. NaHCO₃. The mixture is extracted three times with diethyl ether. The combined org. extracts are dried over MgSO₄, filtered and concentrated. The crude product is purified on prep. TLC plates with heptane:EA 3:2 to give 4-bromo-6-methyl-pyridine-2-carboxylic acid ethyl ester (105 mg) as a pale yellow oil; LC-MS: $t_R$=0.85 min, [M+1]⁺=244.22.

d) 4-Isobutyl-6-methyl-pyridine-2-carboxylic acid hydrochloride is prepared starting from 4-bromo-6-methyl-pyridine-2-carboxylic acid ethyl ester following the procedures given in steps d) to f) for the preparation of 6-isobutyl-4-methyl-pyridine-2-carboxylic acid; LC-MS: $t_R$=0.58 min; [M+1]⁺=194.08; ¹H NMR (CDCl₃): δ 1.01 (d, J=6.3 Hz, 6H), 2.04-2.16 (m, 1H), 2.80 (d, J=7.0 Hz, 2H), 3.09 (s, 3H), 7.56 (s, 1H), 8.04 (s, 1H), 9.74 (s br, ~1H).

5-Isobutyl-6-methyl-pyridine-2-carboxylic acid (hydrochloride)

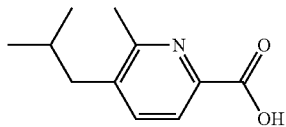

The title compound is prepared starting from 2,5-dibromo-6-picoline following the procedures given in steps b) to f) of the preparation of 6-isobutyl-4-methyl-pyridine-2-carboxylic acid; LC-MS: $t_R$=0.59 min, [M+1]⁺=194.08.

Intermediates: 3-bromo-2-methyl-6-vinyl-pyridine: LC-MS: $t_R$=0.69 min; [M+1]⁺=197.94; ¹H NMR (CDCl₃): δ 2.68 (s, 3H), 5.50 (d, J=10.8 Hz, 1H), 6.20 (d, J=17.6 Hz, 1H), 6.76 (dd, J=17.6, 10.8 Hz, 1H), 7.07 (d, J=8.3 Hz, 1H), 7.75 (d, J=8.0 Hz, 1H); 5-bromo-6-methyl-pyridine-2-carboxylic acid (as potassium salt): LC-MS: $t_R$=0.64 min, [M+1]⁺=217.91; 5-bromo-6-methyl-pyridine-2-carboxylic acid ethyl ester: LC-MS: $t_R$=0.87 min, [M+1]⁺=245.91; 6-methyl-5-(2-methyl-propenyl)-pyridine-2-carboxylic acid ethyl ester: LC-MS: $t_R$=0.88 min, [M+1]⁺=220.11; 5-isobutyl-6-methyl-pyridine-2-carboxylic acid ethyl ester: LC-MS: $t_R$=0.87 min, [M+1]⁺=222.09.

6-Isobutyl-4-methoxy-pyridine-2-carboxylic acid (hydrochloride)

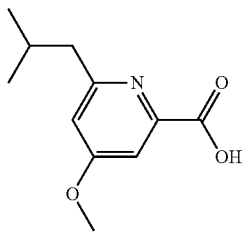

a) To a stirred solution of 6-chloro-4-methoxypyridine-2-carboxylic acid (5.00 g, 26.7 mmol) in ethanol (75 mL), chlorotrimethylsilane (15 mL) is added. The reaction mixture is stirred at rt for 16 h before the solvent is evaporated. The remaining residue is dried under vacuum to give 6-chloro-4-methoxy-2-carboxylic acid ethyl ester (5.95 g) as a pale yellow oil; LC-MS: $t_R$=0.85 min; [M+1]⁺=215.97; ¹H NMR (CDCl₃): δ 1.44 (t, J=7.0 Hz, 3H), 3.94 (s, 3H), 4.48 (q, J=7.0 Hz, 2H), 7.01 (d, J=2.0 Hz, 1H), 7.61 (d, J=2.0 Hz, 1H).

b) The title compound is prepared from 6-chloro-4-methoxy-2-carboxylic acid ethyl ester following the procedures in steps d) to f) of the preparation of 6-isobutyl-4-methyl-pyridine-2-carboxylic acid; LC-MS: $t_R$=0.51 min; [M+1]⁺=210.31; ¹H NMR (CDCl₃): δ 1.04 (d, J=6.5 Hz, 6H), 2.21-2.32 (m, 1H), 3.27 (d, J=7.0 Hz, 2H), 4.20 (s, 3H), 7.12 (s, 1H), 7.83 (s, 1H).

4-Methoxy-5-methyl-pyridine-2-carboxylic acid

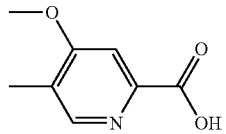

a) 2,4-Dichloro-5-methyl-pyridine is prepared from 2,4-dichloro-5-chloromethyl pyridine as described in WO 2005/068455; LC-MS: $t_R$=0.88 min; [M+1]⁺=161.92; ¹H NMR (CDCl₃): δ 2.36 (s, 3H), 7.37 (s, 1H), 8.24 (s, 1H).

b) To a solution of 2,4-dichloro-5-methyl-pyridine (337 mg, 2.08 mmol) in methanol (10 mL), NaOH (93 mg, 2.33 mmol) is added. The mixture is refluxed for 5 days before it is cooled to rt, diluted with water and extracted with EA. The org. extract is dried over MgSO₄, filtered and concentrated to give 2-chloro-4-methoxy-5-methyl-pyridine (240 mg) as a white solid; ¹H NMR (CDCl₃): δ 2.15 (s, 3H), 3.90 (s, 3H), 6.77 (s, 1H), 8.02 (s, 1H); ¹³C NMR (CDCl): δ 12.67, 55.60, 105.77, 121.77, 149.50, 150.29, 165.41.

c) To a solution of 2-chloro-4-methoxy-5-methyl-pyridine (2.91 g, 18.5 mmol) in DME (75 mL), 2,4,6-trivinylcyclotriboroxane pyridine complex (3.13 g, 13.0 mmol) followed by 2 M aq. K₂CO₃ solution (25 mL) is added. The mixture is degassed and put under argon before Pd(PPh₃)₄ (384 mg, 0.332 mmol) is added. The mixture is stirred at 80° C. for 15 h before it is cooled to rt, diluted with water and extracted with diethyl ether. The org. extract is washed with sat. aq. NaHCO₃ solution, dried over MgSO₄, filtered and concentrated. The crude product is purified by CC on silica gel eluting with heptane:EA 4:1 to give 4-methoxy-5-methyl-2-vinyl-pyridine (1.22 g) as a white solid; LC-MS: $t_R$=0.52 min, [M+1]⁺=150.08.

d) To a solution of 4-methoxy-5-methyl-2-vinyl-pyridine (1.22 g, 8.20 mmol) in acetone:water 1:1 (50 mL), KMnO₄ (6.64 g, 42.0 mmol) is added. The mixture is stirred at rt for 3 h before it is filtered. The filter cake is washed with water and acetone and the filtrate is concentrated and dried under HV to give 4-methoxy-5-methyl-pyridine-2-carboxylic acid potassium salt (2.20 g) as a light brown solid; LC-MS: $t_R$=0.41 min, [M+1]⁺=167.99. To facilitate the purification of the compound, the material is refluxed for 18 h in ethanol containing H₂SO₄. The resulting 4-methoxy-5-methyl-2-vinyl-pyridine ethyl ester is purified by CC on silica gel eluting with heptane:EA 3:7; LC-MS: $t_R$=0.56 min, [M+1]⁺=195.96; ¹H NMR (CDCl₃): δ 1.47 (t, J=7.3 Hz, 3H), 2.25 (s, 3H), 3.97 (s, 3H), 4.50 (q, J=7.0 Hz, 2H), 7.64 (s, 1H), 8.39 (s, 1H). This ester is then saponified to give the title compound by treatment with 6N HCl at 65° C. for 16 h.

6-Isobutyl-5-methoxy-nicotinic acid

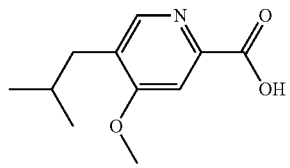

a) To a solution of 2,5-dichloro-4-hydroxypyridine (1.43 g, 8.73 mmol) in DMF (15 mL), K₂CO₃ (2.41 g, 17.5 mmol)

followed by methyl iodide (1.48 g, 8.73 mmol) is added. The mixture is stirred at rt for 24 h before it is diluted with EA (200 mL), washed with water (2×100 mL), dried over MgSO$_4$, filtered and concentrated. The crude product is purified by CC on silica gel eluting with heptane:EA 1:1 to give 2,5-dichloro-4-methoxy-pyridine (0.73 g) as a white solid; LC-MS: $t_R$=0.85 min; [M+1]$^+$=177.90.

b) To a solution of 2,5-dichloro-4-methoxy-pyridine (730 mg, 4.10 mmol) in DME (16 mL), 2,4,6-trivinylcyclotriboroxane pyridine complex (987 mg, 4.10 mmol) followed by 2 M aq. K$_2$CO$_3$ solution (4 mL) is added. The solution is degassed and put under argon before Pd(PPh$_3$)$_4$ (95 mg, 82 µmol) is added. The mixture is stirred for 18 h at 80° C. The mixture is cooled to rt, diluted with EA (200 mL) and washed with water and sat. aq. NaHCO$_3$ solution. The org. extract is dried over MgSO$_4$, filtered and concentrated. The remaining brown residue is purified by CC on silica gel eluting with heptane:EA 9:1 to give 5-chloro-4-methoxy-2-vinyl-pyridine (402 mg) as a pale yellow oil; LC-MS: $t_R$=0.53 min, [M+1]$^+$= 169.98; $^1$H NMR (CDCl$_3$): δ 3.98 (s, 3H), 5.52 (d, J=10.5 Hz, 1H), 6.20 (d, J=17.3 Hz, 1H), 6.76 (dd, J=17.3, 10.8 Hz, 1H), 6.88 (s, 1H), 8.41 (s, 1H).

c) To a solution of 5-chloro-4-methoxy-2-vinyl-pyridine (435 mg, 2.57 mmol) in acetone (20 mL) and water (20 mL), KMnO$_4$ (2.03 g, 12.8 mmol) is added. The mixture is stirred at rt for 15 h before it is filtered through a glass-filter pad. The filtrate is evaporated and dried to give 5-chloro-4-methoxy-pyridine-2-carboxylic acid (987 mg) as potassium salt containing water in the form of a white solid; LC-MS: $t_R$=0.45 min, [M+1]$^+$=187.91. This material is dissolved in ethanol (20 mL) and H$_2$SO$_4$ (4 mL) is added. The mixture is stirred at 80° C. for 18 h. The solvent is evaporated and the residue is dissolved in EA (150 mL) and washed with sat. aq. NaHCO$_3$ solution and water. The org. extract is dried over MgSO$_4$, filtered and concentrated. The crude product is purified on prep. TLC plates using heptane:EA 1:1 to give 5-chloro-4-methoxy-pyridine-2-carboxylic acid ethyl ester (350 mg) as a pale yellow oil; LC-MS: $t_R$=0.81 min, [M+1]$^+$=215.92; $^1$H NMR (D$_6$-DMSO): δ 1.34 (t, J=7.3 Hz, 3H), 4.05 (s, 3H), 4.37 (q, J=7.0 Hz, 2H), 7.75 (s, 1H), 8.61 (m, 1H).

d) To a solution of 5-chloro-4-methoxy-pyridine-2-carboxylic acid ethyl ester (309 mg, 1.43 mmol) in dioxane (10 mL), Pd(dppf) (12 mg, 15 µmol) is added under argon. To this mixture, isobutyl zinkbromide (8.5 mL of a 0.5 M solution in THF) is added dropwise. Upon completion of the addition, the mixture is heated to 75° C. for 18 h. The mixture is cooled to rt, and the reaction is quenched by carefully adding water (50 mL). The mixture is filtered and the filtrate is extracted with EA (2×100 mL). The combined org. extracts are dried over MgSO$_4$, filtered and concentrated. The crude product is purified on prep. TLC plates using heptane:EA 1:1 to give 5-isobutyl-4-methoxy-pyridine-2-carboxylic acid isobutyl ester (134 mg) containing 30% of 5-isobutyl-4-methoxy-pyridine-2-carboxylic acid ethyl ester; LC-MS: $t_R$=0.87 min, [M+1]$^+$=266.04 (isobutyl ester); LC-MS: $t_R$=0.76 min, [M+1]$^+$=238.02 (ethyl ester).

e) A solution of the above 5-isobutyl-4-methoxy-pyridine-2-carboxylic acid isobutyl ester (134 mg, 0.57 mmol) in 5 M aq. HCl (5 mL) is heated to 65° C. for 24 h. The solvent is evaporated and the crude product is purified by prep. HPLC to give the title compound (89 mg) as an off-white solid; LC-MS: $t_R$=0.63 min, [M+1]$^+$=209.98; $^1$H NMR (CD$_3$OD): δ 0.96 (d, J=6.5 Hz, 6H), 1.96-2.08 (m, 1H), 2.67 (d, J=7.0 Hz, 2H), 4.22 (s, 3H), 7.99 (s, 1H), 8.44 (s, 1H).

4-Dimethylamino-6-methyl-pyridine-2-carboxylic acid

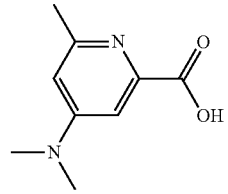

a) A solution of 4-bromo-2-methyl-pyridine (735 mg, 4.14 mmol) in methanol (80 mL) and H$_2$SO$_4$ (20 µL) is heated to reflux. A solution of (NH$_4$)$_2$S$_2$O$_8$ (3.78 g, 16.6 mmol) in water (6.5 mL) is added dropwise to the stirred mixture. Upon completion of the addition, refluxing is continued for 2 h. The mixture is cooled and the reaction is quenched by adding 1 M aq. NaS$_2$O$_3$ solution. The mixture is further diluted with sat. aq. NaHCO$_3$ solution and extracted twice with EA (2×300 mL). The combined org. extracts are dried over MgSO$_4$, filtered and concentrated. The crude product is purified by CC on silica gel eluting with heptane:EA 3:2 to give (4-bromo-6-methyl-pyridin-2-yl)-methanol (156 mg) as a white solid; LC-MS: $t_R$=0.32 min, [M+1]$^+$=201.93.

b) To a solution of (4-bromo-6-methyl-pyridin-2-yl)-methanol (3.13 g, 15.5 mmol) in acetone (400 mL), KMnO$_4$ (6.24 g, 39.5 mmol) is added portionwise. The resulting mixture is stirred at rt for 18 h before it is filtered over a glass-filter. The filter cake is washed with water and acetone and the filtrate is concentrated and dried under HV to give crude 4-bromo-6-methyl-pyridine-2-carboxylic acid potassium salt (5.03 g) as a white solid; $^1$H NMR (D$_2$O): δ 2.47 (s, 3H), 7.58 (s, 1H), 7.85 (s, 1H).

c) Sulfuric acid (5 mL) is added to a suspension of 4-bromo-6-methyl-pyridine-2-carboxylic acid potassium salt (5.03 g, 15.5 mmol) in ethanol (150 mL). The clear solution is heated to 70° C. and stirred for 18 h. The mixture is neutralised with NaHCO$_3$ and sat. aq. NaHCO$_3$ solution and then extracted three times with diethyl ether. The combined org. extracts are dried over MgSO$_4$, filtered and concentrated. The crude product is purified by CC on silica gel eluting with heptane:EA 3:2 to give 4-bromo-6-methyl-pyridine-2-carboxylic acid ethyl ester (2.42 g) as a yellow oil; LC-MS: $t_R$=0.86 min, [M+1]$^+$=243.96.

d) A solution of 4-bromo-6-methyl-pyridine-2-carboxylic acid ethyl ester (2.42 g, 9.91 mmol) in 6 N aq. HCl (100 mL) is stirred at 65° C. for 18 h. The solvent is evaporated and the residue is dried under HV, suspended in DCM, filtered and dried again under HV to give 4-bromo-6-methyl-pyridine-2-carboxylic acid (2.50 g) as a hydrochloride salt in form of a white powder; LC-MS: $t_R$=0.46 min, [M+1]$^+$=215.93.

e) To a solution of 4-bromo-6-methyl-pyridine-2-carboxylic acid hydrochloride (100 mg, 0.396 mmol) in butanol (6 mL), dimethylamine (162 mg, 1.19 mmol) is added and the mixture is refluxed for 2 days. The solvent is removed in vacuo and the residue is dried under HV to give 4-dimethylamino-6-methyl-pyridine-2-carboxylic acid (102 mg) as dimethylammonium salt in form of a yellow oil; LC-MS: $t_R$=0.48 min, [M+1]$^+$=181.07. This material is dissolved in DCM (5 mL), methanol (0.5 mL) and triethylamine (5 mL). The solution is stirred for 5 min at rt before it is concentrated and dried under HV to give the title compound (125 mg) as triethylammonium salt in form of a pale yellow oil. $^1$H NMR (D$_6$-DMSO): δ 1.20 (t, J=7.3 Hz, 18H), 3.08 (q, J=7.0 Hz, 12H), 3.17 (s, 6H), 6.80 (s, 1H), 7.14 (s, 1H), 9.75 (s br, 2H).

4-Diethylamino-6-methyl-pyridine-2-carboxylic acid

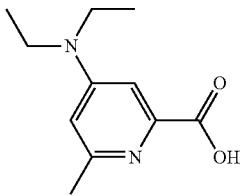

The title compound is prepared in analogy to 4-dimethylamino-6-methyl-pyridine-2-carboxylic acid using diethylamine; LC-MS: $t_R$=0.57 min, [M+1]$^+$=209.08.

4-(Isopropyl-methyl-amino)-6-methyl-pyridine-2-carboxylic acid

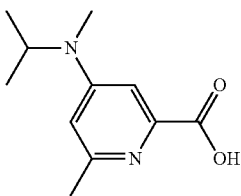

The title compound is obtained as a triethylammonium salt in analogy to 4-dimethylamino-6-methyl-pyridine-2-carboxylic acid using isopropyl-methylamine; LC-MS: $t_R$=0.57 min, [M+1]$^+$=209.08. $^1$H NMR (CDCl$_3$): δ 1.30 (d, J=6.0 Hz, 6H), 1.43 (t, J=7.3 Hz, 9H), 2.74 (s, 3H), 2.99 (s, 3H), 3.15 (q, J=7.3 Hz, 6H), 4.34-4.47 (m, 1H), 6.48 (s, 1H), 7.54 (s, 1H).

6-Methyl-4-methylamino-pyridine-2-carboxylic acid

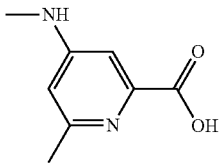

The title compound is obtained in analogy to 4-dimethylamino-6-methyl-pyridine-2-carboxylic acid using methylamine; LC-MS: $t_R$=0.42 min, [M+1]$^+$=167.01. Intermediate: 6-Methyl-4-methylamino-pyridine-2-carboxylic acid ethyl ester; LC-MS: $t_R$=0.56 min, [M+1]$^+$=195.01; $^1$H NMR (CDCl$_3$): δ 1.44 (t, J=7.0 Hz, 3H), 2.53 (s, 3H), 2.92 (d, J=5.0 Hz, 3H), 4.40 (s br, 1H), 4.46 (q, J=7.0 Hz, 2H), 6.46 (d, J=2.3 Hz, 1H), 7.18 (d, J=2.3 Hz, 1H).

4-Isopropylamino-6-methyl-pyridine-2-carboxylic acid

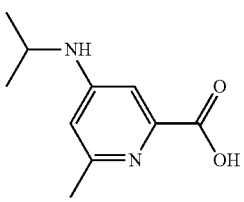

The title compound is obtained in analogy to 4-dimethylamino-6-methyl-pyridine-2-carboxylic acid using isopropylamine; LC-MS: $t_R$=0.60 min, [M+1]$^+$=195.54.

6-Diethylamino-4-methyl-pyridine-2-carboxylic acid

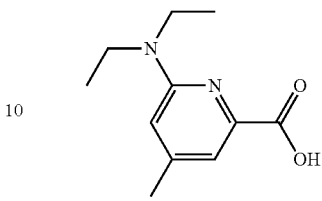

A solution of 6-diethylamino-4-methyl-pyridine-2-carbonitrile (100 mg, 0.528 mmol) in 25% aq. HCl is stirred at 90° C. for 18 h. The mixture is diluted with water and extracted with EA. The pH of the aq. phase is adjusted to pH 11 by adding 1 N aq. NaOH solution and the mixture is extracted with EA. The pH of the aq. phase is adjusted to pH 7 by adding 1 N HCl and the solvent is evaporated. The residue is suspended in DCM/methanol. The suspension is filtered and the filtrate is concentrated and dried to give the title compound (130 mg) as a white solid; LC-MS: $t_R$=0.57 min, [M+1]$^+$=209.01; $^1$H NMR (D$_6$-DMSO): δ 1.12 (t, J=7.0 Hz, 6H), 2.31 (s, 3H), 3.57 (q, J=7.0 Hz, 4H), 6.82 (s, 1H), 7.12 (s, 1H).

6-Bromo-4-methoxy-pyridine-2-carboxylic acid

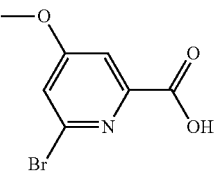

a) Methanol (1.48 g, 46.1 mmol) is slowly added to a cooled suspension (0° C.) of NaH (2.12 g, 53.2 mmol, 60% dispersion in mineral oil, washed with hexane prior to use) in THF (20 mL). Upon completion of the addition the mixture is stirred at 0° C. for 150 min before 2,6-dibromo-4-nitropyridine (10.0 g, 35.4 mmol) is added. The temperature rises to 14° C. The mixture is stirred at rt for 3 h before the reaction is quenched with sat. aq. NH$_4$Cl solution. The mixture is diluted with water and extracted twice with EA (250 mL). The combined org. extracts are dried over MgSO$_4$, filtered and concentrated. The crude product is purified by CC on silica gel eluting with DCM to give 2,6-dibromo-4-methoxy-pyridine (6.43 g) as an off-white solid; LC-MS: $t_R$=0.90 min, [M+1]$^+$=267.75.

b) To a suspension of 2,6-dibromo-4-methoxy-pyridine (5.90 g, 22.1 mmol) in DME (60 mL) and 2 M aq. K$_2$CO$_3$-solution (20 mL), 2,4,6-trivinylcyclotriboroxane pyridine complex (3.19 g, 13.2 mmol) is added and the mixture is degassed and put under N$_2$ before Pd(PPh$_3$)$_4$ (460 mg, 0.398 mmol) is added. The mixture is stirred at 85° C. for 2 h before it is again cooled to rt, diluted with water and extracted with EA. The org. extract is dried over MgSO$_4$, filtered and concentrated. The crude product is purified by CC on silica gel eluting with heptane:EA 4:1 to give 2-bromo-4-methoxy-6-vinyl-pyridine (4.50 g) as a yellow solid; LC-MS: $t_R$=0.90 min, [M+1]$^+$=213.83.

c) To a cooled solution (0° C.) of 2-bromo-4-methoxy-6-vinyl-pyridine (1.56 g, 7.29 mmol) in acetone (30 mL), KMnO$_4$ (2.30 g, 14.6 mmol) is added portionwise. The mixture is stirred at 0° C. for 10 min before it is warmed to rt.

Stirring is continued 2 h. The mixture is filtered, the solid is washed with water and acetone and the filtrate is concentrated. The residue is dissolved in 10% aq. citric acid solution and water and is then extracted twice with EA. The combined org. extracts are dried over MgSO$_4$, filtered, concentrated and dried to give the title compound (1.60 g) as a pale yellow solid. LC-MS*: t$_R$=0.68 min, [M+1]$^+$=231.83.

N-Hydroxy-2-methyl-isonicotinamidine

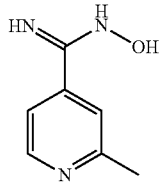

a) A suspension of 2-methyl-pyridine-4-carboxylic acid (1.0 g, 7.29 mmol) in methanol (50 mL) and H$_2$SO$_4$ (0.5 mL) is heated to 70° C. The solid material dissolves and stirring is continued at 70° C. for 18 h. The mixture is cooled to rt, filtered, and the filtrate is evaporated. The remaining solid is washed with diethyl ether and dried to give methyl 2-methyl-pyridine-4-carboxylate; LC-MS: t$_R$=0.39 min, [M+1]$^+$=152.05. This material is dissolved in 7 N NH$_3$ in methanol (25 mL) and the mixture is stirred in a sealed vial for 20 h at 60° C. before it is filtered. The filtrate is evaporated to give crude 2-methyl-isonicotinamide (2.12 g) as a brownish solid. To a solution of this material in DCM (25 mL), pyridine (5.24 g, 54.0 mmol) is added. The mixture is cooled to 0° C. before trifluoroacetic anhydride (8.10 g, 38.6 mmol) is added portionwise. Stirring is continued at 0° C. for 2 h before the reaction is quenched with water. The mixture is diluted with DCM and the org. phase is separated and washed with 5% aq. citric acid solution followed by sat. aq. NaHCO$_3$ solution. The washings are extracted back twice with DCM. The combined org. extracts are dried over MgSO$_4$, filtered and concentrated. The crude product is purified on prep. TLC plates with heptane:EA 4:1 to give 2-methyl-isonicotinonitrile (330 mg); LC-MS: t$_R$=0.55 min, [M+1]$^+$=119.13.

b) To a solution of 2-methyl-isonicotinonitrile (330 mg, 2.79 mmol) in methanol (12 mL), hydroxylamine hydrochloride (388 mg, 5.59 mmol) and NaHCO$_3$ (469 mg, 5.59 mmol) is added. The mixture is stirred in a sealed vial at 60° C. for 16 h before the solvent is evaporated. The residue is dried to give N-hydroxy-2-methyl-isonicotinamidine (550 mg); LC-MS: t$_R$=0.55 min, [M+1]$^+$=152.25.

N-Hydroxy-2,6-dimethyl-isonicotinamidine

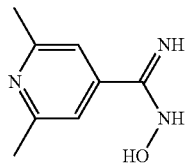

To an ice-cooled solution of potassium tert.-butylate (1.25 g, 11.1 mmol) in methanol (20 mL), hydroxylamine hydrochloride (773 mg, 11.1 mmol) is added. The suspension is stirred for 30 min before 2,6-dimethyl-4-cyano-pyridine (490 mg, 3.71 mmol) is added. The mixture is stirred at 60° C. for 15 h before it is filtered. The filtrate is evaporated to dryness and the resulting solid is washed with water and then dried under HV to give N-hydroxy-2,6-dimethyl-isonicotinamidine (503 mg) as a white powder; LC-MS: t$_R$=0.23 min; [M+1]$^+$=166.01; $^1$H NMR (D$_6$-DMSO): δ 2.43 (s, 6H), 5.88 (s, 2H), 7.30 (s, 2H), 9.90 (s, 1H).

2-Ethyl-N-hydroxy-6-methyl-isonicotinamidine

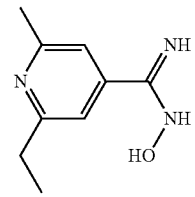

a) A solution of 2-ethyl-6-methyl-isonicotinic acid ethyl ester (3.90 g, 20.2 mmol, prepared in analogy to the corresponding tert.-butyl ester) in 7 N NH$_3$ in methanol (50 mL) is stirred in a sealed vessel at 60° C. for 20 h. The solvent is evaporated and the residue is suspended in diethyl ether. The solid material is collected, washed with additional diethyl ether and dried under HV to give 2-ethyl-6-methyl-isonicotinamide (2.85 g) as a white powder; LC-MS: t$_R$=0.26 min, [M+1]$^+$=165.05; $^1$H NMR (D$_6$-DMSO): δ 1.23 (t, J=7.5 Hz, 3H), 2.49 (s, 3H), 2.75 (q, J=7.8 Hz, 2H), 7.44 (s, 2H), 7.59 (s br, 1H), 8.11 (s br, 1H).

b) To a solution of 2-ethyl-6-methyl-isonicotinamide (2.85 g, 17.4 mmol) and pyridine (6.74 g, 85.2 mmol) in DCM (80 mL), trifluoroacetic anhydride (9.11 g, 43.4 mmol) is added dropwise at 0° C. The mixture is stirred at 0° C. for 1 h before it is carefully diluted with water and DCM. The mixture is washed with 4% aq. citric acid solution followed by sat. aq. NaHCO$_3$-solution. The washings are extracted twice with DCM. The combined org. extracts are dried over MgSO$_4$, filtered and concentrated and briefly dried under HV to give 2-ethyl-4-cyano-6-methyl-pyridine (2.65 g) as a colourless liquid; LC-MS: t$_R$=0.58 min, [M+1]$^+$=147.06; $^1$H NMR (CDCl$_3$): δ 1.33 (t, J=7.5 Hz, 3H), 2.61 (s, 3H), 2.86 (q, J=7.8 Hz, 2H), 7.21 (s, 2H).

c) To an ice-cooled solution of potassium tert.-butylate (7.11 g, 63.4 mmol) in methanol (50 mL), hydroxylamine hydrochloride (3.78 g, 54.4 mmol) is added. The suspension is stirred for 30 min before 2-ethyl-4-cyano-6-methyl-pyridine (2.65 g, 18.1 mmol) is added. The mixture is refluxed for 3 h before it is filtered. The filtrate is evaporated to dryness and the resulting solid is dissolved in water (30 mL) and extracted with EA (3×150 mL). The combined org. extracts are concentrated and dried under HV to give 2-ethyl-N-hydroxy-6-methyl-isonicotinamidine (3.43 g) as a white powder; LC-MS: t$_R$=0.31 min, [M+1]$^+$=180.07; $^1$H NMR (D$_6$-DMSO) δ 1.22 (t, J=7.5 Hz, 3H), 2.44 (s, 3H), 2.71 (q, J=7.5 Hz, 2H), 5.89 (s, 2H), 7.31 (s, 2H), 9.87 (m, 1H).

N-Hydroxy-2-isopropyl-6-methyl-isonicotinamidine

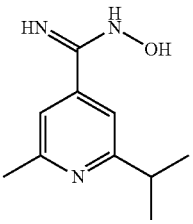

The title compound is prepared in analogy to 2-ethyl-N-hydroxy-6-methyl-isonicotinamidine starting from 2-isopropyl-6-methyl-isonicotinic acid ethyl ester; LC-MS: t$_R$=0.42 min, [M+1]$^+$=194.08; $^1$H NMR (D$_6$-DMSO): δ 1.22 (d, J=7.0

Hz, 6H), 2.44 (s, 3H), 2.91-3.02 (hept, J=7.0 Hz, 1H), 5.91 (s, 2H), 7.32 (s, 2H), 9.88 (s, 1H).

N-Hydroxy-2-isobutyl-6-methyl-isonicotinamidine

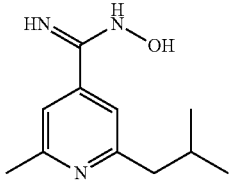

The title compound is prepared in analogy to 2-ethyl-N-hydroxy-6-methyl-isonicotinamidine starting from 2-isobutyl-6-methyl-isonicotinic acid ethyl ester; LC-MS: $t_R$=0.52 min, [M+1]$^+$=208.12; $^1$H NMR (CDCl$_3$): δ 0.94 (d, J=6.5 Hz, 6H), 2.06-2.16 (m, 1H), 2.59 (s, 3H), 2.68 (d, J=7.0 Hz, 2H), 4.91 (s, 2H), 7.17 (s, 1H), 7.22 (s, 1H).

N-Hydroxy-2-methoxy-6-methyl-isonicotinamidine

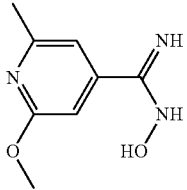

a) Sulfuric acid (1 mL) is added to a suspension of 2-chloro-6-methoxy-isonicotinic acid (4.16 g, 22.2 mmol) in ethanol (20 mL). The clear solution is stirred at 70° C. for 18 h. The mixture is neutralised by adding sat. aq. NaHCO$_3$ solution and then extracted three times with EA (3×250 mL). The combined org. extracts are dried over MgSO$_4$, filtered, concentrated and dried to give 2-chloro-6-methoxy-isonicotinic acid ethyl ester (4.32 g) as a white solid; LC-MS: $t_R$=1.00 min, [M+1]$^+$=215.89.

b) Under argon, dimethyl zink (14.26 g, 149 mmol, 124 mL of a 1.2 M solution in toluene) is added dropwise to a solution of 2-chloro-6-methoxy-isonicotinic acid ethyl ester (5.37 g, 24.9 mmol) and Pd(dppf) (203 mg, 0.249 mmol) in dioxane (120 mL). The mixture is heated to 75° C. and stirred for 18 h before it is cooled again to rt. The reaction is quenched by carefully adding water. The mixture is diluted further with water, filtered over celite and the filtrate is extracted with EA (2×250 mL). The combined org. extracts are dried over MgSO$_4$, filtered and concentrated. The crude product is purified by CC on silica gel eluting with heptane:EA 4:1 to give 2-methoxy-6-methyl-isonicotinic acid ethyl ester (4.10 g) as a colourless oil; LC-MS: $t_R$=0.92 min, [M+1]$^+$=195.93. $^1$H NMR (CDCl$_3$): δ 1.41 (t, J=7.3 Hz, 3H), 2.52 (s, 3H), 3.97 (s, 3H), 4.39 (q, J=7.3 Hz, 2H), 7.12 (s, 1H), 7.28 (s, 1H).

c) The title compound is prepared in analogy to N-hydroxy-6-isobutyl-5-methyl-nicotinamidine from the above 2-methoxy-6-methyl-isonicotinic acid ethyl ester; LC-MS: $t_R$=0.43 min, [M+1]$^+$=181.96. $^1$H NMR (CDCl$_3$): δ 2.49 (s, 3H), 3.95 (s, 3H), 4.89 (s, 2H), 6.75 (s, 1H), 6.98 (s, 1H), 8.03 (s br, 1H).

2-Dimethylamino-N-hydroxy-6-methyl-isonicotinamidine

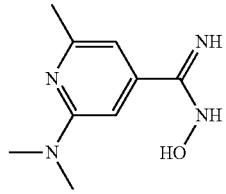

a) A solution of 2,6-dichloroisonicotinonitrile (2.50 g, 14.5 mmol) in 2 N Me$_2$NH in THF (20 mL) is stirred in a sealed vessel at 105° C. for 24 h. The dark suspension is cooled to rt, diluted with EA (200 mL), washed with water (2×50 mL) followed by sat. aq. NaHCO$_3$-solution (50 mL), dried over Na$_2$SO$_4$, filtered and concentrated to give crude 2-chloro-6-dimethylamino-isonicotinonitrile; LC-MS: $t_R$=0.96 min, [M+1]$^+$=182.00. This material is dissolved in dioxane (100 mL) and Pd(dppf) (120 mg, 0.147 mmol) is added. To this solution, MeZnCl (5.02 g, 43.4 mmol, 2 M solution in THF) is slowly added. The mixture is stirred at rt for 30 min, then at 75° C. for 16 h. The orange suspension is cooled to rt, diluted with EA (150 mL) and washed with water (2×50 mL). The aq. washings are basified by adding NaOH and the precipitate that forms is filtered off. The filtrate is extracted with DCM (3×70 mL). The combined org. extracts are dried over Na$_2$SO$_4$, filtered and concentrated. The crude product is purified by MPLC on silica gel eluting with EA containing methanol to give 2-dimethylamino-6-methyl-isonicotinonitrile (699 mg) as a brownish oil which slowly solidifies; LC-MS: $t_R$=0.50 min, [M+1]$^+$=162.05.

b) To an ice-cooled solution of potassium tert.-butylate (1.71 g, 15.2 mmol) in methanol (50 mL), hydroxylamine hydrochloride (905 mg, 13.02 mmol) is added. The suspension is stirred for 30 min before 2-dimethylamino-6-methyl-isonicotinonitrile (699 mg, 4.34 mmol) is added. The mixture is refluxed for 2 h before it is evaporated. The residue is dissolved in a small amount of water and separated by MPLC on RP-C$_{18}$-silica gel to give 2-dimethylamino-N-hydroxy-6-methyl-isonicotinamidine (284 mg) as a brownish resin; LC-MS: $t_R$=0.60 min, [M+1]$^+$=195.42.

N-Hydroxy-2-hydroxymethyl-6-methyl-isonicotinamidine

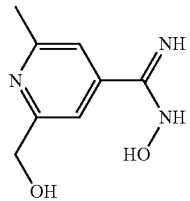

a) A solution of 2-hydroxymethyl-6-methyl-isonicotinic acid methyl ester (400 mg, 2.21 mmol) in 7 N NH$_3$ in methanol (25 mL) is stirred in a sealed vessel at 70° C. for 24 h. The mixture is cooled to rt, the solvent is removed in vacuo and the residue is dried under HV to give crude 2-hydroxymethyl-6-methyl-isonicotinamide (400 mg) as a pale yellow solid; LC-MS: $t_R$=0.21 min, [M+1]$^+$=167.01; $^1$H NMR (D$_6$-DMSO): δ

2.50 (s, 3H), 4.56 (d, J=5.5 Hz, 2H), 5.44 (t, J=5.8 Hz, 1H), 7.49 (s, 1H), 7.58 (s br, 1H), 7.67 (s, 1H), 8.16 (s br, 1H).

b) To a suspension of 2-hydroxymethyl-6-methyl-isonicotinamide (390 mg, 2.38 mmol) and pyridine (922 mg, 9.50 mmol) in DCM (80 mL), trifluoroacetic anhydride (1.25 g, 5.94 mmol) is added dropwise at 0° C. The mixture is stirred at rt for 1 h and becomes clear before it is carefully diluted with water and DCM. The mixture is washed twice with sat. aq. NaHCO$_3$-solution. The washings are extracted twice with DCM. The combined org. extracts are dried over MgSO$_4$, filtered and concentrated and briefly dried under HV to give crude 2-hydroxymethyl-6-methyl-isonicotinonitrile (544 mg, contains pyridine) as a brownish oil; LC-MS: t$_R$=0.54 min, [M+1]$^+$=148.99; $^1$H NMR (CDCl$_3$): δ 2.66 (s, 3H), 3.48 (s br, 1H), 5.48 (s, 2H), 7.41 (s, 2H).

c) To a solution of crude 2-hydroxymethyl-6-methyl-isonicotinonitrile (544 mg, 2.38 mmol) in methanol (50 mL), potassium tert.-butylate (933 mg, 8.31 mmol) and hydroxylamine hydrochloride (495 mg, 7.13 mmol) is added. The solution is refluxed for 2 h. The resulting suspension is cooled to rt and filtered. The solvent filtrate is evaporated and the remaining residue is suspended in water, filtered off, washed with additional water and dried under HV to give N-hydroxy-2-hydroxymethyl-6-methyl-isonicotinamidine (235 mg) as a beige powder; LC-MS: t$_R$=0.17 min, [M+1]$^+$=182.01; $^1$H NMR (D$_6$-DMSO): δ 2.45 (s, 3H), 4.52 (d, J=5.8 Hz, 2H), 5.37 (t, J=5.8 Hz, 1H), 5.90 (s, 2H), 7.36 (s, 1H), 7.56 (s, 1H), 9.92 (s, 1H).

N-Hydroxy-6-isobutyl-5-methyl-nicotinamidine

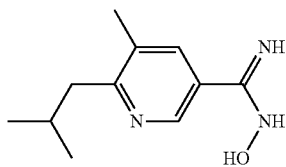

a) To a solution of 6-isobutyl-5-methyl-nicotinic acid (200 mg, 0.871 mmol) and DIPEA (450 mg, 3.48 mmol) in DMF (9 mL), PyBOP (498 mg, 0.958 mmol) is added at 0° C. The mixture is stirred for 15 min before 0.5 M NH$_3$ in dioxane (6.1 mL, 3.05 mmol) is added. Stirring is continued for 2 h at rt. The mixture is concentrated to give crude 6-isobutyl-5-methyl-nicotinamide; LC-MS: t$_R$=0.55 min, [M+1]$^+$=193.10. This material is dissolved in DCM (8 mL), and pyridine (430 mg, 4.43 mmol) followed by trifluoroacetic anhydride (1.25 g, 5.94 mmol) is added dropwise at 0° C. The mixture is stirred at rt for 2 h before it is diluted with DCM. The mixture is washed with a 10% aq. citric acid solution followed by a sat. aq. Na$_2$CO$_3$-solution, dried over MgSO$_4$, filtered and concentrated. The crude product is purified by CC on silica gel eluting with heptane:EA 4:1 to give 6-isobutyl-5-methyl-nicotinonitrile (126 mg) as a colourless oil; LC-MS: t$_R$=0.90 min, [M+1]$^+$=175.17; $^1$H NMR (CDCl$_3$): δ 0.98 (d, J=6.8 Hz, 6H), 2.20 (hept, J=7 Hz, 1H), 2.38 (s, 3H), 2.74 (d, J=7.3 Hz, 2H), 7.69 (s, 1H), 8.67 (s, 1H).

b) To an ice-cooled solution of potassium tert.-butylate (284 g, 2.53 mmol) in methanol (4 mL), hydroxylamine hydrochloride (151 mg, 2.17 mmol) is added. The suspension is stirred for 30 min before 6-isobutyl-5-methyl-nicotinonitrile (126 mg, 0.723 mmol) is added. The mixture is refluxed for 1 h before the solvent is evaporated. The residue is dissolved in sat. aq. NaHCO$_3$-solution (10 mL) and extracted with EA (3×15 mL). The combined org. extracts are dried over MgSO$_4$, filtered, concentrated and dried under HV to give N-hydroxy-6-isobutyl-5-methyl-nicotinamidine (143 mg) as a white solid; LC-MS: t$_R$=0.56 min, [M+1]$^+$=208.13; $^1$H NMR (CDCl$_3$): δ 0.97 (d, J=6.8 Hz, 6H), 2.16 (hept, J=7.0 Hz, 1H), 2.36 (s, 3H), 2.72 (d, J=7.3 Hz, 2H), 4.91 (s, 2H), 7.70 (d, J=1.3 Hz, 1H), 8.66 (d, J=1.8 Hz, 1H).

N-Hydroxy-4,5-dimethyl-pyridine-2-carboxamidine

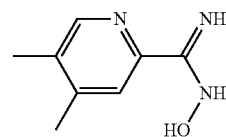

a) Trimethylboroxine (2.84 g, 22.6 mmol), Cs$_2$CO$_3$ (9.58 g, 29.4 mmol) and tri-tert.butyl phosphine (183 mg, 905 μmol) is added to a solution of 5-bromo-4-methyl-pyridine-2-carboxylic acid ethyl ester (5.52 g, 22.6 mmol, see 5-isobutyl-4-methyl-pyridine-2-carboxylic acid) in dioxane (100 mL). The mixture is degassed and put under argon before Pd$_2$(dba)$_3$ (414 mg, 452 μmol) is added. The grey suspension is stirred at 100° C. for 18 h. The mixture is filtered and another portion of trimethylboroxine (2.84 g, 22.6 mmol), Cs$_2$CO$_3$ (9.58 g, 29.4 mmol), Pd$_2$(dba)$_3$ (414 mg, 452 μmol) and tri-tert.butyl phosphine (183 mg, 905 μmol) is added to the filtrate. The mixture is stirred at 100° C. for 72 h before it is again filtered. The filtrate is concentrated, diluted with DCM and washed with sat. Na$_2$CO$_3$ solution (2×25 mL) followed by brine (2×25 mL). The org. extract is dried over MgSO$_4$, filtered and concentrated to give crude 5,6-dimethyl-pyridine-2-carboxilic acid ethyl ester; LC-MS: t$_R$=0.57 min, [M+1]$^+$=166.04.

b) The title compound is prepared from the above 5,6-dimethyl-pyridine-2-carboxilic acid ethyl ester in analogy to N-hydroxy-2-hydroxymethyl-6-methyl-isonicotinamidine; LC-MS: t$_R$=0.48 min, [M+1]$^+$=166.05; $^1$H NMR (CD$_3$OD): δ 2.31 (s, 3H), 2.33 (s, 3H), 7.66 (s, 1H), 8.29 (s, 1H).

5-Ethyl-N-hydroxy-4-methyl-pyridine-2-carboxamidine

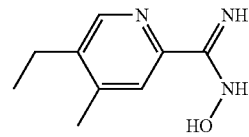

a) 5-Ethyl-4-methyl-pyridine-2-carboxylic acid ethyl ester is prepared in analogy to 5-isobutyl-4-methyl-pyridine-2-carboxylic acid ethyl ester starting from 2,5-dibromo-4-picoline; LC-MS: t$_R$=0.70 min, [M+1]$^+$=193.99; $^1$H NMR (CDCl$_3$): δ 1.25 (t, J=7.8 Hz, 3H), 1.45 (t, J=7.0 Hz, 3H), 2.39 (s, 3H), 2.72 (q, J=7.5 Hz, 2H), 4.48 (q, J=7.0 Hz, 2H), 7.92 (s, 1H), 8.49 (s, 1H).

b) The title compound is prepared from 5-ethyl-4-methyl-pyridine-2-carboxylic acid ethyl ester in analogy to N-hydroxy-2-hydroxymethyl-6-methyl-isonicotinamidine; LC-MS: t$_R$=0.54 min, [M+1]$^+$=180.01; $^1$H NMR (CDCl$_3$): δ

1.25 (t, J=7.5 Hz, 3H), 2.35 (s, 3H), 2.69 (q, J=7.5 Hz, 2H), 5.77 (s br, 2H), 7.75 (s, 1H), 8.32 (s, 1H).

N-Hydroxy-5-isobutyl-4-methyl-pyridine-2-carboxamidine

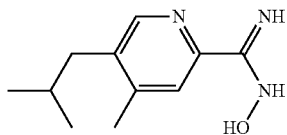

The title compound is prepared in analogy to N-hydroxy-2-hydroxymethyl-6-methyl-isonicotinamidine starting from 5-isobutyl-4-methyl-pyridine-2-carboxylic acid ethyl ester; LC-MS: $t_R$=0.67 min, [M+1]$^+$=208.01; $^1$H NMR (CD$_3$OD): δ 0.97 (d, J=6.8 Hz, 6H), 1.84-1.96 (m, 1H), 2.37 (s, 3H), 2.58 (d, J=7.3 Hz, 2H), 7.67 (s, 1H), 8.26 (s, 1H).

N-Hydroxy-4-methoxy-5-methyl-pyridine-2-carboxamidine

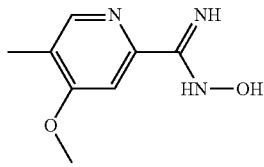

The title compound is prepared from 4-methoxy-5-methyl-pyridine-2-carboxylic acid ethyl ester in analogy to N-hydroxy-2-hydroxymethyl-6-methyl-isonicotinamidine; LC-MS: $t_R$=0.46 min, [M+1]$^+$=181.96.

N-Hydroxy-5,6-dimethyl-pyridine-2-carboxamidine

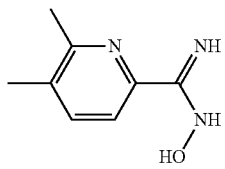

a) Dimethyl zink (4.58 g, 48.0 mmol) is added to a solution of 5-bromo-6-methyl-pyridine-2-carboxylic acid ethyl ester (11.7 g, 48.0 mmol, see preparation of 5-isobutyl-6-methyl-pyridine-2-carboxylic acid) and Pd(dppf) (392 mg, 0.48 mmol) in dioxane (40 mL). The mixture becomes warm and is stirred at rt for 1 h. Another portion of dimethyl zink (4.58 g, 48.0 mmol) is added. The mixture is stirred at 100° C. for 2 h, then at 80° C. for 72 h before it is cooled to rt, and diluted with EA (250 mL) and ice-water (150 mL). The mixture is acidified with 2 N aq. HCl, the org. phase is separated and the aq. phase is extracted with EA (3×100 mL) and DCM (2×75 mL). The combined org. extracts are dried over Na$_2$SO$_4$, filtered and concentrated. The crude product is purified by MPLC on silica gel (heptane:EA gradient) to give 5,6-dimethyl-pyridine-2-carboxylic acid ethyl ester (434 mg) as a brownish oil; LC-MS: $t_R$=0.61 min, [M+1]$^+$=179.98, $^1$H NMR (CDCl$_3$): δ 1.45 (t, J=7.0 Hz, 3H), 2.37 (s, 3H), 2.62 (s, 3H), 4.48 (q, J=7.3 Hz, 2H), 7.55 (d, J=7.8 Hz, 1H), 7.90 (d, J=7.8 Hz, 1H).

b) The title compound is prepared from the above 5,6-dimethyl-pyridine-2-carboxylic acid ethyl ester in analogy to N-hydroxy-2-hydroxymethyl-6-methyl-isonicotinamidine; LC-MS: $t_R$=0.49 min, [M+1]$^+$=166.03.

5-Ethyl-N-hydroxy-6-methyl-pyridine-2-carboxamidine

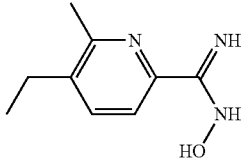

a) Diethyl zink (9.78 g, 79.2 mmol) is added to a solution of 5-bromo-6-methyl-pyridine-2-carboxylic acid isopropyl ester (14.6 g, 56.5 mmol, prepared in analogy to 5-bromo-6-methyl-pyridine-2-carboxylic acid ethyl ester) and Pd(dppf) (461 mg, 0.565 mmol) in dioxane (250 mL). The mixture is stirred at 80° C. for 18 h before it is cooled to rt, diluted with ice-water (150 mL) and EA (250 mL) and acidified with 2 N aq. HCl. The org. layer is separated and the aq. phase is extracted with EA (3×100 mL) and DCM (4×100 mL). The aq. phase is neutralised by adding sat. aq. NaHCO$_3$ solution and is again extracted with DCM (4×75 mL). The combined org. extracts are dried over MgSO$_4$, filtered and concentrated. The crude product is purified by MPLC on silica gel eluting with a gradient of EA in heptane to give 5-ethyl-6-methyl-pyridine-2-carboxylic acid isopropyl ester (7.08 g) as a pale yellow oil; LC-MS: $t_R$=0.77 min, [M+1]$^+$=207.99. $^1$H NMR (CDCl$_3$): δ 1.25 (t, J=7.5 Hz, 3H), 1.41 (d, J=6.3 Hz, 6H), 2.63 (s, 3H), 2.70 (q, J=7.5 Hz, 2H), 5.30 (hept, J=6.3 Hz, 1H), 7.54 (d, J=8.0 Hz, 1H), 7.87 (d, J=8.0 Hz, 1H).

b) The title compound is prepared from the above 5-ethyl-6-methyl-pyridine-2-carboxylic acid isopropyl ester in analogy to N-hydroxy-2-hydroxymethyl-6-methyl-isonicotinamidine; LC-MS: $t_R$=0.49 min, [M+1]$^+$=180.01; $^1$H NMR (CDCl$_3$): δ 1.24 (t, J=7.5 Hz, 3H), 2.56 (s, 3H), 2.67 (q, J=7.5 Hz, 2H), 5.77 (s br, 2H), 7.46 (d, J=8.0 Hz, 1H), 7.72 (d, J=7.8 Hz, 1H), 8.25 (s br, 1H).

N-Hydroxy-5-isobutyl-6-methyl-pyridine-2-carboxamidine

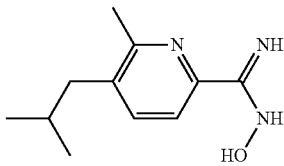

The title compound is prepared from 5-isobutyl-6-methyl-pyridine-2-carboxylic acid ethyl ester in analogy to N-hydroxy-2-hydroxymethyl-6-methyl-isonicotinamidine; LC-MS: $t_R$=0.72 min, [M+1]$^+$=208.52; $^1$H NMR (CD$_3$OD): δ 0.96 (d, J=6.5 Hz, 6H), 1.86-1.97 (m, 1H), 2.54-2.58 (m, 5H), 7.49 (d, J=8.0 Hz, 1H), 7.62 (d, J=8.0 Hz, 1H).

N-Hydroxy-4,6-dimethyl-pyridine-2-carboxamidine

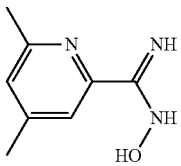

The title compound is prepared in analogy to N-hydroxy-2-methyl-isonicotinamidine starting from 4,6-dimethyl-pyridine-2-carboxylic acid; LC-MS: $t_R$=0.38 min, [M+1]$^+$=166.13.

N-Hydroxy-6-isobutyl-4-methyl-pyridine-2-carboxamidine

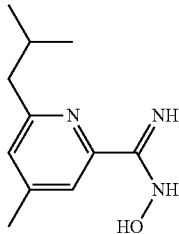

The title compound is prepared from 6-isobutyl-4-methyl-pyridine-2-carboxylic acid in analogy to N-hydroxy-2-methyl-isonicotinamidine; LC-MS: $t_R$=0.63 min, [M+1]$^+$=208.29.

N-Hydroxy-4-isobutyl-6-methyl-pyridine-2-carboxamidine

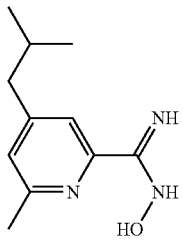

The title compound is prepared starting from 4-isobutyl-6-methyl-pyridine-2-carboxylic acid ethyl ester in analogy to N-hydroxy-2-hydroxymethyl-6-methyl-isonicotinamidine; LC-MS: $t_R$=0.66 min, [M+1]$^+$=208.01.

4-Diethylamino-N-hydroxy-6-methyl-pyridine-2-carboxamidine

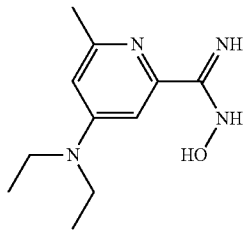 [SMILES: CCN(CC)c1cc(C)nc(C(=N)NO)c1]

The title compound is prepared from 4-diethylamino-6-methyl-pyridine-2-carboxylic acid in analogy to N-hydroxy-2-methyl-isonicotinamidine; LC-MS: $t_R$=0.57 min, [M+1]$^+$=223.02.

N-Hydroxy-6-methyl-4-methylamino-pyridine-2-carboxamidine

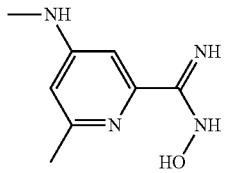

The title compound is prepared from 6-methyl-4-methylamino-pyridine-2-carboxylic acid ethyl ester in analogy to N-hydroxy-2-hydroxymethyl-6-methyl-isonicotinamidine; LC-MS: $t_R$=0.46 min, [M+1]$^+$=181.59; $^1$H NMR (CDCl$_3$): δ 2.44 (s, 3H), 2.88 (d, J=4.8 Hz, 3H), 4.23 (s br, 1H), 5.69 (s br, 2H), 6.34 (d, J=2.0 Hz, 1H), 6.93 (d, J=2.3 Hz, 1H).

The dehydration of 6-methyl-4-methylamino-pyridine-2-carboxylic acid amide (LC-MS: $t_R$=0.42 min, [M+1]$^+$=166.07) with trifluoroacetic anhydride furnishes N-(2-cyano-6-methyl-pyridin-4-yl)-2,2,2-trifluoro-N-methyl-acetamide (LC-MS: $t_R$=0.87 min, [M+1]$^+$=243.96; $^1$H NMR (CDCl$_3$): δ 2.69 (s, 3H), 3.48 (s, 3H), 7.36 (d, J=1.3 Hz, 1H), 7.52 (d, J=1.3 Hz, 1H) which upon treatment with hydroxylamine hydrochloride gives the title compound.

6-Diethylamino-N-hydroxy-4-methyl-pyridine-2-carboxamidine

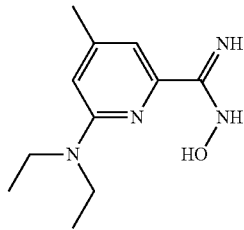 [SMILES: CCN(CC)c1cc(C)cc(C(=N)NO)n1]

a) In a sealed vial, a solution of 2,6-dichloro-4-picoline (1.80 g, 11.1 mmol) in diethylamine (5 mL) is heated to 135° C. for 40 h in a microwave oven. The pressure in the vial reaches 6.5 bar. The mixture is diluted with EA (200 mL) and washed with 1 N KHSO$_4$, solution. The washings are extracted back with EA (100 mL) and the combined org. extracts are dried over MgSO$_4$, filtered and concentrated. The crude product is purified by CC on silica gel eluting with heptane:EA 95:5 to give (6-chloro-4-methyl-pyridin-2-yl)-diethyl-amine (1.15 g) as a colourless solid; LC-MS: $t_R$=1.05 min, [M+1]$^+$=198.97.

b) To a solution of (6-chloro-4-methyl-pyridin-2-yl)-diethyl-amine (5.35 g, 26.9 mmol) in DME (75 mL), 2,4,6-trivinylcyclotriboroxane pyridine complex (6.48 g, 26.9 mmol, prepared according to F. Kerins, D. F. O'Shea J. Org. Chem. 67 (2002) 4968-4971) followed by 2 M aq. K$_2$CO$_3$ solution (25 mL) is added. The solution is degassed and put under argon before Pd(PPh$_3$)$_4$ (560 mg, 0.485 mmol) is added. The mixture is stirred for 15 h at 80° C. Another portion of Pd(PPh$_3$)$_4$ (560 mg, 0.485 mmol) is added, and stirring is continued for 6 h. The mixture is cooled to rt, diluted with diethyl ether and washed with sat. aq. NaHCO$_3$. The org. extract is dried over MgSO$_4$, filtered and concentrated. The remaining yellow oil is purified by prep. HPLC to give diethyl-(4-methyl-6-vinyl-pyridin-2-yl)-amine (1.51 g) as a colourless oil; LC-MS: $t_R$=0.68 min, [M+1]$^+$=191.05. $^1$H NMR (CDCl$_3$): δ 1.20 (t, J=7.0 Hz, 6H), 2.25 (s, 3H), 3.56 (q, J=7.0 Hz, 4H), 5.32 (dd, J=10.5, 2.3 Hz, 1H), 6.23 (dd, J=17.1, 2.0 Hz, 1H), 6.23 (s, 1H), 6.36 (s, 1H), 6.65 (dd, J=17.3, 10.5 Hz, 1H).

c) A solution of diethyl-(4-methyl-6-vinyl-pyridin-2-yl)-amine (457 mg, 2.40 mmol), N-methyl-morpholine-N-oxide (885 mg), and OsO$_4$ (5 mg, 20 μmol, 200 μL of a 2.5% solution in tert.-butanol) in acetone (16 mL) and water (2 mL) is stirred at rt for 18 h. The mixture is diluted with EA (200 mL) and washed with water (50 mL). The org. extract is dried over MgSO$_4$, filtered and concentrated to give crude 1-(6-diethylamino-4-methyl-pyridin-2-yl)ethane-1,2-diol (550 mg) as a brown oil; LC-MS: $t_R$=0.55 min, [M+1]$^+$=225.03. $^1$H NMR (CDCl$_3$): δ 1.20 (t, J=7.0 Hz, 6H), 2.27 (s, 3H), 3.51 (q, J=7.0 Hz, 4H), 3.71 (dd, J=11.3, 5.8 Hz, 1H), 3.75 (s br, 1H), 3.88 (dd, J=11.0, 3.8 Hz, 1H), 4.62 (t, J=4.8 Hz, 1H), 6.22 (s, 1H), 6.33 (s, 1H). A solution of the above crude 1-(6-diethylamino-4-methyl-pyridin-2-yl)-ethane-1,2-diol (550 mg, 2.45 mmol) and NaIO$_4$ (857 mg, 4.01 mmol) in THF (18 mL) and water (3 mL) is stirred at rt for 7 h before another portion of NaIO$_4$ (524 mg, 2.45 mmol) is added. Stirring is continued for 16 h. The mixture is diluted with EA, washed with water, dried over MgSO$_4$, filtered and concentrated to give crude 6-diethylamino-4-methyl-pyridine-2-carbaldehyde (427 mg) as a green oil; LC-MS: $t_R$=0.55 min, [M+1]$^+$= 193.01; $^1$H NMR (CDCl$_3$): δ 1.22 (t, J=7.0 Hz, 6H), 2.34 (s, 3H), 3.60 (q, J=7.0 Hz, 4H), 6.49 (s, 1H), 7.04 (s, 1H), 9.89 (s, 1H).

d) A solution of 6-diethylamino-4-methyl-pyridine-2-carbaldehyde (427 mg, 2.22 mmol) and hydroxylamine hydrochloride (232 mg, 3.33 mmol) in NMP (10 mL) is stirred at 80° C. for 3 h, then at 90° C. for 10 h under microwave irradiation. The solution is cooled to 0° C. before pyridine (1.10 g, 11.3 mmol) and trifluoromethane sulfonic anhydride (3.15 g, 11.2 mmol) is added. The mixture is warmed to rt and stirred for 18 h before it is diluted with DCM (100 mL) and washed with 10% aq. citric acid solution (50 mL) followed by sat. aq. Na$_2$CO$_3$ solution. The org. extract is dried over MgSO$_4$, filtered and concentrated. The crude product is purified by CC on silica gel eluting with heptane:EA 7:3 to give 6-diethylamino-4-methyl-pyridine-2-carbonitrile (329 mg) as a pale yellow solid; LC-MS: $t_R$=1.02 min, [M+1]$^+$=190.02. $^1$H NMR (CDCl$_3$): δ 1.19 (t, J=7.0 Hz, 6H), 2.28 (s, 3H), 3.52 (q, J=7.0 Hz, 4H), 6.44 (s, 1H), 6.74 (s, 1H).

e) To a cold (0° C.) solution of potassium tert.-butylate (494 mg, 4.40 mmol) in methanol (10 mL), hydroxylamine hydrochloride (262 mg, 3.73 mmol) is added. The mixture is stirred for 30 min before 6-diethylamino-4-methyl-pyridine-2-carbonitrile (238 mg, 1.26 mmol) is added. Stirring is continued at rt for 18 h before the solvent is evaporated. The residue is dissolved in 1 N aq. HCl. The solution is extracted with EA. The pH of the aq. phase is adjusted to pH ~9 by adding sat. aq. NaHCO$_3$. The mixture is extracted with EA and the org. extract is dried over MgSO$_4$, filtered, concentrated and dried to give 6-diethylamino-N-hydroxy-4-methyl-pyridine-2-carboxamidine (241 mg) as a yellow oil; LC-MS: $t_R$=0.69 min, [M+1]$^+$=223.05.

2,6-Dimethyl-isonicotinic acid hydrazide

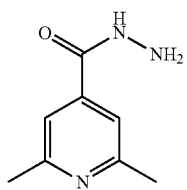

To a solution of 2,6-dimethyl-isonicotinic acid (1.59 g, 10.5 mmol), hydrazinecarboxylic acid tert-butyl ester (1.42 g, 10.7 mmol) and DIPEA (6.06 g, 31.5 mmol) in DMF (33 mL), TBTU (4.05 g, 12.6 mmol) is added. The suspension is stirred at rt for 2 h before it is diluted with EA:diethyl ether 1:1 and washed with 1 N aq. NaOH solution. The washing is extracted three times with DCM, acidified and extracted again with DCM. The combined org. extracts are dried over MgSO$_4$, filtered and concentrated to give crude N'-(2,6-dimethyl-pyridine-4-carbonyl)-hydrazinecarboxylic acid tert-butyl ester (2.79 g) as a brown oil. This material is dissolved 5 M HCl in dioxane (14 mL) and the resulting solution is stirred at rt for 3 h. The solvent is removed in vacuo and the residue is purified by MPLC on RP-C$_{18}$ silica gel to give 2,6-dimethyl-isonicotinic acid hydrazide hydrochloride (1.71 g) as a beige solid; LC-MS: $t_R$=0.15 min, [M+1]$^+$=166.10.

2-Ethyl-6-methyl-isonicotinic acid hydrazide

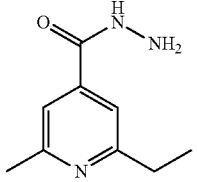

The title compound is prepared in analogy to 2,6-dimethyl-isonicotinic acid hydrazide hydrochloride starting from 2-ethyl-6-methyl-isonicotinic acid; $^1$H NMR S 1.46 (t, J=7.6 Hz, 3H), 2.87 (s, 3H), 3.15 (q, J=7.6 Hz, 3H), 8.14 (s, 1H), 8.16 (s, 1H).

2-Isobutyl-6-methyl-isonicotinic acid hydrazide

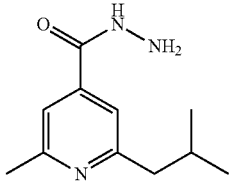

To a solution of 2-isobutyl-6-methyl-isonicotinic acid (83 mg, 0.359 mmol) and DIPEA (186 mg, 1.44 mmol) in DMF (6 mL) is added TBTU (127 mg, 0.395 mmol) at rt. The mixture is stirred for 45 min before 1 M hydrazine in THF (1.44 mL, 1.44 mmol) is added and stirring is continued for 2 h. The mixture is diluted with ether (200 mL) and washed with 1M aq. HCl (3×5 mL), 1M aq. NaOH (3×5 mL) and brine (5 mL). The org. phase is separated, dried over MgSO$_4$, filtered and evaporated. The crude product is purified on prep. TLC plates with DCM containing 4% of methanol to give 2-isobutyl-6-methyl-isonicotinic acid hydrazide (37 mg) as a yellow oil; LC-MS: $t_R$=0.44 min, [M+1]$^+$=208.10.

2-(1-Ethyl-propyl)-6-methyl-isonicotinic acid hydrazide

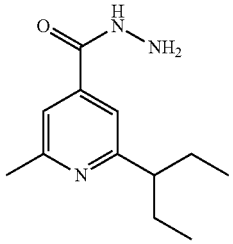 [SMILES: CCC(CC)c1cc(C(=O)NN)cc(C)n1]

The title compound is prepared in analogy to 2-isobutyl-6-methyl-isonicotinic acid hydrazide starting from 2-(1-ethyl-propyl)-6-methyl-isonicotinic acid; LC-MS: $t_R$=0.49 min, [M+1]$^+$=222.02.

The title compound is prepared in analogy to 2-isobutyl-6-methyl-isonicotinic acid hydrazide starting from 2-(1-ethyl-propyl)-6-methyl-isonicotinic acid; LC-MS: $t_R$=0.49 min, $[M+1]^+$=222.02.

2-Diethylamino-6-methyl-isonicotinic acid hydrazide

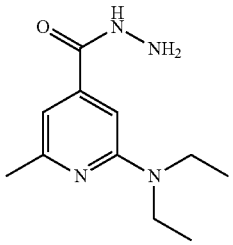 [SMILES: CCN(CC)c1cc(C(=O)NN)cc(C)n1]

The title compound is prepared in analogy to 2-isobutyl-6-methyl-isonicotinic acid hydrazide from 2-diethylamino-6-methyl-isonicotinic acid; LC-MS: $t_R$=0.47 min, $[M+1]^+$=223.14.

General Method for the Preparation of 3,5-Dipyridyl-[1,2,4]oxadiazoles

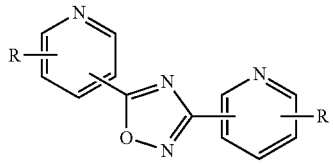

To a solution of the appropriate pyridine carboxylic acid (1 eq.) and DIPEA (3 eq.) in DMF is added PyBOP (1.05 eq.) at 0° C. The mixture is stirred for 15 min at 0° C. The appropriate N-hydroxy pyridine-carboxamidine (1.05 eq.) is added and stirring is continued for 1 to 8 h at 0° C. to rt. The reaction is monitored by LC-MS. Upon complete conversion, the reaction is quenched with water and sat. aq. NaHCO$_3$-solution. The mixture is extracted with diethyl ether, EA or DCM. The org. extracts are dried over MgSO$_4$, filtered and evaporated to give the crude hydroxyamidine ester. This material is dissolved in dioxane and the resulting solution is stirred at 70-90° C. for 4 to 24 h. The solvent is removed in vacuo and the crude product is purified by either CC on silica gel, chromatography on prep. TLC plates or by HPLC to give the desired 3,5-dipyridyl-[1,2,4]oxadiazol in 30-80% yield.

General Method for the Preparation of 2,5-dipyridyl-[1,3,4]thiadiazoles

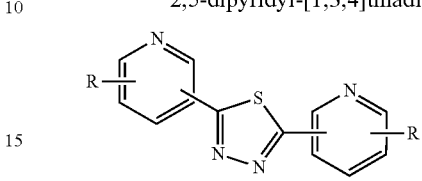

To a solution of the appropriate pyridine-carboxylic acid (1 eq.) and DIPEA (3 eq.) in DCM (20 mL/mmol), TBTU (1 eq.) is added. The mixture is stirred for 5 min before the appropriate pyridine-carboxylic acid hydrazide (1 eq.) is added. The mixture is stirred at rt for 1 h before it is diluted with DCM, washed with water, dried over MgSO$_4$, filtered and concentrated. The remaining residue is dissolved in THF, Lawesson's reagent (2 eq.) is added and the mixture is stirred at 110° C. for 6 min under microwave irradiation. The mixture is diluted with EA, washed with sat. aq. NaHCO$_3$, and concentrated. The crude product is purified by chromatography on prep. TLC plates or by prep. HPLC to give the desired 2,5-dipyridyl-[1,3,4]thiadiazole in 3-44% yield.

Examples 1 to 27

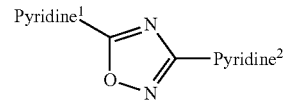

Following the general method for the preparation of 3,5-dipyridyl-[1,2,4]oxadiazoles, the following examples are prepared:

| Ex. No. | Pyridine[1] (as acid) | Pyridine[2] (as hydroxyamidine) | LC-MS $t_R$ [min] | $[M + H]^+$ | Amount Form |
|---|---|---|---|---|---|
| 1 | ![structure] | ![structure] | 0.59 | 295.06 | 32 mg white solid |
| 2 | ![structure] | ![structure] | 0.62 | 309.11 | 22 mg white solid |

-continued

| Ex. No. | Pyridine[1] (as acid) | Pyridine[2] (as hydroxyamidine) | LC-MS $t_R$ [min] $[M+H]^+$ | | Amount Form |
|---|---|---|---|---|---|
| 3 | | | 0.72 | 337.16 | 44 mg pale yellow resin |
| 4 | | | 0.60 | 311.11 | 89 mg off-white solid |
| 5 | | | 0.77 | 337.13 | 68 mg pale yellow resin |
| 6 | | | 0.63 | 309.03 | 42 mg colourless oil |
| 7 | | | 0.67 | 323.12 | 4 mg colourless oil |
| 8 | | | 0.68 | 323.16 | 37 mg white solid |

-continued

| Ex. No. | Pyridine[1] (as acid) | Pyridine[2] (as hydroxyamidine) | LC-MS $t_R$ [min] [M + H]$^+$ | | Amount Form |
|---|---|---|---|---|---|
| 9 | | | 0.70 | 337.13 | 575 mg colourless resin |
| 10 | | | 0.79 | 365.17 | 70 mg white solid |
| 11 | | | 0.69 | 339.15 | 96 mg beige resin |
| 12 | | | 0.70 | 352.18 | 86 mg brownish oil |
| 13 | | | 0.72 | 366.19 | 87 mg brownish oil |
| 14 | | | 0.84 | 365.52 | 75 mg colourless oil |

-continued

| Ex. No. | Pyridine[1] (as acid) | Pyridine[2] (as hydroxyamidine) | LC-MS $t_R$ [min] | $[M + H]^+$ | Amount Form |
|---|---|---|---|---|---|
| 15 | | | 0.61 | 339.15 | 56 mg beige powder |
| 16 | | | 0.63 | 353.18 | 72 mg beige powder |
| 17 | | | 0.70 | 366.18 | 89 mg beige solid |
| 18 | | | 0.62 | 340.13 | 70 mg yellow foam |
| 19 | | | 0.61 | 353.42 | 29 mg beige crystalline solid |
| 20 | | | 0.66 | 367.17 | 25 mg yellow resin |
| 21 | | | 0.67 | 352.17 | 30 mg brownish crystalline solid |

-continued
| Ex. No. | Pyridine[1] (as acid) | Pyridine[2] (as hydroxyamidine) | LC-MS $t_R$ [min] [M + H]$^+$ | | Amount Form |
|---|---|---|---|---|---|
| 22 | 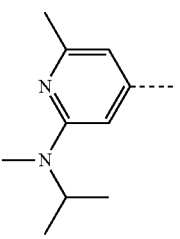 | 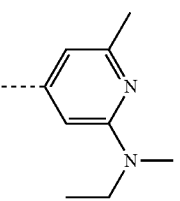 | 0.69 | 381.18 | 20 mg yellow resin |
| 23 | 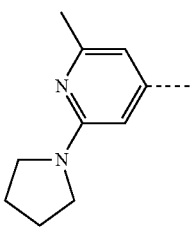 | 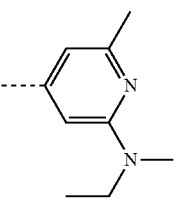 | 0.65 | 379.17 | 8 mg beige solid |
| 24 | 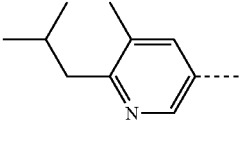 | 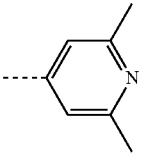 | 0.77 | 323.12 | 93 mg pale yellow oil |
| 25 | 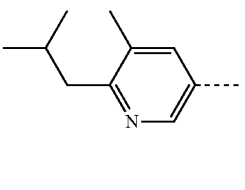 | 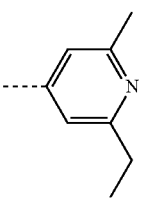 | 0.81 | 337.15 | 34 mg colourless oil |
| 26 | 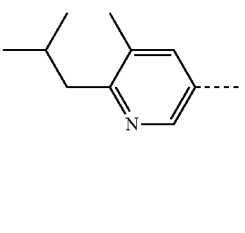 | 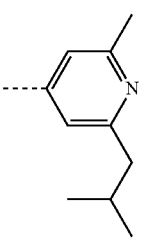 | 0.87 | 365.18 | 62 mg pale yellow oil |
| 27 | 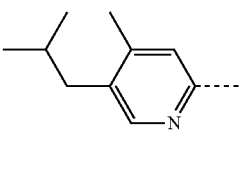 | 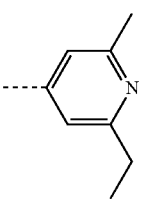 | 0.85 | 337.40 | 34 mg white crystalline solid |

Example 1

$^1$H NMR (CDCl$_3$): δ 1.40 (t, J=7.5 Hz, 3H), 2.66 (s, 6H), 2.70 (s, 3H), 2.95 (q, J=7.5 Hz, 2H), 7.73 (s, 2H), 7.75 (s, 2H).

Example 3

$^1$H NMR (CDCl$_3$): δ 0.99 (d, J=6.5 Hz, 6H), 1.40 (t, J=7.5 Hz, 3H), 2.19 (hept, J=6.5 Hz, 1H), 2.67 (s, 3H), 2.69 (s, 3H), 2.75 (d, J=7.3 Hz, 2H), 2.95 (q, J=7.8 Hz, 2H), 7.67 (s, 1H), 7.73 (s, 1H), 7.75 (s, 2H).

Example 4

$^1$H NMR (CDCl$_3$) δ 1.40 (t, J=7.5 Hz, 3H), 2.70 (s, 6H), 2.96 (q, J=7.5 Hz, 2H), 3.78 (s br, 1H), 4.86 (s, 2H), 7.75 (s, 2H), 7.84 (s, 2H).

Example 6

$^1$H NMR (CDCl$_3$): δ 1.03 (t, J=7.5 Hz, 3H), 1.77-1.89 (m, 2H), 2.66 (s, 6H), 2.69 (s, 3H), 2.88 (t, J=7.5 Hz, 2H), 7.72 (s, 3H), 7.74 (s, 1H).

Example 13

$^1$H NMR (D$_6$-DMSO): δ 0.92 (d, J=6.5 Hz, 6H), 1.11 (t, J=6.8 Hz, 3H), 2.06-2.17 (m, 1H), 2.41 (s, 3H), 2.60 (s, 3H), 2.72 (d, J=7.0 Hz, 2H), 3.06 (s, 3H), 3.63 (q, J=7.0 Hz, 2H), 6.98 (s, 1H), 7.04 (s, 1H), 7.73 (s, 1H), 7.80 (s, 1H).

Example 14

$^1$H NMR (CDCl$_3$): δ 0.98 (d, J=6.5 Hz, 6H), 0.99 (d, J=6.3 Hz, 6H), 2.13-2.28 (m, 2H), 2.43 (s, 3H), 2.68 (s, 3H), 2.77 (d, J=7.3 Hz, 4H), 7.68 (s, 1H), 7.74 (s, 1H), 8.16 (s, 1H), 9.14 (s, 1H).

Example 15

$^1$H NMR (CDCl$_3$): δ 2.51 (s, 3H), 2.55 (s, 3H), 3.19 (s, 6H), 3.22 (s, 6H), 7.07 (s, 2H), 7.15 (s, 2H).

Example 23

$^1$H NMR (CDCl$_3$): δ 1.21 (t, J=7.0 Hz, 3H), 2.02-2.10 (m, 4H), 2.50 (s, 3H), 2.53 (s, 3H), 3.14 (s, 3H), 3.56 (m, 4H), 3.70 (q, J=7.0 Hz, 2H), 6.92 (s, 1H), 7.05 (s, 1H), 7.12 (s, 1H), 7.15 (s, 1H).

Example 25

$^1$H NMR (CDCl$_3$): δ 1.01 (d, J=6.8 Hz, 6H), 1.38 (t, J=7.8 Hz, 3H), 2.18-2.30 (m, 1H), 2.46 (s, 3H), 2.66 (s, 3H), 2.80 (d, J=7.3 Hz, 2H), 2.92 (q, J=7.5 Hz, 2H), 7.73 (s, 2H), 8.22 (s, 1H), 9.20 (s, 1H).

Example 27

$^1$H NMR (CDCl$_3$): δ 1.00 (d, J=6.5 Hz, 6H), 1.38 (t, J=7.8 Hz, 3H), 1.89-2.01 (m, 1H), 2.48 (s, 3H), 2.64 (d, J=7.3 Hz, 2H), 2.66 (s, 3H), 2.92 (q, J=7.5 Hz, 2H), 7.80 (s, 2H), 8.10 (s, 1H), 8.56 (s, 1H).

Examples 28 to 33

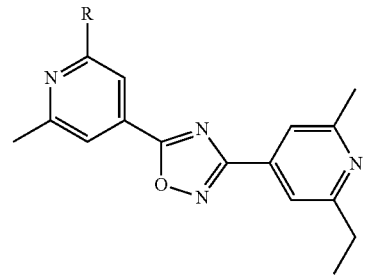

a) 2-Chloro-4-[3-(2-ethyl-6-methyl-4-pyridinyl)-[1,2,4]oxadiazol-5-yl]-6-methyl-pyridine (1.68 g) is obtained as a white solid following the general method for the preparation of 3,5-dipyridyl-[1,2,4]oxadiazoles starting from 2-chloro-6-methyl-isonicotinic acid (1.70 g, 9.91 mmol) and 2-ethyl-N-hydroxy-6-methyl-isonicotinamidine (1.78 g, 9.91 mmol); LC-MS: t$_R$=0.79 min, [M+1]$^+$=315.03; $^1$H NMR (CDCl$_3$): δ 1.39 (t, J=7.5 Hz, 3H), 2.68 (s, 3H), 2.72 (s, 3H), 2.94 (q, J=7.5 Hz, 2H), 7.73 (s, 2H), 7.88 (s, 1H), 7.96 (s, 1H).

b) To a solution of 2-chloro-4-[3-(2-ethyl-6-methyl-4-pyridinyl)-[1,2,4]oxadiazol-5-yl]-6-methyl-pyridine (1 eq.), sodium tert.-butylate (5 eq.) and the appropriate amine (5 eq.) in dioxane (5-10 mL/mmol oxadiazol), a degassed solution of Xantphos (0.37 eq.) in dioxane followed by Pd(OAc)$_2$ (0.21 eq.) is added. The mixture is stirred at 80° C. in a sealed vessel for 20 h before it is filtered. The filtrate is concentrated and the crude product is purified by prep. HPLC or on prep. TLC plates.

| Example No. | R | Scale [mmol] | LC-MS tR [min] | LC-MS [M + H]$^+$ | Amount Form |
|---|---|---|---|---|---|
| 28 | HN— | 1.27 | 0.58 | 310.10 | 107 mg yellow solid |
| 29 | HN— | 0.953 | 0.81 | 324.12 | 70 mg yellow solid |
| 30 | HN— | 0.953 | 0.63 | 338.17 | 64 mg yellow solid |
| 31 | N | 0.159 | 0.83 | 324.10 | 10 mg yellow resin |
| 32 | N | 0.159 | 0.87 | 338.13 | 10 mg yellow resin |
| 33 | N | 0.159 | 0.92 | 352.15 | 7 mg yellow resin |

Example 28

$^1$H NMR (CDCl$_3$): δ 1.39 (t, J=7.5 Hz, 3H), 2.52 (s, 3H), 2.67 (s, 3H), 2.93 (q, J=7.5 Hz, 2H), 3.02-3.06 (m, 3H), 4.82 (s br, 1H), 6.96 (s, 1H), 7.22 (s, 1H), 7.73 (s, 2H).

Example 30

$^1$H NMR (CDCl$_3$): δ 1.32 (d, J=6.0 Hz, 6H), 1.39 (t, J=7.5 Hz, 3H), 2.28 (s, 1H), 2.51 (s, 3H), 2.67 (s, 3H), 2.93 (q, J=7.3 Hz, 2H), 3.92-4.00 (m, 1H), 6.97 (s, 1H), 7.19 (s, 1H), 7.73 (s, 2H).

Examples 12, 13 and 34 to 38

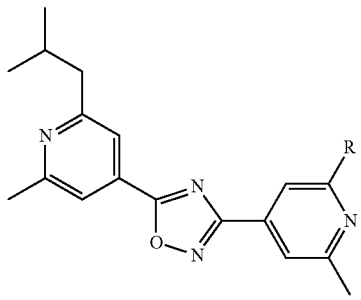

a) 2-Isobutyl-4-[3-(2-chloro-6-methyl-4-pyridinyl)-[1,2,4]oxadiazol-5-yl]-6-methyl-pyridine (1.50 g) is obtained as a white solid following the general method for the preparation of 3,5-dipyridyl-[1,2,4]oxadiazoles starting from 2-isobutyl-6-methyl-isonicotinic acid (2.50 g, 10.9 mmol) and 2-chloro-N-hydroxy-6-methyl-isonicotinamidine (2.69 g, 10.9 mmol); LC-MS*: t$_R$=1.30 min, [M+1]$^+$=343.07.

b) To a solution of 2-isobutyl-4-[3-(2-chloro-6-methyl-4-pyridinyl)-[1,2,4]oxadiazol-5-yl]-6-methyl-pyridine (1 eq.), sodium tert.-butylate (5 eq.) and the appropriate amine (5 eq.) in dioxane (5-10 mL/mmol oxadiazol), a degassed solution of Xantphos (0.37 eq.) in dioxane followed by Pd(OAc)$_2$ (0.21 eq.) is added. The mixture is stirred at 80° C. in a sealed vessel for 20 h before it is filtered. The filtrate is concentrated and the crude product is purified by prep. HPLC or on prep. TLC plates.

| Example No. | R | Scale [mmol] | LC-MS tR [min] | LC-MS [M + H]$^+$ | Amount Form |
|---|---|---|---|---|---|
| 34 | HN— | 0.159 | 0.97 | 338.09 | 3 mg pale yellow resin |
| 35 | HN—/ | 0.159 | 1.11 | 380.17 | 4 mg pale yellow resin |
| 36 | HN—/ | 0.159 | 1.08 | 366.14 | 9 mg pale yellow resin |
| 12 | /N\ | 0.159 | 0.99 | 352.17 | 8 mg pale yellow resin |
| 13 | /N\ | 0.159 | 1.05 | 366.17 | 4 mg pale yellow resin |
| 37 | /N\ | 0.159 | 1.12 | 380.18 | 6 mg pale yellow resin |
| 38 | /N\ | 0.159 | 1.11 | 380.17 | 4 mg pale yellow resin |

Examples 39 and 40

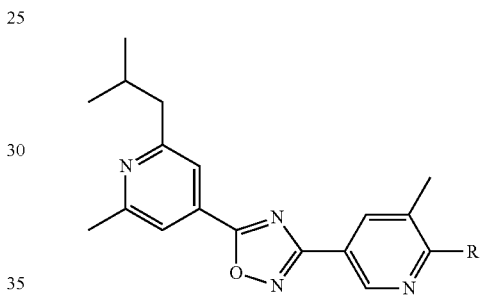

a) 2-Isobutyl-4-[3-(2-chloro-3-methyl-5-pyridinyl)-[1,2,4]oxadiazol-5-yl]-6-methyl-pyridine (290 mg) is obtained as a white solid following the general method for the preparation of 3,5-dipyridyl-[1,2,4]oxadiazoles starting from 2-isobutyl-6-methyl-isonicotinic acid (690 mg, 3.00 mmol) and 6-chloro-N-hydroxy-5-methyl-nicotinamidine (568 mg, 3.06 mmol); LC-MS*: t$_R$=1.17 min, [M+1]$^+$=343.28; $^1$H NMR (CDCl$_3$): δ 0.98 (d, J=6.5 Hz, 6H), 2.12-2.24 (m, 1H), 2.50 (s, 3H), 2.68 (s, 3H), 2.77 (d, J=7.3 Hz, 2H), 7.67 (s, 1H), 7.73 (s, 1H), 8.30 (s, 1H), 9.00 (s, 1H).

b) To a solution of 2-isobutyl-4-[3-(2-chloro-3-methyl-5-pyridinyl)-[1,2,4]oxadiazol-5-yl]-6-methyl-pyridine (1 eq.), Cs$_2$CO$_3$ (2.5 eq.) and the appropriate amine (5 eq.) in dioxane (5-10 mL/mmol oxadiazol), a degassed solution of Xantphos (0.37 eq.) in dioxane followed by Pd(OAc)$_2$ (0.21 eq.) is added. The mixture is stirred at 90° C. in a sealed vessel for 20 h before it is filtered. The filtrate is concentrated and the crude product is purified by prep. HPLC or on prep. TLC plates.

| Example No. | R | Scale [mmol] | LC-MS tR [min] | LC-MS [M + H]$^+$ | Amount Form |
|---|---|---|---|---|---|
| 39 | HN—/ | 0.06 | 0.74 | 366.15 | 2 mg pale yellow resin |

| Example No. | R | Scale [mmol] | LC-MS $t_R$ [min] | $[M+H]^+$ | Amount Form |
|---|---|---|---|---|---|
| 40 | (structure) | 0.06 | 0.74 | 352.13 | 3 mg pale yellow resin |

Example 40

$^1$H NMR (CDCl$_3$): δ 0.99 (d, J=6.5 Hz, 6H), 2.14-2.24 (m, 1H), 2.41 (s, 3H), 2.69 (s, 3H), 2.78 (d, J=7.5 Hz, 2H), 3.03 (s, 6H), 7.68 (s, 1H), 7.74 (s, 1H), 8.06 (s, 1H), 8.87 (s, 1H).

Example 41

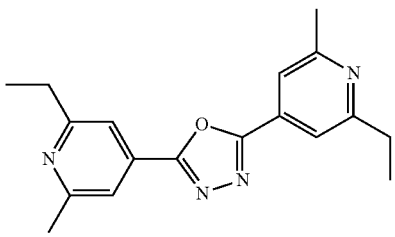 [SMILES: CCc1cc(-c2nnc(-c3cc(C)nc(CC)c3)o2)cc(C)n1]

A suspension of 2-ethyl-6-methyl-isonicotinic acid (80 mg, 0.397 mmol) in SOCl$_2$ (2 mL) is stirred at 65° C. for 1 h. The now clear solution is concentrated and dried to provide crude 2-ethyl-6-methyl-isonicotinic acid chloride. This material is dissolved in THF (4.5 mL) and treated with 1 M hydrazine in THF (1.59 mL, 1.59 mmol). The mixture is stirred at rt for 15 h before it is diluted with diethyl ether, washed with 1 M aq. HCl followed by 33% aq. KOH solution, dried over MgSO$_4$, filtered and concentrated to give crude 2-ethyl-6-methyl-isonicotinic acid N'-(2-ethyl-6-methyl-pyridine-4-carbonyl)-hydrazide (38 mg) as a white solid; LC-MS: $t_R$=0.47 min, $[M+1]^+$=327.41. This material is dissolved in DCM (5 mL) and pyridine (42 mg, 0.536 mmol) followed by trifluoromethanesulfonic anhydride (91 mg, 0.322 mmol) is added at 0° C. The mixture is stirred at 0° C. for 2 h before another portion of pyridine (42 mg, 0.536 mmol) and trifluoromethanesulfonic anhydride (61 mg, 0.214 mmol) is added. Stirring is continued for 2 h. The mixture is diluted with DCM, washed with water, dried over MgSO$_4$, filtered and the solvent of the filtrate is evaporated. The crude product is purified by prep. TLC with heptane:EA 7:3 to give 2-ethyl-4-[2-(2-ethyl-6-methyl-4-pyridinyl)-[1,3,4]oxadiazol-5-yl]-6-methyl-pyridine (16 mg) as a colourless oil; LC-MS: $t_R$=0.59 min, $[M+1]^+$=309.13; $^1$H NMR (CDCl$_3$): δ 1.39 (t, J=7.8 Hz, 6H), 2.68 (s, 6H), 2.94 (q, J=7.5 Hz, 4H), 7.70 (s, 4H).

Example 42

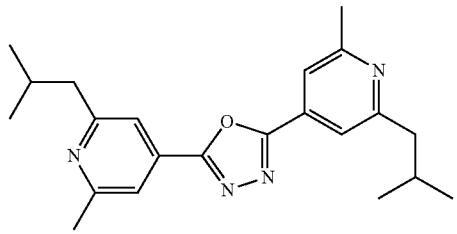 [SMILES: Cc1cc(-c2nnc(-c3cc(C)nc(CC(C)C)c3)o2)cc(CC(C)C)n1]

To a solution of 2-isobutyl-6-methyl-isonicotinic acid hydrochloride (41 mg, 0.178 mmol) and DIPEA (69 mg, 0.535 mmol) in DMF (2 mL) is added TBTU (57 mg, 0.178 mmol) at 0° C. The mixture is stirred for 30 min at 0° C. before 2-isobutyl-6-methyl-isonicotinic hydrazide (37 mg, 0.179 mmol) is added. Stirring is continued for 2 h. The mixture is diluted with ether (200 mL) and washed with 10% aq. citric acid solution (3×10 mL), sat. aq. NaHCO$_3$-solution (3×10 mL) and brine (10 mL), dried over MgSO$_4$, filtered and concentrated to give crude 2-isobutyl-6-methyl-isonicotinic acid N'-(2-isobutyl-6-methyl-pyridine-4-carbonyl)-hydrazide (70 mg) as a yellow oil; LC-MS: $t_R$=0.60 min, $[M+1]^+$=383.25. A part of this material (45 mg, 0.119 mmol) is dissolved in DCM (7 mL) and pyridine (47 mg, 0.595 mmol) followed by trifluoromethanesulfonic anhydride (37 mg, 0.131 mmol) is added at 0° C. The mixture is stirred for 2 h at 0° C. and 15 h at rt before it is diluted with DCM, washed with water, dried over MgSO$_4$, filtered and the solvent of the filtrate is evaporated. The crude product is purified by prep. TLC with heptane:EA 2:3 to give 2-isobutyl-4-[2-(2-isobutyl-6-methyl-4-pyridinyl)-[1,3,4]oxadiazol-5-yl]-6-methyl-pyridine (27 mg) as a colourless oil; LC-MS: $t_R$=0.72 min, $[M+1]^+$=365.54; $^1$H NMR (CDCl$_3$): δ 0.99 (d, J=6.5 Hz, 12H), 2.19 (hept, J=7.0 Hz, 2H), 2.68 (s, 6H), 2.77 (d, J=7.3 Hz, 4H), 7.64 (s, 2H), 7.69 (s, 2H).

Example 43

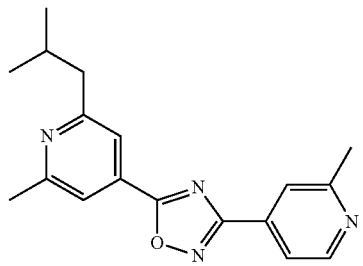

a) 2-Chloro-4-[3-(2-methyl-4-pyridinyl)-[1,2,4]oxadiazol-5-yl]-6-methyl-pyridine (1.50 g) is obtained as a white powder following the general method for the preparation of 3,5-dipyridyl-[1,2,4]oxadiazoles starting from 2-chloro-6-methyl-isonicotinic acid (499 mg, 2.91 mmol) and N-hydroxy-2-methyl-isonicotinamidine (550 mg, 2.91 mmol); LC-MS: $t_R$=0.78 min, $[M+1]^+$=287.01.

b) To a solution of 2-chloro-4-[3-(2-methyl-4-pyridinyl)-[1,2,4]oxadiazol-5-yl]-6-methyl-pyridine (200 mg, 0.698 mmol) in dioxane (10 mL), Pd(dppf) (11 mg, 14 µmol) and isobutyl zink bromide (2.8 mL, 0.5 M in THF) is added. The mixture is stirred at 80° C. for 3 h before another portion of isobutyl zink bromide (2.8 mL) is added. Stirring is continued at 80° C. for 72 h. The mixture is cooled to rt, diluted with water and extracted with EA. The org. extract is concentrated and the crude product is purified by prep. HPLC to give 2-isobutyl-4-[3-(2-methyl-4-pyridinyl)-[1,2,4]oxadiazol-5-yl]-6-methyl-pyridine (22 mg) as a beige solid; LC-MS: $t_R$=0.71 min, [M+1]$^+$=309.12.

Example 44

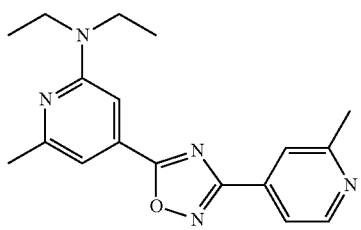

To a solution of 2-chloro-4-[3-(2-methyl-4-pyridinyl)-[1,2,4]oxadiazol-5-yl]-6-methyl-pyridine (160 mg, 0.558 mmol, Example 43a)) in dioxane (10 mL), Cs$_2$CO$_3$ (636 mg, 1.95 mmol) and diethylamine (204 mg, 2.79 mmol) is added. The mixture is degassed and put under N$_2$ before Pd(II) acetate (25 mg, 0.112 mmol) and Xantphos (116 mg, 0.201 mmol) is added. The mixture is stirred in a sealed vial at 90° C. for 72 h before it is cooled to rt. The mixture is filtered and the filtrate is evaporated. The crude product is purified on prep. TLC plates with heptane:EA 3:1 to give 2-diethylamino-4-[3-(2-methyl-4-pyridinyl)-[1,2,4]oxadiazol-5-yl]-6-methyl-pyridine (43 mg) as a yellow solid; LC-MS: $t_R$=0.66 min, [M+1]$^+$=324.15; $^1$H NMR δ 1.26 (t, J=7.0 Hz, 6H), 2.51 (s, 3H), 2.71 (s, 3H), 3.63 (q, J=7.0 Hz, 4H), 7.01 (s, 1H), 7.09 (s, 1H), 7.86 (d, J=5.0 Hz, 1H), 7.94 (s, 1H), 8.71 (d, J=5.0 Hz, 1H).

Examples 45 to 50

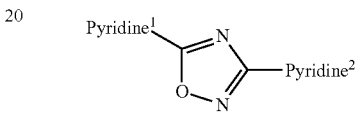

Following the general method for the preparation of 3,5-dipyridyl-[1,2,4]oxadiazoles, the following examples are prepared:

| Example No | Pyridine$^1$ (as acid) | Pyridine$^2$ (as hydroxyamidine) | LC-MS $t_R$ [min] | [M + H]$^+$ | Amount Form |
|---|---|---|---|---|---|
| 45 | ![structure] | ![structure] | 1.30* | 351.16 | 17 mg yellow oil |
| 46 | ![structure] | ![structure] | 0.75 | 353.20 | 18 mg resin |
| 47 | ![structure] | ![structure] | 0.86 | 340.17 | 75 mg orange oil |

| Example No | Pyridine[1] (as acid) | Pyridine[2] (as hydroxyamidine) | LC-MS $t_R$ [min] | [M + H]$^+$ | Amount Form |
|---|---|---|---|---|---|
| 48 | 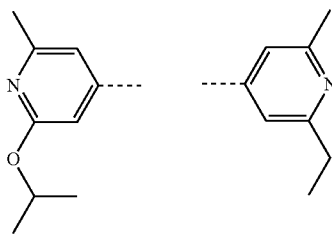 | 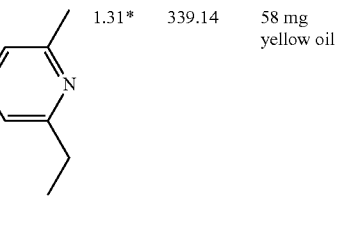 | 1.31* | 339.14 | 58 mg yellow oil |
| 49 | 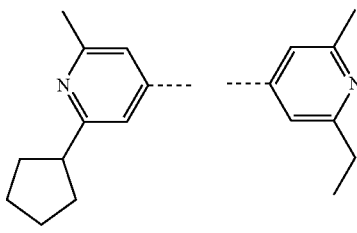 | 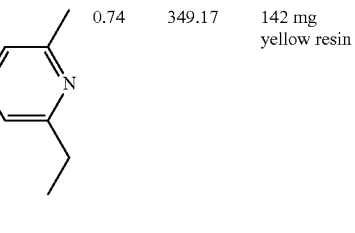 | 0.74 | 349.17 | 142 mg yellow resin |
| 50 | 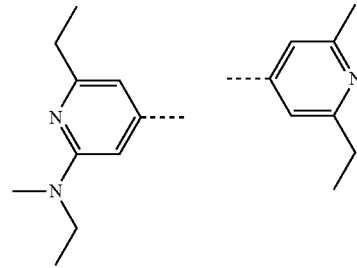 | 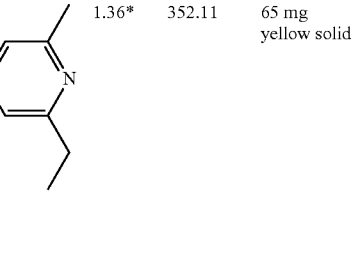 | 1.36* | 352.11 | 65 mg yellow solid |

*LC run under basic conditions, i.e. eluting with a gradient of acetontrile in water containing 13 mM of ammonium hydroxide; otherwise identical conditions.

Examples 51 to 58

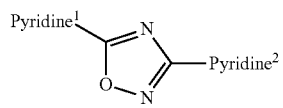

Following the general method for the preparation of 3,5-dipyridyl-[1,2,4]oxadiazoles, the following examples are prepared:

| Example No | Pyridine[1] (as acid) | Pyridine[2] (as hydroxyamidine) | LC-MS $t_R$ [min] | [M + H]$^+$ | Amount Form |
|---|---|---|---|---|---|
| 51 | 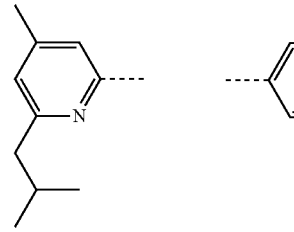 | 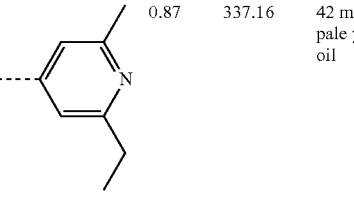 | 0.87 | 337.16 | 42 mg pale yellow oil |

-continued
| Example No | Pyridine[1] (as acid) | Pyridine[2] (as hydroxyamidine) | LC-MS $t_R$ [min] | [M + H]$^+$ | Amount Form |
|---|---|---|---|---|---|
| 52 | 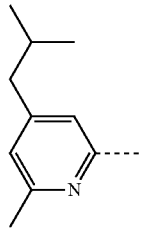 | 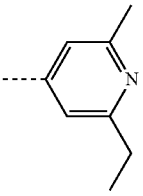 | 0.85 | 337.17 | 45 mg colourless oil |
| 53 | 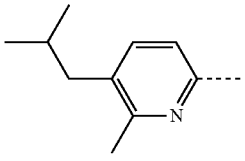 | | 0.84 | 323.15 | 82 mg white solid |
| 54 | 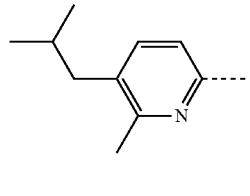 | | 0.86 | 337.16 | 91 mg white solid |
| 55 | 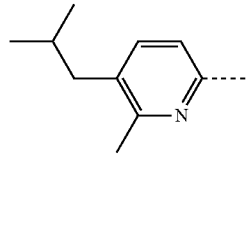 | 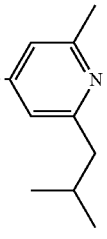 | 0.93 | 365.16 | 85 mg white solid |
| 56 | 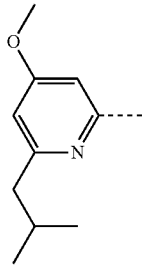 | 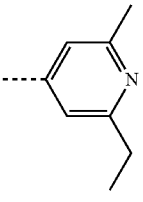 | 1.08 | 353.161 | 155 mg pale yellow oil |
| 57 | 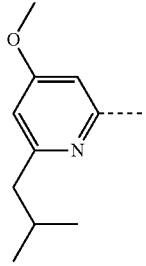 | 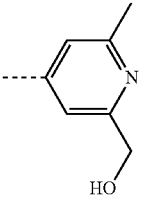 | 0.89 | 355.08 | 35 mg colourless oil |

-continued

| Example No | Pyridine[1] (as acid) | Pyridine[2] (as hydroxyamidine) | LC-MS $t_R$ [min] | [M + H]$^+$ | Amount Form |
|---|---|---|---|---|---|
| 58 | 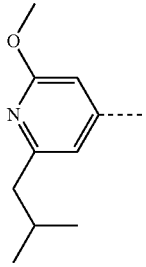 | 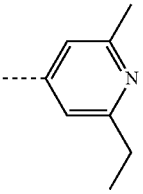 | 0.96 | 352.78 | 73 mg pale yellow solid |

Example 51

$^1$H NMR (CDCl$_3$): δ 1.00 (d, J=6.5 Hz, 6H), 1.39 (t, J=7.5 Hz, 3H), 2.19-2.29 (m, 1H), 2.49 (s, 3H), 2.66 (s, 3H), 2.81 (d, J=7.5 Hz, 2H), 2.92 (q, J=7.8 Hz, 2H), 7.20 (s, 1H), 7.78 (s, 2H), 8.01 (s, 1H).

Example 53

$^1$H NMR (CDCl$_3$): δ 1.00 (d, J=6.3 Hz, 6H), 1.92-2.03 (m, 1H), 2.62 (d, J=7.0 Hz, 2H), 2.65 (s, 6H), 2.72 (s, 3H), 7.62 (d, J=7.8 Hz, 1H), 7.78 (s, 2H), 8.09 (d, J=7.8 Hz, 1H).

Example 56

$^1$H NMR (CDCl$_3$): δ 1.38 (t, J=7.5 Hz, 3H), 2.17-2.28 (m, 1H), 2.65 (s, 3H), 2.78 (d, J=7.3 Hz, 2H), 2.91 (q, J=7.5 Hz, 2H), 3.98 (s, 3H), 6.87 (d, J=2.3 Hz, 1H), 7.70 (d, J=2.3 Hz, 1H), 7.77 (s, 2H).

Examples 59 to 70

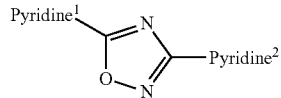

Following the general method for the preparation of 3,5-dipyridyl-[1,2,4]oxadiazoles, the following examples are prepared:

| Ex. No. | Pyridine[1] (as acid) | Pyridine[2] (as hydroxyamidine) | LC-MS $t_R$ [min] | [M + H]$^+$ | Amount Form |
|---|---|---|---|---|---|
| 59 | 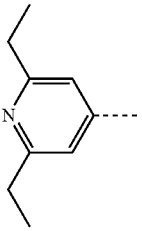 | 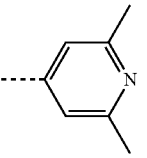 | 0.62 | 309.14 | 28 mg white solid |

-continued

| Ex. No. | Pyridine[1] (as acid) | Pyridine[2] (as hydroxyamidine) | LC-MS $t_R$ [min] | [M + H]$^+$ | Amount Form |
|---|---|---|---|---|---|
| 60 | | | 1.16* | 323.26 | 9 mg colourless resin |
| 61 | | | 0.72 | 337.19 | 44 mg beige oil |
| 62 | | | 1.32* | 351.26 | 10 mg colourless resin |
| 63 | | | 0.82 | 365.27 | 137 mg beige oil |
| 64 | | | 0.84 | 379.28 | 83 mg beige resin |

-continued

| Ex. No. | Pyridine¹ (as acid) | Pyridine² (as hydroxyamidine) | LC-MS $t_R$ [min] | [M + H]⁺ | Amount Form |
|---|---|---|---|---|---|
| 65 | | | 1.24* | 337.18 | 15 mg yellow solid |
| 66 | | | 0.69 | 335.07 | 37 mg brownish solid |
| 67 | | | 0.71 | 309.17 | 17 mg pale yellow solid |
| 68 | | | 0.76 | 323.16 | 34 mg pale yellow solid |
| 69 | | | 0.95 | 339.03 | 99 mg white solid |
| 70 | | | 0.96 | 367.10 | 22 mg brownish solid |

Example 63

$^1$H NMR (CDCl$_3$): δ 0.99 (d, J=6.5 Hz, 12H), 2.20 (hept, J=6.8 Hz, 2H), 2.68 (s, 6H), 2.80 (d, J=7.3 Hz, 4H), 7.70 (s, 2H), 7.75 (s, 2H).

Example 66

$^1$H NMR (CDCl$_3$): δ 1.72-1.95 (m, 6H), 2.13-2.23 (m, 2H), 2.67 (s, 6H), 2.69 (s, 3H), 3.26-3.35 (m, 1H), 7.73-7.75 (m, 3H), 7.76 (s, 1H).

Example 69

$^1$H NMR (CDCl$_3$): δ 1.00 (d, J=6.5 Hz, 6H), 2.14-2.25 (m, 1H), 2.58 (s, 3H), 2.70 (s, 3H), 2.78 (d, J=7.5 Hz, 2H), 4.01 (s, 3H), 7.31 (s, 1H), 7.48 (s, 1H), 7.69 (s, 1H), 7.75 (s, 1H).

Examples 71 to 82

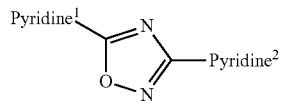

Following the general method for the preparation of 3,5-dipyridyl-[1,2,4]oxadiazoles, the following examples are prepared:

| Ex. No. | Pyridine$^1$ (as acid) | Pyridine$^2$ (as hydroxyamidine) | LC-MS $t_R$ [min] | [M + H]$^+$ | Amount Form |
|---|---|---|---|---|---|
| 71 | 2-isobutyl-pyridin-5-yl | 2,6-dimethyl-pyridin-4-yl | 0.76 | 309.02 | 20 mg brownish solid |
| 72 | 2-isobutyl-pyridin-5-yl | 2-methyl-6-ethyl-pyridin-4-yl | 0.66 | 341.01 | 36 mg yellow oil |
| 73 | 2-cyclopentyl-3-methyl-pyridin-5-yl | 2,6-dimethyl-pyridin-4-yl | 0.84 | 335.03 | 12 mg yellow oil |
| 74 | 2-cyclopentyl-3-methyl-pyridin-5-yl | 2-methyl-6-ethyl-pyridin-4-yl | 0.87 | 349.07 | 31 mg yellow solid |

-continued

| Ex. No. | Pyridine[1] (as acid) | Pyridine[2] (as hydroxyamidine) | LC-MS $t_R$ [min] | [M + H]$^+$ | Amount Form |
|---|---|---|---|---|---|
| 75 | | | 0.88 | 339.11 | 79 mg colourless oil |
| 76 | | | 1.29* | 339.16 | 7 mg pale yellow solid |
| 77 | | | 0.93 | 353.07 | 10 mg pale yellow solid |
| 78 | | | 0.77 | 338.12 | 5 mg pale yellow resin |
| 79 | | | 0.80 | 352.23 | 61 mg colourless oil |
| 80 | | | 0.84 | 366.23 | 64 mg colourless oil |
| 81 | | | 0.84 | 366.26 | 69 mg colourless oil |

| Ex. No. | Pyridine[1] (as acid) | Pyridine[2] (as hydroxyamidine) | LC-MS $t_R$ [min] | [M + H]$^+$ | Amount Form |
|---|---|---|---|---|---|
| 82 | HO— (structure) | (structure) | 0.78 | 311.17 | 39 mg white solid |

Example 75

$^1$H NMR (CDCl$_3$): δ 1.38 (t, J=7.5 Hz, 3H), 1.43 (d, J=6.3 Hz, 6H), 2.29 (s, 3H), 2.67 (s, 3H), 2.93 (q, J=7.5 Hz, 2H), 5.44-5.52 (m, 1H), 7.73 (s, 2H), 8.15 (s, 1H), 8.86 (s, 1H).

Examples 83 to 90

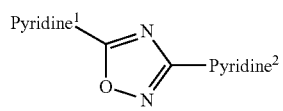

Following the general method for the preparation of 3,5-dipyridyl-[1,2,4]oxadiazoles, the following examples are prepared:

| Ex. No. | Pyridine[1] (as acid) | Pyridine[2] (as hydroxyamidine) | LC-MS $t_R$ [min] | [M + H]$^+$ | Amount Form |
|---|---|---|---|---|---|
| 83 | (structure) | (structure) | 0.58 | 328.95 | 33 mg beige solid |
| 84 | (structure) | (structure) | 0.61 | 343.04 | 24 mg off-white solid |
| 85 | (structure) | (structure) | 1.11* | 359.03 | 65 mg white solid |
| 86 | (structure) | (structure) | 0.59 | 324.01 | 16 mg pale yellow oil |

-continued

| Ex. No. | Pyridine¹ (as acid) | Pyridine² (as hydroxyamidine) | LC-MS $t_R$ [min] | [M + H]⁺ | Amount Form |
|---|---|---|---|---|---|
| 87 | | | 0.61 | 338.07 | 22 mg white solid |
| 88 | | | 0.57 | 324.13 | 22 mg white solid |
| 89 | | | 0.63 | 352.16 | 17 mg colourless oil |
| 90 | | | 0.62 | 352.16 | 27 mg colourless oil |

Example 87

¹H NMR (CDCl₃): δ 1.31 (d, J=6.3 Hz, 6H), 1.38 (t, J=7.8 Hz, 3H), 2.58 (s, 3H), 2.66 (s, 3H), 2.92 (q, J=7.5 Hz, 2H), 3.77-3.86 (m, 1H), 4.27 (d, J=7.5 Hz, 1H), 6.48 (d, J=2.3 Hz, 1H), 7.30 (d, J=2.3 Hz, 1H), 7.80 (s, 2H).

Example 88

¹H NMR (CDCl₃): δ 1.38 (t, J=7.8 Hz, 3H), 2.62 (s, 3H), 2.66 (s, 3H), 2.92 (q, J=7.8 Hz, 2H), 3.14 (s, 6H), 6.56 (d, J=1.3 Hz, 1H), 7.42 (d, J=1.8 Hz, 1H), 7.80 (s, 2H).

Examples 91 to 113

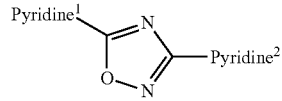

Following the general method for the preparation of 3,5-dipyridyl-[1,2,4]oxadiazoles, the following examples are prepared:

| Ex. No. | Pyridine¹ (as acid) | Pyridine² (as hydroxyamidine) | LC-MS $t_R$ [min] | [M + H]⁺ | Amount Form |
|---|---|---|---|---|---|
| 91 | | | 0.73 | 294.96 | 35 mg white solid |

-continued

| Ex. No. | Pyridine¹ (as acid) | Pyridine² (as hydroxyamidine) | LC-MS t_R [min] | [M + H]⁺ | Amount Form |
|---|---|---|---|---|---|
| 92 | | | 0.82 | 323.00 | 43 mg white solid |
| 93 | | | 0.89 | 337.07 | 42 mg yellow oil |
| 94 | | | 0.89 | 323.48 | 15 mg pale yellow solid |
| 95 | | | 0.89 | 337.97 | 32 mg off-white solid |
| 96 | | | 0.96 | 365.07 | 32 mg almost colourless oil |
| 97 | | | 0.93 | 380.10 | 48 mg yellow oil |
| 98 | | | 0.88 | 227.06 | 6 mg white solid |

-continued

| Ex. No. | Pyridine[1] (as acid) | Pyridine[2] (as hydroxyamidine) | LC-MS $t_R$ [min] | [M + H]$^+$ | Amount Form |
|---|---|---|---|---|---|
| 99 | | | 0.60 | 309.99 | 27 mg colourless oil |
| 100 | | | 0.61 | 356.08 | 32 mg pale yellow solid |
| 101 | | | 0.64 | 370.07 | 22 mg pale yellow solid |
| 102 | | | 0.83 | 323.02 | 8 mg colourless resin |
| 103 | | | 0.80 | 338.05 | 13 mg beige solid |
| 104 | | | 0.88 | 337.05 | 17 mg white solid |
| 105 | | | 0.84 | 352.09 | 18 mg beige solid |
| 106 | | | 0.89 | 323.41 | 4 mg white solid |

-continued

| Ex. No. | Pyridine¹ (as acid) | Pyridine² (as hydroxyamidine) | LC-MS $t_R$ [min] | [M + H]⁺ | Amount Form |
|---|---|---|---|---|---|
| 107 | | | 0.93 | 337.50 | 11 mg beige solid |
| 108 | | | 0.84 | 323.00 | 3 mg white solid |
| 109 | | | 0.88 | 337.02 | 34 mg white solid |
| 110 | | | 0.84 | 352.06 | 13 mg white solid |
| 111 | | | 0.85 | 323.01 | 11 mg white solid |
| 112 | | | 0.93 | 337.49 | 26 mg yellow solid |
| 113 | | | 0.79 | 339.03 | 62 mg white solid |

Example 95

$^1$H NMR (CDCl$_3$): δ 0.97 (d, J=6.8 Hz, 6H), 1.38 (t, J=7.8 Hz, 3H), 2.22 (hept, J=6.8 Hz, 1H), 2.45 (s, 3H), 2.67 (s, 3H), 2.78 (d, J=7.3 Hz, 2H), 2.93 (q, J=7.8 Hz, 2H), 7.11 (s, 1H), 7.78 (s, 2H), 7.87 (s, 1H).

Example 98

$^1$H NMR (CDCl$_3$): δ 0.98 (d, J=6.5 Hz, 6H), 1.39 (t, J=7.5 Hz, 3H), 2.02 (hept, J=6.8 Hz, 1H), 2.57 (d, J=7.3 Hz, 2H), 2.69 (s, 3H), 2.70 (s, 3H), 2.94 (q, J=7.5 Hz, 2H), 7.14 (d, J=0.8 Hz, 1H), 7.82 (s, 2H), 7.85 (d, J=0.8 Hz, 1H).

Example 99

$^1$H NMR (CDCl$_3$): δ 1.38 (t, J=7.5 Hz, 3H), 2.58 (s, 3H), 2.67 (s, 3H), 2.93 (q, J=8.3 Hz, 2H), 2.97 (s, 3H), 6.49 (d, J=2.0 Hz, 1H), 7.26 (d, J=2.3 Hz, 1H), 7.78 (s, 1H), 7.79 (s, 1H).

Example 109

$^1$H NMR (CDCl$_3$): δ 0.99 (d, J=6.5 Hz, 6H), 1.30 (t, J=7.5 Hz, 3H), 2.13-2.25 (m, 1H), 2.45 (s, 3H), 2.69 (s, 3H), 2.73-2.80 (m, 4H), 7.79 (s, 1H), 7.83 (s, 1H), 8.01 (s, 1H), 8.59 (s, 1H).

Example 113

$^1$H NMR (CDCl$_3$): δ 0.99 (d, J=6.8 Hz, 6H), 2.14-2.24 (m, 1H), 2.29 (s, 3H), 2.69 (s, 3H), 2.78 (d, J=7.0 Hz, 2H), 4.04 (s, 3H), 7.69 (s, 1H), 7.80 (s, 1H), 7.84 (s, 1H), 8.49 (s, 1H).

Example 114

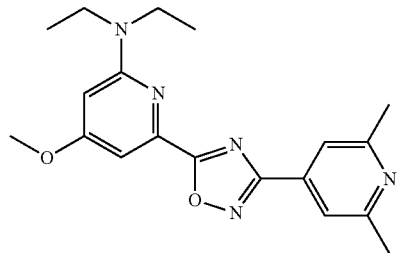

a) 2-Bromo-6-[3-(2,6-dimethyl-4-pyridinyl)-[1,2,4]oxadiazol-5-yl]-4-methoxy-pyridine (24 mg) is prepared following the general method for the preparation of 3,5-dipyridyl-[1,2,4]oxadiazoles starting from 6-bromo-4-methoxy-pyridine-2-carboxylic acid (150 mg, 0646 mmol) and N-hydroxy-2,6-dimethyl-isonicotinamidine (107 mg, 0.646 mmol); LC-MS: t$_R$=0.76 min, [M+1]$^+$=360.91.

b) 2-Diethylamino-6-[3-(2,6-dimethyl-4-pyridinyl)-[1,2,4]oxadiazol-5-yl]-4-methoxy-pyridine (5 mg) is obtained as a yellow oil by treating above 2-bromo-6-[3-(2,6-dimethyl-4-pyridinyl)-[1,2,4]oxadiazol-5-yl]-4-methoxy-pyridine (24 mg, 66 µmol) with diethylamine under Buchwald conditions as described for Example 44; LC-MS*: t$_R$=1.08 min, [M+1]$^+$=354.27; $^1$H NMR (CDCl$_3$). δ 1.26 (t, J=7.3 Hz, 6H), 2.66 (s, 6H), 3.63 (q, J=6.8 Hz, 4H), 3.94 (s, 3H), 6.13 (s, 1H), 7.20 (s, 1H), 7.75 (s, 2H).

Example 115

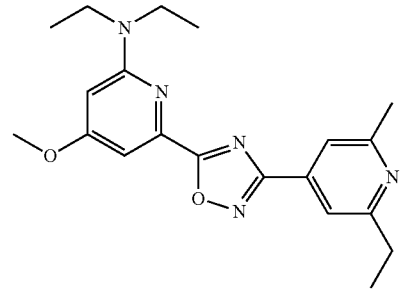 [SMILES: CCc1cc(-c2noc(-c3cc(OC)cc(N(CC)CC)n3)n2)cc(C)n1]

2-Diethylamino-6-[3-(2-ethyl-6-methyl-4-pyridinyl)-[1,2,4]oxadiazol-5-yl]-4-methoxy-pyridine is prepared in analogy to Example 114; LC-MS*: t$_R$=1.13 min, [M+1]$^+$=368.27.

Example 116

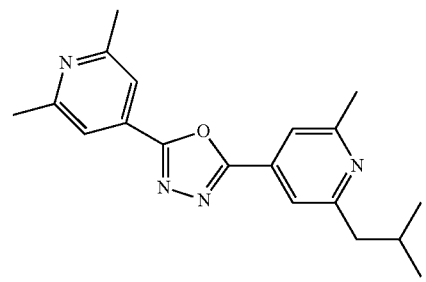 [SMILES: Cc1cc(-c2nnc(-c3cc(C)nc(CC(C)C)c3)o2)cc(C)n1]

2,6-Dimethyl-4-[2-(2-isobutyl-6-methyl-4-pyridinyl)-[1,3,4]oxadiazol-5-yl]-pyridine is obtained in analogy to Example 42 starting from 2-isobutyl-6-methyl-isonicotinic acid (40 mg, 174 µmol) and 2,6-dimethyl-isonicotinic acid hydrazide (35 mg, 261 µmol); LC-MS: t$_R$=0.63 min, [M+1]$^+$= 322.99; $^1$H NMR (CDCl$_3$): δ 1.00 (d, J=6.8 Hz, 6H), 2.19 (hept, J=6.8 Hz, 1H), 2.68 (s, 9H), 2.77 (d, J=7.5 Hz, 2H), 7.64 (s, 1H), 7.70 (s, 3H).

Example 117

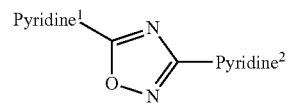

Following the general method for the preparation of 3,5-dipyridyl-[1,2,4]oxadiazoles, the following examples are prepared:

| Ex. No. | Pyridine¹ (as acid) | Pyridine² (as hydroxyamidine) | LC-MS $t_R$ [min] | [M + H]⁺ | Amount Form |
|---|---|---|---|---|---|
| 117 | 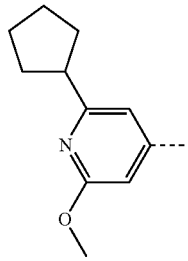 | 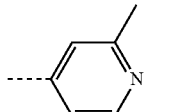 | 0.97 | 365.09 | 90 mg colourless oil |

Example 117

¹H NMR (CDCl₃): δ 1.39 (t, J=7.5 Hz, 3H), 1.71-1.80 (m, 2H), 1.83-1.95 (m, 4H), 2.07-2.16 (m, 2H), 2.67 (s, 3H), 2.93 (q, J=7.5 Hz, 2H), 3.21-3.30 (m, 1H), 4.03 (s, 3H), 7.31 (s, 1H), 7.51 (s, 1H), 7.74 (s, 2H).

Examples 118 to 123

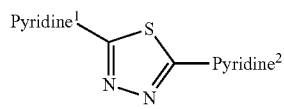

Following the general method for the preparation of 2,5-dipyridyl-[1,3,4]thiadiazoles, the following examples are prepared:

| Ex. No. | Pyridine¹ (as acid) | Pyridine² (as hydroxyamidine) | LC-MS $t_R$ [min] | [M + H]⁺ | Amount Form |
|---|---|---|---|---|---|
| 118 | 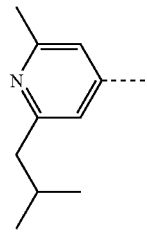 | 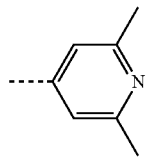 | 0.98 | 339.12 | 6 mg pale yellow solid |
| 119 | 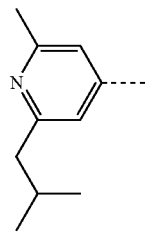 | 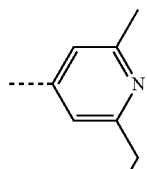 | 1.05 | 353.09 | 4 mg colourless resin |
| 120 | 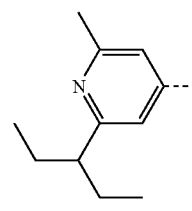 | 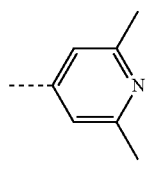 | 1.07 | 353.12 | 27 mg white solid |

| Ex. No. | Pyridine¹ (as acid) | Pyridine² (as hydroxyamidine) | LC-MS $t_R$ [min] | [M + H]⁺ | Amount Form |
|---|---|---|---|---|---|
| 121 | 6-methyl-2-(pentan-3-yl)pyridin-4-yl | 6-ethyl-2-methylpyridin-4-yl | 1.14 | 367.12 | 23 mg colourless resin |
| 122 | 2-(diethylamino)-6-methylpyridin-4-yl | 2,6-dimethylpyridin-4-yl | 1.12 | 354.12 | 27 mg yellow solid |
| 123 | 2-(diethylamino)-6-methylpyridin-4-yl | 6-ethyl-2-methylpyridin-4-yl | 1.19 | 368.14 | 44 mg yellow solid |

Example 120

¹H NMR (CDCl₃): δ 0.86 (t, J=7.3 Hz, 6H), 1.79 (quint, J=7.5 Hz, 4H), 2.64-2.71 (m, 10H), 7.52 (s, 1H), 7.55 (s, 1H), 7.59 (s, 2H).

Example 121

¹H NMR (CDCl₃): 0.86 (t, J=7.3 Hz, 6H), 81.39 (t, J=7.5 Hz, 3H), 1.79 (quint, J=7.3 Hz, 4H), 2.64-2.71 (m, 7H), 2.93 (q, J=7.8 Hz, 2H), 7.52 (s, 1H), 7.56 (s, 1H), 7.59 (s, 2H).

Example 122

¹H NMR (CDCl₃): δ 1.24 (t, J=7.3 Hz, 6H), 2.48 (s, 3H), 2.66 (s, 6H), 3.62 (q, J=7.3 Hz, 4H), 6.85 (s, 1H), 6.94 (s, 1H), 7.57 (s, 2H).

Examples 124 to 128

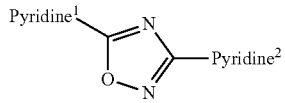

Following the general method for the preparation of 3,5-dipyridyl-[1,2,4]oxadiazoles, the following examples are prepared:

| Ex. No. | Pyridine¹ (as acid) | Pyridine² (as hydroxyamidine) | LC-MS $t_R$ [min] | [M + H]⁺ | Amount Form |
|---|---|---|---|---|---|
| 124 | 5-isobutyl-4-methoxypyridin-2-yl | 2,6-dimethylpyridin-4-yl | 0.82 | 339.01 | 8 mg white solid |

| Ex. No. | Pyridine¹ (as acid) | Pyridine² (as hydroxyamidine) | LC-MS $t_R$ [min] | [M + H]⁺ | Amount Form |
|---|---|---|---|---|---|
| 125 | | | 0.86 | 353.04 | 5 mg white crystalline solid |
| 126 | | | 0.87 | 338.02 | |
| 127 | | | 0.91 | 352.04 | |
| 128 | | | 0.98 | 380.10 | |

Example 125

¹H NMR (CDCl₃): δ 0.96 (d, J=6.5 Hz, 6H), 1.38 (t, J=7.5 Hz, 3H), 2.00 (hept, J=6.8 Hz), 2.59 (d, J=7.3 Hz, 2H), 2.66 (s, 3H), 2.92 (q, J=7.8 Hz, 2H), 4.05 (s, 3H), 7.78 (s, 1H), 7.80 (s, 2H), 8.47 (s, 1H).

Example 127

¹H NMR (CDCl₃): δ 1.25 (t, J=7.0 Hz, 6H), 1.39 (t, J=7.5 Hz, 3H), 2.37 (s, 3H), 2.69 (s, 3H), 2.95 (q, J=7.5 Hz, 2H), 3.64 (q, J=6.8 Hz, 4H), 6.47 (s, 1H), 7.29 (s, 1H), 7.77 (s, 2H).

Example 128

¹H NMR (CDCl₃): δ 1.00 (d, J=6.5 Hz, 6H), 1.25 (t, J=7.0 Hz, 6H), 2.14-2.25 (m, 1H), 2.37 (s, 3H), 2.69 (s, 3H), 2.78 (d, J=7.3 Hz, 2H), 3.64 (q, J=7.0 Hz, 4H), 6.47 (s, 1H), 7.29 (s, 1H), 7.71 (s, 1H), 7.77 (s, 1H).

Example 129

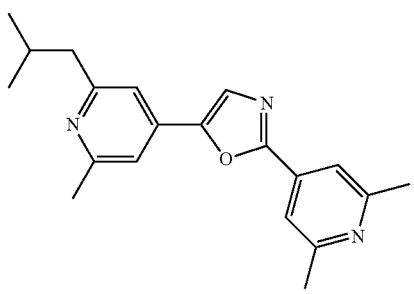 [SMILES: Cc1cc(-c2ncc(-c3cc(C)nc(CC(C)C)c3)o2)cc(C)n1]

a) To a solution of 2-methyl-6-(2-methyl-propyl)-isonicotinic acid (3.80 g, 16.5 mmol) in DCM (50 mL), DIPEA (10.7 g, 82.7 mmol) followed by TBTU (6.37 g, 19.9 mmol) is added. The mixture is stirred at rt for 10 min before N,O-dimethylhydroxylamine (1.94 g, 19.9 mmol) is added. The mixture is stirred at rt for 1 h before it is diluted with DCM, washed with sat. aq. NaHCO₃, followed by water, dried over MgSO₄, filtered and concentrated. The crude product is purified by CC on silic gel eluting with heptane:EA 1:1 to give 2-isobutyl-N-methoxy-6,N-dimethyl-isonicotinamide (3.37 g) as a colourless oil; LC-MS: $t_R$=0.61 min; ¹H NMR (CDCl₃): δ 0.95 (d, J=6.8 Hz, 6H), 2.06-2.18 (m, 1H), 2.60 (s, 3H), 2.69 (d, J=7.3 Hz, 2H), 3.37 (s, 3H), 3.57 (s, 3H), 7.13 (s, 1H), 7.18 (s, 1H).

b) To a solution of 2-isobutyl-N-methoxy-6,N-dimethyl-isonicotinamide (410 mg, 1.74 mmol) in THF (10 mL), methyl magnesium bromide (1.17 mL of a 3 M solution in ether, 3.47 mmol) is added at 5° C. The mixture is stirred at 5° C. for 1.5 h. The reaction is quenched by adding NH₄Cl. The mixture is diluted with EA (50 mL), washed with sat. aq. NaHCO₃, dried over Na₂SO₄, filtered and concentrated. The crude product is purified by CC on silica gel eluting with heptane:EA 4:1 to give 1-(2-isobutyl-6-methyl-pyridin-4-yl)-ethanone (280 mg) as a colourless oil. LC-MS: $t_R$=0.84 min; ¹H NMR (CDCl₃): δ 0.96 (d, J=6.5 Hz, 6H), 2.08-2.20 (m, 1H), 2.62 (s, 3H), 2.65 (s, 3H), 2.74 (d, J=7.3 Hz, 2H), 7.37 (s, 1H), 7.42 (s, 1H).

c) A solution of hydroxylamine hydrochloride (120 mg, 1.732 mmol) in water (0.5 mL) and 1 N aq. NaOH (1.2 mL) is added to 1-(2-isobutyl-6-methyl-pyridin-4-yl)-ethanone (276 mg, 1.44 mmol). The solution is stirred at 80° C. for 2 h and MeOH is added to maintain homogeneity of the mixture. The mixture is cooled to rt and the precipitate that forms is collected, washed with water and dried in vacuo to give 1-(2-isobutyl-6-methyl-pyridin-4-yl)-ethanone oxime (258 mg) as a white solid; ¹H NMR (D₆-DMSO): δ 0.88 (d, J=6.5 Hz, 6H), 1.98-2.10 (m, 1H), 2.13 (s, 3H), 2.45 (s, 3H), 2.56 (d, J=7.0 Hz, 2H), 7.22 (s, 1H), 7.27 (s, 1H), 11.54 (s, 1H).

d) To a solution of 1-(2-isobutyl-6-methyl-pyridin-4-yl)-ethanone oxime (125 mg, 0.606 mmol) in pyridine (0.4 mL), p-toluenesulfonyl chloride (127 mg, 0.667 mmol) is added at 5° C. The mixture is stirred at 5° C. for 15 h before another portion of p-toluene sulfonyl chloride (63 mg, 0.334 mmol) is added. Stirring is continued for 5 h. The solvent is evaporated and the remaining residue is partioned between water (15 mL) and EA (25 mL). The org. phase is separated, washed with water, dried over MgSO₄, filtered and concentrated. The crude product is purified by CC on silica gel eluting with heptane:EA 3:1 to 2:1 to give 1-(2-isobutyl-6-methyl-pyridin-4-yl)-ethanone oxime p-toluenesulfonic ester (177 mg) as a pale yellow oil; LC-MS: $t_R$=0.99*, [M+1]⁺=361.04.

e) A solution of potassium ethanolate (24% in water, 0.3 mL) is added to a solution of 1-(2-isobutyl-6-methyl-pyridin-4-yl)ethanone oxime p-toluenesulfonic ester (500 mg, 1.39 mmol) in EtOH (1.7 mL) at 5° C. The mixture is stirred at rt for 1 h. The mixture is diluted with ether and stirred for 30 min before it is filtered through celite. The filtrate is concentrated and dissolved in ether (25 mL). 2 N aq. HCl (15 mL) is added and the mixture is stirred at rt for 1 h. The org. phase is separated and extracted with 2 N aq. HCl (3×20 mL). The aq. extracts are combined and concentrated to give crude 2,2-diethoxy-2-(2-isobutyl-6-methyl-pyridin-4-yl)-ethylamine dihydrochloride (453 mg) as a yellow resin; LC-MS: $t_R$=0.84*, [M+1]⁺=281.23.

f) To a solution of 2,6-dimethyl-4-pyridine carboxylic acid hydrochloride (159 mg, 0.849 mmol) in DMF (6 mL), EDC (244 mg, 1.27 mmol) and HOBt (172 mg, 1.27 mmol) is added. The mixture is stirred at rt for 15 min before ethyl diisopropylamine (439 mg, 3.37 mmol) and a solution of 2,2-diethoxy-2-(2-isobutyl-6-methyl-pyridin-4-yl)-ethylamine dihydrochloride (300 mg, 0.849 mmol) in DMF (0.5 mL) is added. The mixture is stirred at rt for 4 h, diluted with EA (30 mL), and washed with sat. aq. NaHCO₃ (15 mL) and brine (15 mL). The org. extract is dried over Na₂SO₄, filtered and concentrated. The crude product is purified on prep. TLC plates with DCM containing 5% of methanol to give N-[2,2-diethoxy-2-(2-isobutyl-6-methyl-pyridin-4-yl)-ethyl]-2,6-dimethyl-isonicotinamide (444 mg) as a colourless resin; LC-MS: $t_R$=0.89*, [M+1]⁺=414.11; ¹H NMR (CDCl₃): δ 0.91 (d, J=6.5 Hz, 6H), 1.26 (t, J=6.8 Hz, 6H), 2.01-2.13 (m, 1H), 2.55 (s, 6H), 2.59 (s, 3H), 2.67 (d, J=7.3 Hz, 2H), 3.40-3.49 (m, 2H), 3.52-3.61 (m, 2H), 3.86 (d, J=5.5 Hz, 2H), 5.80 (s br, 1H), 7.04 (s, 2H), 7.10 (s, 1H), 7.16 (s, 1H).

g) To a solution of N-[2,2-diethoxy-2-(2-isobutyl-6-methyl-pyridin-4-yl)-ethyl]-2,6-dimethyl-isonicotinamide (60 mg, 0.177 mmol) in THF (4 mL), 25% aq. HCl (50 µL) is added and the mixture is stirred at 65° C. for 2 h. Another portion of 25% aq. HCl (50 µL) is added and stirring is continued at 65° C. for 3 h. The mixture is cooled to 0° C., neutralized by adding 1 N aq. NaOH solution and extracted twice with EA. The combined org. extracts are dried over Na₂SO₄, filtered and concentrated to give crude N-[2-(2-isobutyl-6-methyl-pyridin-4-yl)-2-oxo-ethyl]-2,6-dimethyl-isonicotinamide (48 mg) as an orange oil. Part of this material (22 mg) is purified on prep. TLC plates using DCM containing 10% of methanol to give N-[2-(2-isobutyl-6-methyl-pyridin-4-yl)-2-oxo-ethyl]-2,6-dimethyl-isonicotinamide (9 mg) as a pale yellow oil; LC-MS: $t_R$=0.75*, [M+1]⁺=330.13; ¹H NMR (CDCl₃): δ 0.97 (d, J=6.5 Hz, 6H), 2.09-2.21 (m, 1H), 2.64 (s, 6H), 2.67 (s, 3H), 2.75 (d, J=7.3 Hz, 2H), 4.94 (d, J=3.8 Hz, 2H), 7.23 (s br, 1H), 7.38 (s, 2H), 7.42 (s, 1H), 7.49 (s, 1H).

h) To a solution of N-[2-(2-isobutyl-6-methyl-pyridin-4-yl)-2-oxo-ethyl]-2,6-dimethyl-isonicotinamide (9 mg, 27 µmol) in THF (1 mL), Burgess reagent (20 mg, 80 µmol) is added. The mixture is stirred at 60° C. for 2 h before it is concentrated. The crude product is purified on prep. TLC plates with DCM containing 5% of methanol to give 2-isobutyl-4-[2-(2,6-dimethyl-4-pyridinyl)-oxazol-5-yl]-6-methyl-pyridine (5 mg) as a pale yellow wax; LC-MS: $t_R$=0.96*, [M+1]⁺=322.12; ¹H NMR (CDCl₃): δ 1.00 (d, J=6.8 Hz, 6H), 2.13-2.24 (m, 1H), 2.64 (s, 3H), 2.66 (s, 6H), 2.72 (d, J=7.3 Hz, 2H), 7.24 (s, 1H), 7.31 (s, 1H), 7.67 (s, 3H).

Example 130

GTPγS Assay to Determine EC₅₀ Values

GTPγS binding assays are performed in 96 well microtiter plates (Nunc, 442587) in a final volume of 200 µl, using membrane preparations of CHO cells expressing recombinant human S1P1 receptor. Assay conditions are 20 mM Hepes (Fluka, 54461), 100 mM NaCl (Fluka, 71378), 5 mM MgCl₂ (Fluka, 63064), 0.1% BSA (Calbiochem, 126609), 1 µM GDP (Sigma, G-7127), 2.5% DMSO (Fluka, 41644), 50 µM ³⁵S-GTPγS (Amersham Biosciences, SJ1320). The pH is 7.4. Test compounds are dissolved and diluted in 100% DMSO and pre-incubated at room temperature for 30 min in 150 µl of the above assay buffer, in the absence of ³⁵S-GTPγS. After addition of 50 µl of ³⁵S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na₂HPO₄/NaH₂PO₄ (70%/30%), dried, sealed at the bottom and, after addition of 25 µl MicroScint20 (Packard Biosciences, order#6013621), sealed on the top. Membrane-bound ³⁵S-GTPγS is measured with a TopCount from Packard Biosciences.

EC₅₀ is the concentration of agonist inducing 50% of the maximal specific ³⁵S-GTPγS binding. Specific binding is determined by subtracting non-specific binding from maximal binding. Maximal binding is the amount of cpm bound to the Multiscreen plate in the presence of 10 µM of S1P. Non-specific binding is the amount of binding in the absence of an agonist in the assay.

Agonistic activities (EC$_{50}$ values) of all exemplified compounds are in the range of 0.3-4250 nM with an average of 406 nM. Agonistic activities, determined according to the method described above, of some compounds of Formula (I) are displayed in Table 1:

TABLE 1

| Compound of Example | EC$_{50}$ [nM] |
|---|---|
| 2 | 5.2 |
| 6 | 2.4 |
| 8 | 0.4 |
| 29 | 0.9 |
| 39 | 6.1 |
| 45 | 0.4 |
| 61 | 1.0 |
| 62 | 1.4 |
| 65 | 0.5 |
| 66 | 0.3 |
| 117 | 2.1 |

Example 131

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p≤0.05.

As an example, Table 2 shows the effect on lymphocyte counts 6 h after oral administration of 10 mg/kg, or where indicated of 3 mg/kg, of some compounds of the present invention to normotensive male Wistar rats as compared to a group of animals treated with vehicle only.

TABLE 2

| Compound of Example | Lymphocyte counts |
|---|---|
| 3 | −77 ± 2% |
| 6* | −68% ± 3% |
| 7 | −69 ± 3% |
| 9 | −81 ± 1% |
| 11* | −55 ± 3% |
| 28 | −66% ± 3% |
| 30 | −64 ± 3% |
| 48 | −64 ± 4% |
| 58 | −62 ± 4% |
| 59* | −73 ± 1% |

*at a dose of 3 mg/kg.

The invention claimed is:

1. A compound of Formula (I),

Pyridine$^1$-A-Pyridine$^2$    Formula (I)

wherein
Pyridine$^1$ represents

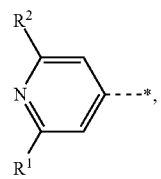

wherein the asterisks mark the bond with which the Pyridine$^1$ ring is bound to A;
R$^1$ represents C$_{1-5}$-alkyl, C$_{1-4}$-alkoxy, C$_{3-6}$-cycloalkyl, hydroxymethyl, or NR$^{1a}$R$^{1b}$;
R$^{1a}$ represents C$_{1-4}$-alkyl;
R$^{1b}$ represents hydrogen, or C$_{1-3}$-alkyl;
R$^2$ represents C$_{1-4}$-alkyl, or in case R$^1$ represents C$_{1-5}$-alkyl or C$_{3-6}$-cycloalkyl, R$^2$ may in addition represent methoxy;
A represents

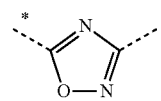

wherein the asterisks indicate the bond that is linked to the Pyridine$^1$ ring;
Pyridine$^2$ represents

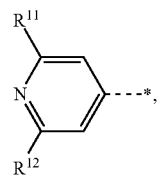

wherein the asterisks mark the bond with which the Pyridine$^2$ ring is bound to A;
R$^{11}$ represents C$_{1-4}$-alkyl, C$_{1-3}$-alkoxy, hydroxymethyl, or NR$^{11a}$R$^{11b}$;
R$^{11a}$ represents C$_{1-3}$-alkyl;
R$^{11b}$ represents hydrogen, or C$_{1-2}$-alkyl;
R$^{12}$ represents or C$_{1-2}$-alkyl;
with the exception of 3-(2-ethyl-4-pyridyl)-5-(2-ethyl-4-pyridyl)-1,2,4-oxadiazole;
in free or salt form.

2. The compound according to claim 1, wherein R$^2$ represents C$_{1-4}$-alkyl, in free or salt form.

3. The compound according to claim 1, wherein R$^1$ represents C$_{2-5}$-alkyl, C$_{2-3}$-alkoxy, cyclopentyl, or NR$^{1a}$R$^{1b}$, wherein R$^{1a}$ represents C$_{1-3}$-alkyl and R$^{1b}$ represents hydrogen, or C$_{1-2}$-alkyl; and R$^2$ represents C$_{1-2}$-alkyl;
in free or salt form.

4. The compound according to claim 1, wherein
R$^{11}$ represents C$_{1-4}$-alkyl, hydroxymethyl, or NR$^{11a}$R$^{11b}$;
R$^{11a}$ represents C$_{1-3}$-alkyl;
R$^{11b}$ represents hydrogen, or C$_{1-2}$-alkyl;
R$^{12}$ represents C$_{1-2}$-alkyl;
in free or salt form.

5. The compound according to claim 1, wherein R$^{11}$ represents methyl, ethyl, hydroxymethyl, methylamino, or dimethylamino; and R$^{12}$ represents methyl;
in free or salt form.

6. The compound according to claim 1 selected from the group consisting of:

2-ethyl-4-[3-(2,6-dimethyl-4-pyridinyl)-[1,2,4]oxadiazol-5-yl]-6-methyl-pyridine;
2-ethyl-4-[3-(2-ethyl-6-methyl-4-pyridinyl)-[1,2,4]oxadiazol-5-yl]-6-methyl-pyridine;
2-ethyl-4-[3-(2-isobutyl-6-methyl-4-pyridinyl)-[1,2,4]oxadiazol-5-yl]-6-methyl-pyridine;
2-propyl-4-[3-(2,6-dimethyl-4-pyridinyl)-[1,2,4]oxadiazol-5-yl]-6-methyl-pyridine;
2-propyl-4-[3-(2-ethyl-6-methyl-4-pyridinyl)-[1,2,4]oxadiazol-5-yl]-6-methyl-pyridine;
2-isobutyl-4-[3-(2,6-dimethyl-4-pyridinyl)-[1,2,4]oxadiazol-5-yl]-6-methyl-pyridine;
2-isobutyl-4-[3-(2-ethyl-6-methyl-4-pyridinyl)-[1,2,4]oxadiazol-5-yl]-6-methyl-pyridine;
2-methylamino-4-[3-(2-ethyl-6-methyl-4-pyridinyl)-[1,2,4]oxadiazol-5-yl]-6-methyl-pyridine;
2-ethylamino-4-[3-(2-ethyl-6-methyl-4-pyridinyl)-[1,2,4]oxadiazol-5-yl]-6-methyl-pyridine;
2-isopropylamino-4-[3-(2-ethyl-6-methyl-4-pyridinyl)-[1,2,4]oxadiazol-5-yl]-6-methyl-pyridine;
2-diethylamino-4-[3-(2-ethyl-6-methyl-4-pyridinyl)-[1,2,4]oxadiazol-5-yl]-6-methyl-pyridine;
2-isobutyl-4-[3-(2-methylamino-6-methyl-4-pyridinyl)-[1,2,4]oxadiazol-5-yl]-6-methyl-pyridine;
and 2-(1-ethyl-propyl)-4-[3-(2-ethyl-6-methyl-4-pyridinyl)-[1,2,4]oxadiazol-5-yl]-6-methyl-pyridine;

in free or salt form.

7. The compound according to claim 1 selected from the group consisting of:

2-isopropoxy-4-[3-(2-ethyl-6-methyl-4-pyridinyl)-[1,2,4]oxadiazol-5-yl]-6-methyl-pyridine;
2-isobutyl-4-[3-(2-ethyl-6-methyl-4-pyridinyl)-[1,2,4]oxadiazol-5-yl]-6-methoxy-pyridine;
2,6-diethyl-4-[3-(2,6-dimethyl-4-pyridinyl)-[1,2,4]oxadiazol-5-yl]-pyridine;
2,6-diethyl-4-[3-(2-ethyl-6-methyl-4-pyridinyl)-[1,2,4]oxadiazol-5-yl]-pyridine;
2-isobutyl-4-[3-(2,6-dimethyl-4-pyridinyl)-[1,2,4]oxadiazol-5-yl]-6-ethyl-pyridine;
2-isobutyl-4-[3-(2-ethyl-6-methyl-4-pyridinyl)-[1,2,4]oxadiazol-5-yl]-6-ethyl-pyridine;
2-(3-pentyl)-4-[3-(2,6-dimethyl-4-pyridinyl)-[1,2,4]oxadiazol-5-yl]-6-methyl-pyridine;
2-cyclopentyl-4-[3-(2,6-dimethyl-4-pyridinyl)-[1,2,4]oxadiazol-5-yl]-6-methyl-pyridine;
6-methoxy-2-(3-pentyl)-4-[3-(2-ethyl-6-methyl-4-pyridinyl)-[1,2,4]oxadiazol-5-yl]-pyridine; and
2-cyclopentyl-4-[3-(2-ethyl-6-methyl-4-pyridinyl)-[1,2,4]oxadiazol-5-yl]-6-methoxy-pyridine;

in free or salt form.

8. A pharmaceutical composition comprising the compound according to claim 1 in free or pharmaceutically acceptable salt form, and a pharmaceutically acceptable carrier.

* * * * *

UNITED STATES PATENT AND TRADEMARK OFFICE
CERTIFICATE OF CORRECTION

Page 1 of 1

PATENT NO. : 8,598,208 B2
APPLICATION NO. : 12/673918
DATED : December 3, 2013
INVENTOR(S) : Bolli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 367 days.

Signed and Sealed this
Fourteenth Day of April, 2015

Michelle K. Lee
*Director of the United States Patent and Trademark Office*